United States Patent
Suga et al.

(10) Patent No.: US 10,329,558 B2
(45) Date of Patent: Jun. 25, 2019

(54) METHOD FOR PRODUCING COMPOUND CONTAINING HETEROCYCLE

(71) Applicant: The University of Tokyo, Tokyo (JP)

(72) Inventors: Hiroaki Suga, Tokyo (JP); Yuki Goto, Tokyo (JP); Shotaro Tsunoda, Tokyo (JP)

(73) Assignee: The University of Tokyo, Tokyo (JP)

( * ) Notice: Subject to any disclaimer, the term of this patent is extended or adjusted under 35 U.S.C. 154(b) by 825 days.

(21) Appl. No.: 14/772,076

(22) PCT Filed: Mar. 7, 2014

(86) PCT No.: PCT/JP2014/056069
§ 371 (c)(1),
(2) Date: Dec. 3, 2015

(87) PCT Pub. No.: WO2014/136971
PCT Pub. Date: Sep. 12, 2014

(65) Prior Publication Data
US 2016/0083719 A1    Mar. 24, 2016

(30) Foreign Application Priority Data
Mar. 7, 2013 (JP) ................................. 2013-045888

(51) Int. Cl.
*C12N 15/10* (2006.01)
*C12P 21/02* (2006.01)
*C12N 9/00* (2006.01)
*C07K 1/107* (2006.01)

(52) U.S. Cl.
CPC ........ *C12N 15/1068* (2013.01); *C07K 1/1077* (2013.01); *C12N 9/00* (2013.01); *C12P 21/02* (2013.01)

(58) Field of Classification Search
None
See application file for complete search history.

(56) References Cited

U.S. PATENT DOCUMENTS

2014/0113830 A1    4/2014  Suga et al.

FOREIGN PATENT DOCUMENTS

WO    2007103739 A2    9/2007
WO    2012121392 A1    9/2012

OTHER PUBLICATIONS

Oman et al ( Nature Chemical Biology 6:9-18) (Year: 2010).*
Robertset al (PNAS 94:12297-302) (Year: 1997).*
Ito, et al., "A comprehensive study on the substrate tolerance of a promiscuous heterocyclase PatD", Dec. 1, 2011, p. 1P, Publisher: Annual Meeting of the Molecular Biology Society of Japan Program Yoshishu, Molecular Biology Society of Japan, JP.
Ito, et al., "4 B4-36 Substrate preference studies of a post-translational modification enzyme, PatD, toward the construction of azoline-containing chemical libr . . . ", Mar. 11, 2011, p. 724 vol. 91, Publisher: Nippon Kagakkan Koen Yokoshu—Chemical Society of Japan, Preprints of the Conference, Nippon Kagakukai, Tokyo, JP.
International Search Report received in PCT/JP2014/056069, dated Apr. 22, 2014.
Lee, et al., "Discovery of a widely distributed toxin biosynthetic", Apr. 15, 2008, pp. 5879-5884, vol. 105, No. 15, Publisher: PNAS.

* cited by examiner

*Primary Examiner* — Christopher M Gross
(74) *Attorney, Agent, or Firm* — Suzannah K. Sundby, Esq.; Canady + Lortz LLP

(57) ABSTRACT

An object of the present invention is to provide a method of stably introducing a heterocycle into a substrate peptide by using an azoline backbone introducing enzyme.
The present invention provides a method of introducing a heterocycle into a leader-sequence-free substrate peptide by using an azoline backbone introducing enzyme to which a leader sequence of the substrate has been bound.

25 Claims, 28 Drawing Sheets

Specification includes a Sequence Listing.

FIG. 2A

NdeI-LS-GS15-PatD

MGHHHHHHHHHSSGHIEGRH MNKKNILPQQGQPVIRLTAGQLSSQLAELSEEALGDAG SGSGSGSGSGSGSGSGSGSGSGSGSG SHMQPTALQIKPHFHVEIIEPKQVYLLGEQGNHALTGQLYC
QILPFLNGEYTREQIVEKLDGQVPEEYIDFVLSRLVEKGYLTEVAPELSLEVAAFWSELGIAPS
VVAEGLKQPVTVTTAGKGIREGIVANLAAALEEAGIQVSDPKAPKAPKAGDSTAQLQVVLTDDY
LQPELAAINKEALERQQPWLLVKPVGSILWLGPLFVPGETGCWHCLAQRLRGNREVEASVLQQK
RALQERNGQNKNGAVSCLPTARATLPSTLQTGLQWAATEIAKWMVKRHLNAIAPGTARFPTLAG
KIFTFNQTTLELKAHPLSRRPQCPTCGDQEILQRRGFEPLKLESRPKHFTSDGGHRATTPEQTV
QKYQHLIGPITGVVTELVRISDPANPLVHTYRAGHSFGSSAGSLRGLRNTLRYKSSGKGKTDSQ
SRASGLCEAIERYSGIFLGDEPRKRATLAELGDLAIHPEQCLHFSDRQYDNRDALNAEGSAAAY
RWIPHRFAASQAIDWTPLWSLTEQKHKYVPTAICYYNYLLPPADRFCKADSNGNAAGNSLEEAI
LQGFMELVERDSVALWWYNRLRRPEVELSSFEEPYFLQLQQFYRSQNRELWVLDLTADLGIPAF
AGLSRRTVGSSERVSIGFGAHLDPKIAILRALTEVSQVGLELDKVPDEKLDGESKDWMLEVTLE
THPCLAPDPSQPRKTANDYPKRWSDDIYTDVMACVEMAKVAGLETLVLDQTRPDIGLNVVKVMI
PGMRTFWSRYGPGRLYDVPVQLGWLKEPLAEAEMNPTNIPF*

NdeI-LS-GS35-PatD

MGHHHHHHHHHSSGHIEGRH MNKKNILPQQGQPVIRLTAGQLSSQLAELSEEALGDA SGSGS GSGSGSGSGSGSGSGSGSGSGSGSGSGSGSGSGSGSGSGSGSGSGSGSGSGSGSGSGSGSGSGS
HMQPTALQIKPHFHVEIIEPKQVYLLGEQGNHALTGQLYCQILPFLNGEYTREQIVEKLDGQVP
EEYIDFVLSRLVEKGYLTEVAPELSLEVAAFWSELGIAPSVVAEGLKQPVTVTTAGKGIREGIV
ANLAAALEEAGIQVSDPKAPKAPKAGDSTAQLQVVLTDDYLQPELAAINKEALERQQPWLLVKP
VGSILWLGPLFVPGETGCWHCLAQRLRGNREVEASVLQQKRALQERNGQNKNGAVSCLPTARAT
LPSTLQTGLQWAATEIAKWMVKRHLNAIAPGTARFPTLAGKIFTFNQTTLELKAHPLSRRPQCP
TCGDQEILQRRGFEPLKLESRPKHFTSDGGHRATTPEQTVQKYQHLIGPITGVVTELVRISDPA
NPLVHTYRAGHSFGSSAGSLRGLRNTLRYKSSGKGKTDSQSRASGLCEAIERYSGIFLGDEPRK
RATLAELGDLAIHPEQCLHFSDRQYDNRDALNAEGSAAAYRWIPHRFAASQAIDWTPLWSLTEQ
KHKYVPTAICYYNYLLPPADRFCKADSNGNAAGNSLEEAILQGFMELVERDSVALWWYNRLRRP
EVELSSFEEPYFLQLQQFYRSQNRELWVLDLTADLGIPAFAGLSRRTVGSSERVSIGFGAHLDP
KIAILRALTEVSQVGLELDKVPDEKLDGESKDWMLEVTLETHPCLAPDPSQPRKTANDYPKRWS
DDIYTDVMACVEMAKVAGLETLVLDQTRPDIGLNVVKVMIPGMRTFWSRYGPGRLYDVPVQLGW
LKEPLAEAEMNPTNIPF*

FIG. 2B

NheI-LS-GS5-PatD

MGHHHHHHHHHSSGHIEGRASNKKNILPQQGQPVIRLTAGQLSSQLAELSEEALGDAGSGSG
SGSHMQPTALQIKPHFHVEIIEPKQVYLLGEQGNHALTGQLYCQILPFLNGEYTREQIVEKLD
GQVPEEYIDFVLSRLVEKGYLTEVAPELSLEVAAFWSELGIAPSVVAEGLKQPVTVTTAGKGIR
EGIVANLAAALEEAGIQVSDPKAPKAPKAGDSTAQLQVVLTDDYLQPELAAINKEALERQQPWL
LVKPVGSILWLGPLFVPGETGCWHCLAQRLRGNREVEASVLQQKRALQERNGQNKNGAVSCLPT
ARATLPSTLQTGLQWAATEIAKWMVKRHLNAIAPGTARFPTLAGKIFTFNQTTLELKAHPLSRR
PQCPTCGDQEILQRRGFEPLKLESRPKHFTSDGGHRATTPEQTVQKYQHLIGPITGVVTELVRI
SDPANPLVHTYRAGHSFGSSAGSLRGLRNTLRYKSSGKGKTDSQSRASGLCEAIERYSGIFLGD
EPRKRATLAELGDLAIHPEQCLHFSDRQYDNRDALNAEGSAAAYRWIPHRFAASQAIDWTPLWS
LTEQKHKYVPTAICYYNYLLPPADRFCKADSNGNAAGNSLEEAILQGFMELVERDSVALWWYNR
LRRPEVELSSFEEPYFLQLQQFYRSQNRELWVLDLTADLGIPAFAGLSRRTVGSSERVSIGFGA
HLDPKIAILRALTEVSQVGLELDKVPDEKLDGESKDWMLEVTLETHPCLAPDPSQPRKTANDYP
KRWSDDIYTDVMACVEMAKVAGLETLVLDQTRPDIGLNVVKVMIPGMRTFWSRYGPGRLYDVPV
QLGWLKEPLAEAEMNPTNIPF*

NheI-LS-GS15-PatD

MGHHHHHHHHHSSGHIEGRASNKKNILPQQGQPVIRLTAGQLSSQLAELSEEALGDAGSGGS
GSGSGSGSGSGSGSHMQPTALQIKPHFHVEIIEPKQVYLLGEQGNHALTGQLYC
QILPFLNGEYTREQIVEKLDGQVPEEYIDFVLSRLVEKGYLTEVAPELSLEVAAFWSELGIAPS
VVAEGLKQPVTVTTAGKGIREGIVANLAAALEEAGIQVSDPKAPKAPKAGDSTAQLQVVLTDDY
LQPELAAINKEALERQQPWLLVKPVGSILWLGPLFVPGETGCWHCLAQRLRGNREVEASVLQQK
RALQERNGQNKNGAVSCLPTARATLPSTLQTGLQWAATEIAKWMVKRHLNAIAPGTARFPTLAG
KIFTFNQTTLELKAHPLSRRPQCPTCGDQEILQRRGFEPLKLESRPKHFTSDGGHRATPEQTV
QKYQHLIGPITGVVTELVRISDPANPLVHTYRAGHSFGSSAGSLRGLRNTLRYKSSGKGKTDSQ
SRASGLCEAIERYSGIFLGDEPRKRATLAELGDLAIHPEQCLHFSDRQYDNRDALNAEGSAAAY
RWIPHRFAASQAIDWTPLWSLTEQKHKYVPTAICYYNYLLPPADRFCKADSNGNAAGNSLEEAI
LQGFMELVERDSVALWWYNRLRRPEVELSSFEEPYFLQLQQFYRSQNRELWVLDLTADLGIPAF
AGLSRRTVGSSERVSIGFGAHLDPKIAILRALTEVSQVGLELDKVPDEKLDGESKDWMLEVTLE
THPCLAPDPSQPRKTANDYPKRWSDDIYTDVMACVEMAKVAGLETLVLDQTRPDIGLNVVKVMI
PGMRTFWSRYGPGRLYDVPVQLGWLKEPLAEAEMNPTNIPF*

FIG. 2C

NheI-LS-GS25-PatD

MGHHHHHHHHHHSSGHIEGRASNKKNILPQQGQPVIRLTAGQLSSQLAELSEEALGDAGSGGS
GSGGSGSGGSGSGGSGSGGSGSGGSHMQPTALQIKPHFHVEIIEP
KQVYLLGEQGNHALTGQLYCQILPFLNGEYTREQIVEKLDGQVPEEYIDFVLSRLVEKGYLTEV
APELSLEVAAFWSELGIAPSVVAEGLKQPVTVTTAGKGIREGIVANLAAALEEAGIQVSDPKAP
KAPKAGDSTAQLQVVLTDDYLQPELAAINKEALERQQPWLLVKPVGSILWLGPLFVPGETGCWH
CLAQRLRGNREVEASVLQQKRALQERNGQNKNGAVSCLPTAPATLPSTLQTGLQWAATEIAKWM
VKRHLNAIAPGTARFPTLAGKIFTFNQTTLELKAHPLSRRPQCPTCGDQEILQRRGFEPLKLES
RPKHFTSDGGHRATTPEQTVQKYQHLIGPITGVVTELVRISDPANPLVHTYRAGHSFGSSAGSL
RGLRNTLRYKSSGKGKTDSQSRASGLCEAIERYSGIFLGDEPRKRATLAELGDLAIHPEQCLHF
SDRQYDNRDALNAEGSAAAYRWIPHRFAASQAIDWTPLWSLTEQKHKYVPTAICYYNYLLPPAD
RFCKADSNGNAAGNSLEEAILQGFMELVERDSVALWWYNRLRRPEVELSSFEEPYFLQLQQFYR
SQNRELWVLDLTADLGIPAFAGLSRRTVGSSERVSIGFGAHLDPKIAILRALTEVSQVGLELDK
VPDEKLDGESKDWMLEVTLETHPCLAPDPSQPRKTANDYPKRWSDDIYTDVMACVEMAKVAGLE
TLVLDQTRPDIGLNVVKVMIPGMRTFWSRYGPGRLYDVPVQLGWLKEPLAEAEMNPTNIPF*

NheI-LS-GS35-PatD

MGHHHHHHHHHHSSGHIEGRASNKKNILPQQGQPVIRLTAGQLSSQLAELSEEALGDAGSGGS
GSGGSGSGGSGSGGSGSGGSGSGGSGSGGSGSGGSGSGGSGSGGSGSGGS
HMQPTALQIKPHFHVEIIEPKQVYLLGEQGNHALTGQLYCQILPFLNGEYTREQIVEKLDGQVP
EEYIDFVLSRLVEKGYLTEVAPELSLEVAAFWSELGIAPSVVAEGLKQPVTVTTAGKGIREGIV
ANLAAALEEAGIQVSDPKAPKAPKAGDSTAQLQVVLTDDYLQPELAAINKEALERQQPWLLVKP
VGSILWLGPLFVPGETGCWHCLAQRLRGNREVEASVLQQKRALQERNGQNKNGAVSCLPTARAT
LPSTLQTGLQWAATEIAKWMVKRHLNAIAPGTARFPTLAGKIFTFNQTTLELKAHPLSRRPQCP
TCGDQEILQRRGFEPLKLESRPKHFTSDGGHRATTPEQTVQKYQHLIGPITGVVTELVRISDPA
NPLVHTYRAGHSFGSSAGSLRGLRNTLRYKSSGKGKTDSQSRASGLCEAIERYSGIFLGDEPRK
RATLAELGDLAIHPEQCLHFSDRQYDNRDALNAEGSAAAYRWIPHRFAASQAIDWTPLWSLTEQ
KHKYVPTAICYYNYLLPPADRFCKADSNGNAAGNSLEEAILQGFMELVERDSVALWWYNRLRRP
EVELSSFEEPYFLQLQQFYRSQNRELWVLDLTADLGIPAFAGLSRRTVGSSERVSIGFGAHLDP
KIAILRALTEVSQVGLELDKVPDEKLDGESKDWMLEVTLETHPCLAPDPSQPRKTANDYPKRWS
DDIYTDVMACVEMAKVAGLETLVLDQTRPDIGLNVVKVMIPGMRTFWSRYGPGRLYDVPVQLGW
LKEPLAEAEMNPTNIPF*

FIG. 2D

NheI-LS-RS-GS35-PatD

MGHHHHHHHHHSSGHIEGRAS NKKNILPQQGQPVIRLTAGQLSSQLAELSEEALGDA GLEASG
GSGSGGGSGSGGGSGSGGGSGSGGGSGSGGGSGSGGGSGSGGGSGSGGGSGSGGGSGSGGGSG
GSGSSHMQPTALQIKPHFHVEIIEPKQVYLLGEQGNHALTGQLYCQILPFLNGEYTREQIVEKL
DGQVPEEYIDFVLSRLVEKGYLTEVAPELSLEVAAFWSELGIAPSVVAEGLKQPVTVTTAGKGI
REGIVANLAAALEEAGIQVSDPKAPKAPKAGDSTAQLQVVLTDDYLQPELAAINKEALERQQPW
LLVKPVGSILWLGPLFVPGETGCWHCLAQRLRGNREVEASVLQQKRALQERNGQNKNGAVSCLP
TARATLPSTLQTGLQWAATEIAKWMVKRHLNAIAPGTARFPTLAGKIFTFNQTTLELKAHPLSR
RPQCPTCGDQEILQERGFEPLKLESRPKHFTSDGGHRATTPEQTVQKYQHLIGPITGVVTELVR
ISDPANPLVHTYRAGHSFGSSAGSLRGLRNTLRYKSSGKGKTDSQSRASGLCEAIERYSGIFLG
DEPRKRATLAELGDLAIHPEQCLHFSDRQYDNEDALNAEGSAAAYRWIPHRFAASQAIDWTPLW
SLTEQKHKYVPTAICYYNYLLPEADRFCKADSNGNAAGNSLEEAILQGFMELVERDSVALWWYN
RLRRPEVELSSFEEPYELQLQQPYRSQNRELWVLDLTADLGIPAPAGLSRRTVGSSERVSIGPG
AHLDPKIAILRALTEVSQVGLELDKVPDEKLDGESKDWMLEVTLETHPCLAPDFSQPRKTANDY
PKRWSDDIYTDVMACVEMAKVAGLETLVLDQTRPDIGLNVVKVMIPGMRTFWSRYGPGRLYDVP
VQLGWLKEPLAEAEMNPTNIPF*

FIG. 2E

PatD-GS5-LS

MGHHHHHHHHHSSGHIEGRHMQPTALQIKPHFHVEIIEPKQVYLLGEQGNHALTGQLYCQILP
FLNGEYTREQIVEKLDGQVPEEYIDFVLSRLVEKGYLTEVAPELSLEVAAFWSELGIAPSVVAE
GLKQPVTVTTAGKGIREGIVANLAAALEEAGIQVSDPKAPKAPKAGDSTAQLQVVLTDDYLQPE
LAAINKEALERQQPWLLVKPVGSILWLGPLFVPGETGCWHCLAQRLRGNREVEASVLQQKRALQ
ERNGQNKNGAVSCLPTARATLPSTLQTGLQWAATEIAKWMVKRHLNAIAPGTARFPTLAGKIFT
FNQTTLELKAHPLSRRPQCPTCGDQEILQRRGFEPLKLESRPKHFTSDGGHRATTPEQTVQKYQ
HLIGPITGVVTELVRISDPANPLVHTYRAGHSFGSSAGSLRGLRNTLRYKSSGKGKTDSQSRAS
GLCEAIERYSGIFLGDEPRKRATLAELGDLAIHPEQCLHFSDRQYDNRDALNAEGSAAAYRWIP
HRFAASQAIDWTPLWSLTEQKHKYVPTAICYYNYLLPPADRFCKADSNGNAAGNSLEEAILQGF
MELVERDSVALWWYNRLRRPEVELSSFEEPYFLQLQQFYRSQNRELWVLDLTADLGIPAFAGLS
RRTVGSSERVSIGFGAHLDPKIAILRALTEVSQVGLELDKVPDEKLDGESKDWMLEVTLETHPC
LAPDPSQPRKTANDYPKRWSDDIYTDVMACVEMAKVAGLETLVLDQTRPDIGLNVVKVMIPGMR
TFWSRYGPGRLYDVPVQLGWLKEPLAEAEMNPTNIPFGSLEGSGSGSGSGNKKNILPQQGQPV
IRLTAGQLSSQLAELSEEALGDA*

PatD-GS15-LS

MGHHHHHHHHHSSGHIEGRHMQPTALQIKPHFHVEIIEPKQVYLLGEQGNHALTGQLYCQILP
FLNGEYTREQIVEKLDGQVPEEYIDFVLSRLVEKGYLTEVAPELSLEVAAFWSELGIAPSVVAE
GLKQPVTVTTAGKGIREGIVANLAAALEEAGIQVSDPKAPKAPKAGDSTAQLQVVLTDDYLQPE
LAAINKEALERQQPWLLVKPVGSILWLGPLFVPGETGCWHCLAQRLRGNREVEASVLQQKRALQ
ERNGQNKNGAVSCLPTARATLPSTLQTGLQWAATEIAKWMVKRHLNAIAPGTARFPTLAGKIFT
FNQTTLELKAHPLSRRPQCPTCGDQEILQRRGFEPLKLESRPKHFTSDGGHRATTPEQTVQKYQ
HLIGPITGVVTELVRISDPANPLVHTYRAGHSFGSSAGSLRGLRNTLRYKSSGKGKTDSQSRAS
GLCEAIERYSGIFLGDEPRKRATLAELGDLAIHPEQCLHFSDRQYDNRDALNAEGSAAAYRWIP
HRFAASQAIDWTPLWSLTEQKHKYVPTAICYYNYLLPPADRFCKADSNGNAAGNSLEEAILQGF
MELVERDSVALWWYNRLRRPEVELSSFEEPYFLQLQQFYRSQNRELWVLDLTADLGIPAFAGLS
RRTVGSSERVSIGFGAHLDPKIAILRALTEVSQVGLELDKVPDEKLDGESKDWMLEVTLETHPC
LAPDPSQPRKTANDYPKRWSDDIYTDVMACVEMAKVAGLETLVLDQTRPDIGLNVVKVMIPGMR
TFWSRYGPGRLYDVPVQLGWLKEPLAEAEMNPTNIPFGSLEGSGSGSGSGSGSGSGSGSGSGSGS
GSGSGNKKNILPQQGQPVIRLTAGQLSSQLAELSEEALGDA*

FIG. 2F

PatD-GS25-LS

MGHHHHHHHHHHSSGHIEGRHMQPTALQIKPHFHVEIIEPKQVYLLGEQGNHALTGQLYCQILP
FLNGEYTREQIVEKLDGQVPEEYIDFVLSRLVEKGYLTEVAPELSLEVAAFWSELGIAPSVVAE
GLKQPVTVTTAGKGIREGIVANLAAALEEAGIQVSDPKAPKAPKAGDSTAQLQVVLTDDYLQPE
LAAINKEALERQQPWLLVKPVGSILWLGPLFVPGETGCWHCLAQRLRGNREVEASVLQQKRALQ
ERNGQNKNGAVSCLPTARATLPSTLQTGLQWAATEIAKWMVKRHLNAIAPGTARFPTLAGKIFT
FNQTTLELKAHPLSRRPQCPTCGDQEILQRRGFEPLKLESRPKHFTSDGGHRATTPEQTVQKYQ
HLIGPITGVVTELVRISDPANPLVHTYRAGHSFGSSAGSLRGLRNTLRYKSSGKGKTDSQSRAS
GLCEAIERYSGIFLGDEPRKRATLAELGDLAIHPEQCLHFSDRQYDNRDALNAEGSAAAYRWIP
HRFAASQAIDWTPLWSLTEQKHKYVPTAICYYNYLLPPADRFCKADSNGNAAGNSLEEAILQGF
MELVERDSVALWWYNRLRRPEVELSSFEEPYFLQLQQFYRSQNRELWVLDLTADLGIPAFAGLS
RRTVGSSERVSIGFGAHLDPKIAILRALTEVSQVGLELDKVPDEKLDGESKDWMLEVTLETHPC
LAPDPSQPRKTANDYPKRWSDDIYTDVMACVEMAKVAGLETLVLDQTRPDIGLNVVKVMIPGMR
TFWSRYGPGRLYDVPVQLGWLKEPLAEAEMNPTNIPFGSLEGSGSGSGSGSGSGSGSGSGSGS
GSGSGSGSGSGSGSGSGSGSGSGSNKKNILPQQGQPVIRLTAGQLSSQLAELSEEALGDA*

PatD-GS35-LS

MGHHHHHHHHHHSSGHIEGRHMQPTALQIKPHFHVEIIEPKQVYLLGEQGNHALTGQLYCQILP
FLNGEYTREQIVEKLDGQVPEEYIDFVLSRLVEKGYLTEVAPELSLEVAAFWSELGIAPSVVAE
GLKQPVTVTTAGKGIREGIVANLAAALEEAGIQVSDPKAPKAPKAGDSTAQLQVVLTDDYLQPE
LAAINKEALERQQPWLLVKPVGSILWLGPLFVPGETGCWHCLAQRLRGNREVEASVLQQKRALQ
ERNGQNKNGAVSCLPTARATLPSTLQTGLQWAATEIAKWMVKRHLNAIAPGTARFPTLAGKIFT
FNQTTLELKAHPLSRRPQCPTCGDQEILQRRGFEPLKLESRPKHFTSDGGHRATTPEQTVQKYQ
HLIGPITGVVTELVRISDPANPLVHTYRAGHSFGSSAGSLRGLRNTLRYKSSGKGKTDSQSRAS
GLCEAIERYSGIFLGDEPRKRATLAELGDLAIHPEQCLHFSDRQYDNRDALNAEGSAAAYRWIP
HRFAASQAIDWTPLWSLTEQKHKYVPTAICYYNYLLPPADRFCKADSNGNAAGNSLEEAILQGF
MELVERDSVALWWYNRLRRPEVELSSFEEPYFLQLQQFYRSQNRELWVLDLTADLGIPAFAGLS
RRTVGSSERVSIGFGAHLDPKIAILRALTEVSQVGLELDKVPDEKLDGESKDWMLEVTLETHPC
LAPDPSQPRKTANDYPKRWSDDIYTDVMACVEMAKVAGLETLVLDQTRPDIGLNVVKVMIPGMR
TFWSRYGPGRLYDVPVQLGWLKEPLAEAEMNPTNIPFGSLEGSGSGSGSGSGSGSGSGSGSGS
GSGSGSGSGSGSGSGSGSGSGSGSGSGSGSGSGSGSNKKNILPQQGQPVIRLT
AGQLSSQLAELSEEALGDA*

| PofE mutants | | uRS | | CS | dRS | | | | | | | | | | CONDITION |
|---|---|---|---|---|---|---|---|---|---|---|---|---|---|---|---|
| st057 | M | G | | VTACITYFC | AXD | | | | | | | 3 | | | |
| st026 | M | G | | VTACITYFC | AXDGSG | | | | | | | 1 | | | |
| st119 | M | G | | ANICKANC | AXD | | | | | | | | 2 | | |
| st237 | M | G | | ANICKANC | AXDGSG | | | | | | | | 2 | | |
| st122 | M | G | | ANICAKAC | AXD | | | | | | | | 3 | | |
| st238 | M | G | | ANICAKAC | AXDGSG | | | | | | | | | | |
| st123 | M | G | | IRWCRNFC | AXD | | | | | | | | | 2 | |
| st229 | M | G | | IRWCRNFC | AXDGSG | | | | | | | | 1 | | |
| st173 | M | G | | IAICRII | AXD | | | | | | | | 1 | | |
| st240 | M | G | | IAICRII | AXDGSG | | | | | | | | | 1 | |
| st179 | M | G | | IIRCIAI | AXD | | | | | | | | | | |
| st241 | M | G | | IIRCIAI | AXDGSG | | | | | | | | | | |

| PrPc mutants HYDROPHOBIC | | | | CS | | GPS | | | | | | | | | CONDITION |
|---|---|---|---|---|---|---|---|---|---|---|---|---|---|---|
| st12 | M | G | AIICVALC | | AVD | | | | | | | 1 | | |
| st128 | M | G | AIICVALCVLAC | | AVD | | | | | | | | | |
| st130 | M | G | AIICVALCVLACIIVC | | AVD | | | | | | | | | ND |

Dap : diaminopropionic acid (b)

FIG. 5B-1

| PstI mutants | uRS | CS | dRS | | | | | | | | | | REMARK |
|---|---|---|---|---|---|---|---|---|---|---|---|---|---|
| sf75 | AmaP | RVRVCDYDL | WcnGG | | | | | | | | | | |
| sf76 | AmsF | RVRVCAADYDL | WcnGG | | | | | | | | | | |
| sf146 | AmaP | RVRVCAADYDL | WcnAYD | | | | | | | | | | |
| sf147 | AmsF | RVRVCACAADYDL | WcnAYD | | | | | | | | | | |
| sf148 | AmaP | RVRVCACAADYDL | WcnAYD | | | | | | | | | | |
| sf149 | AmsF | RVRVCACACAADYDL | WcnAYD | | | | | | | | | | |

FIG. 5B-2

HETEROCYCLASE PatD

SEQUENCE LISTING

```
<160> NUMBER OF SEQ ID NOS: 208

<210> SEQ ID NO 1
<211> LENGTH: 37
<212> TYPE: PRT
<213> ORGANISM: Artificial
<220> FEATURE:
<223> OTHER INFORMATION: Synthesized Peptide.

<400> SEQUENCE: 1

Met Asn Lys Lys Asn Ile Leu Pro Gln Gln Gly Gln Pro Val Ile Arg
1               5                   10                  15

Leu Thr Ala Gly Gln Leu Ser Ser Gln Leu Ala Glu Leu Ser Glu Glu
            20                  25                  30

Ala Leu Gly Asp Ala
        35

<210> SEQ ID NO 2
<211> LENGTH: 24
<212> TYPE: PRT
<213> ORGANISM: Artificial
<220> FEATURE:
<223> OTHER INFORMATION: Synthesized Peptide.

<400> SEQUENCE: 2

Met Lys Glu Gln Asn Ser Phe Asn Leu Leu Gln Glu Val Thr Glu Ser
1               5                   10                  15

Glu Leu Asp Leu Ile Leu Gly Ala
            20

<210> SEQ ID NO 3
<211> LENGTH: 25
<212> TYPE: PRT
<213> ORGANISM: Artificial
<220> FEATURE:
<223> OTHER INFORMATION: Synthesized Peptide.

<400> SEQUENCE: 3

Met Ile Leu Ala Ser Leu Ser Thr Phe Gln Gln Met Trp Ile Ser Lys
1               5                   10                  15

Gln Glu Tyr Asp Glu Ala Gly Asp Ala
            20                  25

<210> SEQ ID NO 4
<211> LENGTH: 37
<212> TYPE: PRT
<213> ORGANISM: Artificial
<220> FEATURE:
<223> OTHER INFORMATION: Synthesized Peptide.

<400> SEQUENCE: 4

Met Glu Leu Gln Leu Arg Pro Ser Gly Leu Glu Lys Lys Gln Ala Pro
```

-continued

```
                1               5                  10                 15
Ile Ser Glu Leu Asn Ile Ala Gln Thr Gln Gly Gly Asp Ser Gln Val
                20                 25                 30
Leu Ala Leu Asn Ala
        35

<210> SEQ ID NO 5
<211> LENGTH: 873
<212> TYPE: PRT
<213> ORGANISM: Artificial
<220> FEATURE:
<223> OTHER INFORMATION: Synthesized Peptide.

<400> SEQUENCE: 5

Met Gly His His His His His His His His Ser Ser Gly His
1               5                  10                 15

Ile Glu Gly Arg His Met Asn Lys Asn Ile Leu Pro Gln Gln Gly
                20                 25                 30

Gln Pro Val Ile Arg Leu Thr Ala Gly Gln Leu Ser Ser Gln Leu Ala
                35                 40                 45

Glu Leu Ser Glu Glu Ala Leu Gly Asp Ala Gly Ser Gly Ser Gly Ser
            50                 55                 60

Gly Ser Gly Ser Gly Ser Gly Ser Gly Ser Gly Ser Gly Ser Gly Ser
65                 70                 75                 80

Gly Ser Gly Ser Gly Ser Gly Ser His Met Gln Pro Thr Ala Leu Gln
                85                 90                 95

Ile Lys Pro His Phe His Val Glu Ile Glu Pro Lys Gln Val Tyr
            100                105                110

Leu Leu Gly Glu Gln Gly Asn His Ala Leu Thr Gly Gln Leu Tyr Cys
        115                120                125

Gln Ile Leu Pro Phe Leu Asn Gly Glu Tyr Thr Arg Glu Gln Ile Val
        130                135                140

Glu Lys Leu Asp Gly Gln Val Pro Glu Glu Tyr Ile Asp Phe Val Leu
145                150                155                160

Ser Arg Leu Val Glu Lys Gly Tyr Leu Thr Glu Val Ala Pro Glu Leu
                165                170                175

Ser Leu Glu Val Ala Ala Phe Trp Ser Glu Leu Gly Ile Ala Pro Ser
                180                185                190

Val Val Ala Glu Gly Leu Lys Gln Pro Val Thr Val Thr Ala Gly
            195                200                205

Lys Gly Ile Arg Glu Gly Ile Val Ala Asn Leu Ala Ala Ala Leu Glu
210                215                220

Glu Ala Gly Ile Gln Val Ser Asp Pro Lys Ala Pro Lys Ala Pro Lys
225                230                235                240

Ala Gly Asp Ser Thr Ala Gln Leu Gln Val Val Leu Thr Asp Asp Tyr
                245                250                255

Leu Gln Pro Glu Leu Ala Ala Ile Asn Lys Glu Ala Leu Glu Arg Gln
                260                265                270

Gln Pro Trp Leu Leu Val Lys Pro Val Gly Ser Ile Leu Trp Leu Gly
                275                280                285

Pro Leu Phe Val Pro Gly Glu Thr Gly Cys Trp His Cys Leu Ala Gln
                290                295                300

Arg Leu Arg Gly Asn Arg Glu Val Glu Ala Ser Val Leu Gln Gln Lys
305                310                315                320

Arg Ala Leu Gln Glu Arg Asn Gly Gln Asn Lys Asn Gly Ala Val Ser
```

-continued

```
                325                 330                 335
Cys Leu Pro Thr Ala Arg Ala Thr Leu Pro Ser Thr Leu Gln Thr Gly
                340                 345                 350
Leu Gln Trp Ala Ala Thr Glu Ile Ala Lys Trp Met Val Lys Arg His
                355                 360                 365
Leu Asn Ala Ile Ala Pro Gly Thr Ala Arg Phe Pro Thr Leu Ala Gly
                370                 375                 380
Lys Ile Phe Thr Phe Asn Gln Thr Thr Leu Glu Leu Lys Ala His Pro
385                 390                 395                 400
Leu Ser Arg Arg Pro Gln Cys Pro Thr Cys Gly Asp Gln Glu Ile Leu
                405                 410                 415
Gln Arg Arg Gly Phe Glu Pro Leu Lys Leu Glu Ser Arg Pro Lys His
                420                 425                 430
Phe Thr Ser Asp Gly Gly His Arg Ala Thr Thr Pro Glu Gln Thr Val
                435                 440                 445
Gln Lys Tyr Gln His Leu Ile Gly Pro Ile Thr Gly Val Val Thr Glu
                450                 455                 460
Leu Val Arg Ile Ser Asp Pro Ala Asn Pro Leu Val His Thr Tyr Arg
465                 470                 475                 480
Ala Gly His Ser Phe Gly Ser Ser Ala Gly Ser Leu Arg Gly Leu Arg
                485                 490                 495
Asn Thr Leu Arg Tyr Lys Ser Ser Gly Lys Gly Lys Thr Asp Ser Gln
                500                 505                 510
Ser Arg Ala Ser Gly Leu Cys Glu Ala Ile Glu Arg Tyr Ser Gly Ile
                515                 520                 525
Phe Leu Gly Asp Glu Pro Arg Lys Arg Ala Thr Leu Ala Glu Leu Gly
                530                 535                 540
Asp Leu Ala Ile His Pro Glu Gln Cys Leu His Phe Ser Asp Arg Gln
545                 550                 555                 560
Tyr Asp Asn Arg Asp Ala Leu Asn Ala Glu Gly Ser Ala Ala Ala Tyr
                565                 570                 575
Arg Trp Ile Pro His Arg Phe Ala Ala Ser Gln Ala Ile Asp Trp Thr
                580                 585                 590
Pro Leu Trp Ser Leu Thr Glu Gln Lys His Lys Tyr Val Pro Thr Ala
                595                 600                 605
Ile Cys Tyr Tyr Asn Tyr Leu Leu Pro Pro Ala Asp Arg Phe Cys Lys
                610                 615                 620
Ala Asp Ser Asn Gly Asn Ala Ala Gly Asn Ser Leu Glu Glu Ala Ile
625                 630                 635                 640
Leu Gln Gly Phe Met Glu Leu Val Glu Arg Asp Ser Val Ala Leu Trp
                645                 650                 655
Trp Tyr Asn Arg Leu Arg Arg Pro Glu Val Glu Leu Ser Ser Phe Glu
                660                 665                 670
Glu Pro Tyr Phe Leu Gln Leu Gln Gln Phe Tyr Arg Ser Gln Asn Arg
                675                 680                 685
Glu Leu Trp Val Leu Asp Leu Thr Ala Asp Leu Gly Ile Pro Ala Phe
                690                 695                 700
Ala Gly Leu Ser Arg Arg Thr Val Gly Ser Ser Glu Arg Val Ser Ile
705                 710                 715                 720
Gly Phe Gly Ala His Leu Asp Pro Lys Ile Ala Ile Leu Arg Ala Leu
                725                 730                 735
Thr Glu Val Ser Gln Val Gly Leu Glu Leu Asp Lys Val Pro Asp Glu
                740                 745                 750
```

-continued

```
Lys Leu Asp Gly Glu Ser Lys Asp Trp Met Leu Glu Val Thr Leu Glu
        755                 760                 765

Thr His Pro Cys Leu Ala Pro Asp Pro Ser Gln Pro Arg Lys Thr Ala
    770                 775                 780

Asn Asp Tyr Pro Lys Arg Trp Ser Asp Ile Tyr Thr Asp Val Met
785                 790                 795                 800

Ala Cys Val Glu Met Ala Lys Val Ala Gly Leu Glu Thr Leu Val Leu
                805                 810                 815

Asp Gln Thr Arg Pro Asp Ile Gly Leu Asn Val Val Lys Val Met Ile
                820                 825                 830

Pro Gly Met Arg Thr Phe Trp Ser Arg Tyr Pro Gly Arg Leu Tyr
                835                 840                 845

Asp Val Pro Val Gln Leu Gly Trp Leu Lys Glu Pro Leu Ala Glu Ala
        850                 855                 860

Glu Met Asn Pro Thr Asn Ile Pro Phe
865                 870

<210> SEQ ID NO 6
<211> LENGTH: 913
<212> TYPE: PRT
<213> ORGANISM: Artificial
<220> FEATURE:
<223> OTHER INFORMATION: Synthesized Peptide.

<400> SEQUENCE: 6

Met Gly His His His His His His His His Ser Ser Gly His
1               5                   10                  15

Ile Glu Gly Arg His Met Asn Lys Lys Asn Ile Leu Pro Gln Gln Gly
                20                  25                  30

Gln Pro Val Ile Arg Leu Thr Ala Gly Gln Leu Ser Ser Gln Leu Ala
            35                  40                  45

Glu Leu Ser Glu Glu Ala Leu Gly Asp Ala Gly Ser Gly Ser Gly Ser
        50                  55                  60

Gly Ser Gly Ser Gly Ser Gly Ser Gly Ser Gly Ser Gly Ser Gly Ser
65                  70                  75                  80

Gly Ser Gly Ser Gly Ser Gly Ser Gly Ser Gly Ser Gly Ser Gly Ser
                85                  90                  95

Gly Ser Gly Ser Gly Ser Gly Ser Gly Ser Gly Ser Gly Ser Gly Ser
            100                 105                 110

Gly Ser Gly Ser Gly Ser Gly Ser Gly Ser Gly Ser Gly Ser Gly Ser
        115                 120                 125

His Met Gln Pro Thr Ala Leu Gln Ile Lys Pro His Phe His Val Glu
    130                 135                 140

Ile Ile Glu Pro Lys Gln Val Tyr Leu Leu Gly Glu Gln Gly Asn His
145                 150                 155                 160

Ala Leu Thr Gly Gln Leu Tyr Cys Gln Ile Leu Pro Phe Leu Asn Gly
                165                 170                 175

Glu Tyr Thr Arg Glu Gln Ile Val Glu Lys Leu Asp Gly Gln Val Pro
            180                 185                 190

Glu Glu Tyr Ile Asp Phe Val Leu Ser Arg Leu Val Glu Lys Gly Tyr
        195                 200                 205

Leu Thr Glu Val Ala Pro Glu Leu Ser Leu Glu Val Ala Ala Phe Trp
    210                 215                 220

Ser Glu Leu Gly Ile Ala Pro Ser Val Val Ala Glu Gly Leu Lys Gln
225                 230                 235                 240
```

```
Pro Val Thr Val Thr Ala Gly Lys Gly Ile Arg Glu Gly Ile Val
            245                 250                 255

Ala Asn Leu Ala Ala Leu Glu Glu Ala Gly Ile Gln Val Ser Asp
            260                 265                 270

Pro Lys Ala Pro Lys Ala Pro Lys Ala Gly Asp Ser Thr Ala Gln Leu
            275                 280                 285

Gln Val Val Leu Thr Asp Asp Tyr Leu Gln Pro Glu Leu Ala Ala Ile
            290                 295                 300

Asn Lys Glu Ala Leu Glu Arg Gln Gln Pro Trp Leu Leu Val Lys Pro
305                 310                 315                 320

Val Gly Ser Ile Leu Trp Leu Gly Pro Leu Phe Val Pro Gly Glu Thr
            325                 330                 335

Gly Cys Trp His Cys Leu Ala Gln Arg Leu Arg Gly Asn Arg Glu Val
            340                 345                 350

Glu Ala Ser Val Leu Gln Gln Lys Arg Ala Leu Gln Glu Arg Asn Gly
            355                 360                 365

Gln Asn Lys Asn Gly Ala Val Ser Cys Leu Pro Thr Ala Arg Ala Thr
            370                 375                 380

Leu Pro Ser Thr Leu Gln Thr Gly Leu Gln Trp Ala Ala Thr Glu Ile
385                 390                 395                 400

Ala Lys Trp Met Val Lys Arg His Leu Asn Ala Ile Ala Pro Gly Thr
            405                 410                 415

Ala Arg Phe Pro Thr Leu Ala Gly Lys Ile Phe Thr Phe Asn Gln Thr
            420                 425                 430

Thr Leu Glu Leu Lys Ala His Pro Leu Ser Arg Arg Pro Gln Cys Pro
            435                 440                 445

Thr Cys Gly Asp Gln Glu Ile Leu Gln Arg Arg Gly Phe Glu Pro Leu
            450                 455                 460

Lys Leu Glu Ser Arg Pro Lys His Phe Thr Ser Asp Gly His Arg
465                 470                 475                 480

Ala Thr Thr Pro Glu Gln Thr Val Gln Lys Tyr Gln His Leu Ile Gly
            485                 490                 495

Pro Ile Thr Gly Val Val Thr Glu Leu Val Arg Ile Ser Asp Pro Ala
            500                 505                 510

Asn Pro Leu Val His Thr Tyr Arg Ala Gly His Ser Phe Gly Ser Ser
            515                 520                 525

Ala Gly Ser Leu Arg Gly Leu Arg Asn Thr Leu Arg Tyr Lys Ser Ser
            530                 535                 540

Gly Lys Gly Lys Thr Asp Ser Gln Ser Arg Ala Ser Gly Leu Cys Glu
545                 550                 555                 560

Ala Ile Glu Arg Tyr Ser Gly Ile Phe Leu Gly Asp Glu Pro Arg Lys
            565                 570                 575

Arg Ala Thr Leu Ala Glu Leu Gly Asp Leu Ala Ile His Pro Glu Gln
            580                 585                 590

Cys Leu His Phe Ser Asp Arg Gln Tyr Asp Asn Arg Asp Ala Leu Asn
            595                 600                 605

Ala Glu Gly Ser Ala Ala Ala Tyr Arg Trp Ile Pro His Arg Phe Ala
            610                 615                 620

Ala Ser Gln Ala Ile Asp Trp Thr Pro Leu Trp Ser Leu Thr Glu Gln
625                 630                 635                 640

Lys His Lys Tyr Val Pro Thr Ala Ile Cys Tyr Tyr Asn Tyr Leu Leu
            645                 650                 655
```

```
Pro Pro Ala Asp Arg Phe Cys Lys Ala Asp Ser Asn Gly Asn Ala Ala
            660                 665                 670

Gly Asn Ser Leu Glu Glu Ala Ile Leu Gln Gly Phe Met Glu Leu Val
        675                 680                 685

Glu Arg Asp Ser Val Ala Leu Trp Trp Tyr Asn Arg Leu Arg Arg Pro
    690                 695                 700

Glu Val Glu Leu Ser Ser Phe Glu Glu Pro Tyr Phe Leu Gln Leu Gln
705                 710                 715                 720

Gln Phe Tyr Arg Ser Gln Asn Arg Glu Leu Trp Val Leu Asp Leu Thr
                725                 730                 735

Ala Asp Leu Gly Ile Pro Ala Phe Ala Gly Leu Ser Arg Arg Thr Val
            740                 745                 750

Gly Ser Ser Glu Arg Val Ser Ile Gly Phe Gly Ala His Leu Asp Pro
        755                 760                 765

Lys Ile Ala Ile Leu Arg Ala Leu Thr Glu Val Ser Gln Val Gly Leu
    770                 775                 780

Glu Leu Asp Lys Val Pro Asp Glu Lys Leu Asp Gly Glu Ser Lys Asp
785                 790                 795                 800

Trp Met Leu Glu Val Thr Leu Glu Thr His Pro Cys Leu Ala Pro Asp
                805                 810                 815

Pro Ser Gln Pro Arg Lys Thr Ala Asn Asp Tyr Pro Lys Arg Trp Ser
            820                 825                 830

Asp Asp Ile Tyr Thr Asp Val Met Ala Cys Val Glu Met Ala Lys Val
        835                 840                 845

Ala Gly Leu Glu Thr Leu Val Leu Asp Gln Thr Arg Pro Asp Ile Gly
    850                 855                 860

Leu Asn Val Val Lys Val Met Ile Pro Gly Met Arg Thr Phe Trp Ser
865                 870                 875                 880

Arg Tyr Gly Pro Gly Arg Leu Tyr Asp Val Pro Val Gln Leu Gly Trp
                885                 890                 895

Leu Lys Glu Pro Leu Ala Glu Ala Glu Met Asn Pro Thr Asn Ile Pro
            900                 905                 910

Phe

<210> SEQ ID NO 7
<211> LENGTH: 853
<212> TYPE: PRT
<213> ORGANISM: Artificial
<220> FEATURE:
<223> OTHER INFORMATION: Synthesized Peptide.

<400> SEQUENCE: 7

Met Gly His His His His His His His His Ser Ser Gly His
1               5                   10                  15

Ile Glu Gly Arg Ala Ser Asn Lys Lys Asn Ile Leu Pro Gln Gln Gly
                20                  25                  30

Gln Pro Val Ile Arg Leu Thr Ala Gly Gln Leu Ser Ser Gln Leu Ala
            35                  40                  45

Glu Leu Ser Glu Glu Ala Leu Gly Asp Ala Gly Ser Gly Ser Gly Ser
        50                  55                  60

Gly Ser Gly Ser His Met Gln Pro Thr Ala Leu Gln Ile Lys Pro His
65                  70                  75                  80

Phe His Val Glu Ile Ile Glu Pro Lys Gln Val Tyr Leu Leu Gly Glu
                85                  90                  95

Gln Gly Asn His Ala Leu Thr Gly Gln Leu Tyr Cys Gln Ile Leu Pro
```

```
                100                 105                 110
Phe Leu Asn Gly Glu Tyr Thr Arg Glu Gln Ile Val Glu Lys Leu Asp
            115                 120                 125

Gly Gln Val Pro Glu Glu Tyr Ile Asp Phe Val Leu Ser Arg Leu Val
            130                 135                 140

Glu Lys Gly Tyr Leu Thr Glu Val Ala Pro Glu Leu Ser Leu Glu Val
145                 150                 155                 160

Ala Ala Phe Trp Ser Glu Leu Gly Ile Ala Pro Ser Val Val Ala Glu
                165                 170                 175

Gly Leu Lys Gln Pro Val Thr Val Thr Thr Ala Gly Lys Gly Ile Arg
            180                 185                 190

Glu Gly Ile Val Ala Asn Leu Ala Ala Leu Glu Glu Ala Gly Ile
            195                 200                 205

Gln Val Ser Asp Pro Lys Ala Pro Lys Ala Pro Lys Ala Gly Asp Ser
            210                 215                 220

Thr Ala Gln Leu Gln Val Val Leu Thr Asp Asp Tyr Leu Gln Pro Glu
225                 230                 235                 240

Leu Ala Ala Ile Asn Lys Glu Ala Leu Glu Arg Gln Gln Pro Trp Leu
                245                 250                 255

Leu Val Lys Pro Val Gly Ser Ile Leu Trp Leu Gly Pro Leu Phe Val
                260                 265                 270

Pro Gly Glu Thr Gly Cys Trp His Cys Leu Ala Gln Arg Leu Arg Gly
            275                 280                 285

Asn Arg Glu Val Glu Ala Ser Val Leu Gln Gln Lys Arg Ala Leu Gln
290                 295                 300

Glu Arg Asn Gly Gln Asn Lys Asn Gly Ala Val Ser Cys Leu Pro Thr
305                 310                 315                 320

Ala Arg Ala Thr Leu Pro Ser Thr Leu Gln Thr Gly Leu Gln Trp Ala
                325                 330                 335

Ala Thr Glu Ile Ala Lys Trp Met Val Lys Arg His Leu Asn Ala Ile
            340                 345                 350

Ala Pro Gly Thr Ala Arg Phe Pro Thr Leu Ala Gly Lys Ile Phe Thr
            355                 360                 365

Phe Asn Gln Thr Thr Leu Glu Leu Lys Ala His Pro Leu Ser Arg Arg
370                 375                 380

Pro Gln Cys Pro Thr Cys Gly Asp Gln Glu Ile Leu Gln Arg Arg Gly
385                 390                 395                 400

Phe Glu Pro Leu Lys Leu Glu Ser Arg Pro Lys His Phe Thr Ser Asp
                405                 410                 415

Gly Gly His Arg Ala Thr Thr Pro Glu Gln Thr Val Gln Lys Tyr Gln
            420                 425                 430

His Leu Ile Gly Pro Ile Thr Gly Val Val Thr Glu Leu Val Arg Ile
            435                 440                 445

Ser Asp Pro Ala Asn Pro Leu Val His Thr Tyr Arg Ala Gly His Ser
450                 455                 460

Phe Gly Ser Ser Ala Gly Ser Leu Arg Gly Leu Arg Asn Thr Leu Arg
465                 470                 475                 480

Tyr Lys Ser Ser Gly Lys Gly Lys Thr Asp Ser Gln Ser Arg Ala Ser
                485                 490                 495

Gly Leu Cys Glu Ala Ile Glu Arg Tyr Ser Gly Ile Phe Leu Gly Asp
            500                 505                 510

Glu Pro Arg Lys Arg Ala Thr Leu Ala Glu Leu Gly Asp Leu Ala Ile
            515                 520                 525
```

His Pro Glu Gln Cys Leu His Phe Ser Asp Arg Gln Tyr Asp Asn Arg
530                 535                 540

Asp Ala Leu Asn Ala Glu Gly Ser Ala Ala Tyr Arg Trp Ile Pro
545                 550                 555                 560

His Arg Phe Ala Ala Ser Gln Ala Ile Asp Trp Thr Pro Leu Trp Ser
            565                 570                 575

Leu Thr Glu Gln Lys His Lys Tyr Val Pro Thr Ala Ile Cys Tyr Tyr
            580                 585                 590

Asn Tyr Leu Leu Pro Pro Ala Asp Arg Phe Cys Lys Ala Asp Ser Asn
        595                 600                 605

Gly Asn Ala Ala Gly Asn Ser Leu Glu Glu Ala Ile Leu Gln Gly Phe
        610                 615                 620

Met Glu Leu Val Glu Arg Asp Ser Val Ala Leu Trp Trp Tyr Asn Arg
625                 630                 635                 640

Leu Arg Arg Pro Glu Val Glu Leu Ser Ser Phe Glu Pro Tyr Phe
                645                 650                 655

Leu Gln Leu Gln Gln Phe Tyr Arg Ser Gln Asn Arg Glu Leu Trp Val
            660                 665                 670

Leu Asp Leu Thr Ala Asp Leu Gly Ile Pro Ala Phe Ala Gly Leu Ser
        675                 680                 685

Arg Arg Thr Val Gly Ser Ser Glu Arg Val Ser Ile Gly Phe Gly Ala
690                 695                 700

His Leu Asp Pro Lys Ile Ala Ile Leu Arg Ala Leu Thr Glu Val Ser
705                 710                 715                 720

Gln Val Gly Leu Glu Leu Asp Lys Val Pro Asp Glu Lys Leu Asp Gly
            725                 730                 735

Glu Ser Lys Asp Trp Met Leu Val Thr Leu Glu Thr His Pro Cys
            740                 745                 750

Leu Ala Pro Asp Pro Ser Gln Pro Arg Lys Thr Ala Asn Asp Tyr Pro
        755                 760                 765

Lys Arg Trp Ser Asp Asp Ile Tyr Thr Asp Val Met Ala Cys Val Glu
        770                 775                 780

Met Ala Lys Val Ala Gly Leu Glu Thr Leu Val Leu Asp Gln Thr Arg
785                 790                 795                 800

Pro Asp Ile Gly Leu Asn Val Val Lys Val Met Ile Pro Gly Met Arg
            805                 810                 815

Thr Phe Trp Ser Arg Tyr Gly Pro Gly Arg Leu Tyr Asp Val Pro Val
            820                 825                 830

Gln Leu Gly Trp Leu Lys Glu Pro Leu Ala Glu Ala Glu Met Asn Pro
        835                 840                 845

Thr Asn Ile Pro Phe
    850

<210> SEQ ID NO 8
<211> LENGTH: 873
<212> TYPE: PRT
<213> ORGANISM: Artificial
<220> FEATURE:
<223> OTHER INFORMATION: Synthesized Peptide.

<400> SEQUENCE: 8

Met Gly His His His His His His His His Ser Ser Gly His
1               5                   10                  15

Ile Glu Gly Arg Ala Ser Asn Lys Lys Asn Ile Leu Pro Gln Gln Gly
                20                  25                  30

```
Gln Pro Val Ile Arg Leu Thr Ala Gly Gln Leu Ser Gln Leu Ala
            35                  40                  45
Glu Leu Ser Glu Glu Ala Leu Gly Asp Ala Gly Ser Gly Ser Gly Ser
 50                  55                  60
Gly Ser Gly Ser Gly Ser Gly Ser Gly Ser Gly Ser Gly Ser Gly Ser
 65                  70                  75                  80
Gly Ser Gly Ser Gly Ser Ser His Met Gln Pro Thr Ala Leu Gln
                    85                  90                  95
Ile Lys Pro His Phe His Val Glu Ile Glu Pro Lys Gln Val Tyr
                100                 105                 110
Leu Leu Gly Glu Gln Gly Asn His Ala Leu Thr Gly Gln Leu Tyr Cys
            115                 120                 125
Gln Ile Leu Pro Phe Leu Asn Gly Glu Tyr Thr Arg Glu Gln Ile Val
            130                 135                 140
Glu Lys Leu Asp Gly Gln Val Pro Glu Glu Tyr Ile Asp Phe Val Leu
145                 150                 155                 160
Ser Arg Leu Val Glu Lys Gly Tyr Leu Thr Glu Val Ala Pro Glu Leu
                165                 170                 175
Ser Leu Glu Val Ala Ala Phe Trp Ser Glu Leu Gly Ile Ala Pro Ser
            180                 185                 190
Val Val Ala Glu Gly Leu Lys Gln Pro Val Thr Val Thr Thr Ala Gly
            195                 200                 205
Lys Gly Ile Arg Glu Gly Ile Val Ala Asn Leu Ala Ala Ala Leu Glu
210                 215                 220
Glu Ala Gly Ile Gln Val Ser Asp Pro Lys Ala Pro Lys Ala Pro Lys
225                 230                 235                 240
Ala Gly Asp Ser Thr Ala Gln Leu Gln Val Val Leu Thr Asp Asp Tyr
                245                 250                 255
Leu Gln Pro Glu Leu Ala Ala Ile Asn Lys Glu Ala Leu Glu Arg Gln
            260                 265                 270
Gln Pro Trp Leu Leu Val Lys Pro Val Gly Ser Ile Leu Trp Leu Gly
            275                 280                 285
Pro Leu Phe Val Pro Gly Glu Thr Gly Cys Trp His Cys Leu Ala Gln
            290                 295                 300
Arg Leu Arg Gly Asn Arg Glu Val Glu Ala Ser Val Leu Gln Gln Lys
305                 310                 315                 320
Arg Ala Leu Gln Glu Arg Asn Gly Gln Asn Lys Asn Gly Ala Val Ser
                325                 330                 335
Cys Leu Pro Thr Ala Arg Ala Thr Leu Pro Ser Thr Leu Gln Thr Gly
            340                 345                 350
Leu Gln Trp Ala Ala Thr Glu Ile Ala Lys Trp Met Val Lys Arg His
            355                 360                 365
Leu Asn Ala Ile Ala Pro Gly Thr Ala Arg Phe Pro Thr Leu Ala Gly
            370                 375                 380
Lys Ile Phe Thr Phe Asn Gln Thr Thr Leu Glu Leu Lys Ala His Pro
385                 390                 395                 400
Leu Ser Arg Arg Pro Gln Cys Pro Thr Cys Gly Asp Gln Glu Ile Leu
                405                 410                 415
Gln Arg Arg Gly Phe Glu Pro Leu Lys Leu Glu Ser Arg Pro Lys His
            420                 425                 430
Phe Thr Ser Asp Gly Gly His Arg Ala Thr Thr Pro Glu Gln Thr Val
            435                 440                 445
```

-continued

```
Gln Lys Tyr Gln His Leu Ile Gly Pro Ile Thr Gly Val Val Thr Glu
450                 455                 460

Leu Val Arg Ile Ser Asp Pro Ala Asn Pro Leu Val His Thr Tyr Arg
465                 470                 475                 480

Ala Gly His Ser Phe Gly Ser Ser Ala Gly Ser Leu Arg Gly Leu Arg
                485                 490                 495

Asn Thr Leu Arg Tyr Lys Ser Ser Gly Lys Gly Lys Thr Asp Ser Gln
                500                 505                 510

Ser Arg Ala Ser Gly Leu Cys Glu Ala Ile Glu Arg Tyr Ser Gly Ile
            515                 520                 525

Phe Leu Gly Asp Glu Pro Arg Lys Arg Ala Thr Leu Ala Glu Leu Gly
530                 535                 540

Asp Leu Ala Ile His Pro Glu Gln Cys Leu His Phe Ser Asp Arg Gln
545                 550                 555                 560

Tyr Asp Asn Arg Asp Ala Leu Asn Ala Glu Gly Ser Ala Ala Ala Tyr
                565                 570                 575

Arg Trp Ile Pro His Arg Phe Ala Ala Ser Gln Ala Ile Asp Trp Thr
                580                 585                 590

Pro Leu Trp Ser Leu Thr Glu Gln Lys His Lys Tyr Val Pro Thr Ala
            595                 600                 605

Ile Cys Tyr Tyr Asn Tyr Leu Leu Pro Pro Ala Asp Arg Phe Cys Lys
610                 615                 620

Ala Asp Ser Asn Gly Asn Ala Ala Gly Asn Ser Leu Glu Glu Ala Ile
625                 630                 635                 640

Leu Gln Gly Phe Met Glu Leu Val Glu Arg Asp Ser Val Ala Leu Trp
                645                 650                 655

Trp Tyr Asn Arg Leu Arg Arg Pro Glu Val Glu Leu Ser Ser Phe Glu
                660                 665                 670

Glu Pro Tyr Phe Leu Gln Leu Gln Gln Phe Tyr Arg Ser Gln Asn Arg
            675                 680                 685

Glu Leu Trp Val Leu Asp Leu Thr Ala Asp Leu Gly Ile Pro Ala Phe
690                 695                 700

Ala Gly Leu Ser Arg Arg Thr Val Gly Ser Ser Glu Arg Val Ser Ile
705                 710                 715                 720

Gly Phe Gly Ala His Leu Asp Pro Lys Ile Ala Ile Leu Arg Ala Leu
                725                 730                 735

Thr Glu Val Ser Gln Val Gly Leu Glu Leu Asp Lys Val Pro Asp Glu
                740                 745                 750

Lys Leu Asp Gly Glu Ser Lys Asp Trp Met Leu Glu Val Thr Leu Glu
            755                 760                 765

Thr His Pro Cys Leu Ala Pro Asp Pro Ser Gln Pro Arg Lys Thr Ala
770                 775                 780

Asn Asp Tyr Pro Lys Arg Trp Ser Asp Asp Ile Tyr Thr Asp Val Met
785                 790                 795                 800

Ala Cys Val Glu Met Ala Lys Val Ala Gly Leu Glu Thr Leu Val Leu
                805                 810                 815

Asp Gln Thr Arg Pro Asp Ile Gly Leu Asn Val Val Lys Val Met Ile
                820                 825                 830

Pro Gly Met Arg Thr Phe Trp Ser Arg Tyr Gly Pro Gly Arg Leu Tyr
            835                 840                 845

Asp Val Pro Val Gln Leu Gly Trp Leu Lys Glu Pro Leu Ala Glu Ala
850                 855                 860

Glu Met Asn Pro Thr Asn Ile Pro Phe
```

865 870

<210> SEQ ID NO 9
<211> LENGTH: 893
<212> TYPE: PRT
<213> ORGANISM: Artificial
<220> FEATURE:
<223> OTHER INFORMATION: Synthesized Peptide.

<400> SEQUENCE: 9

```
Met Gly His His His His His His His His Ser Ser Gly His
1               5                   10                  15

Ile Glu Gly Arg Ala Ser Asn Lys Lys Asn Ile Leu Pro Gln Gln Gly
                20                  25                  30

Gln Pro Val Ile Arg Leu Thr Ala Gly Gln Leu Ser Ser Gln Leu Ala
            35                  40                  45

Glu Leu Ser Glu Glu Ala Leu Gly Asp Ala Gly Ser Gly Ser Gly Ser
        50                  55                  60

Gly Ser Gly Ser Gly Ser Gly Ser Gly Ser Gly Ser Gly Ser Gly Ser
65              70                  75                  80

Gly Ser Gly Ser Gly Ser Gly Ser Gly Ser Gly Ser Gly Ser Gly Ser
                85                  90                  95

Gly Ser Gly Ser Gly Ser Gly Ser Gly Ser His Met Gln Pro
            100                 105                 110

Thr Ala Leu Gln Ile Lys Pro His Phe His Val Glu Ile Glu Pro
        115                 120                 125

Lys Gln Val Tyr Leu Leu Gly Glu Gln Gly Asn His Ala Leu Thr Gly
    130                 135                 140

Gln Leu Tyr Cys Gln Ile Leu Pro Phe Leu Asn Gly Glu Tyr Thr Arg
145                 150                 155                 160

Glu Gln Ile Val Glu Lys Leu Asp Gly Gln Val Pro Glu Glu Tyr Ile
                165                 170                 175

Asp Phe Val Leu Ser Arg Leu Val Glu Lys Gly Tyr Leu Thr Glu Val
            180                 185                 190

Ala Pro Glu Leu Ser Leu Glu Val Ala Ala Phe Trp Ser Glu Leu Gly
        195                 200                 205

Ile Ala Pro Ser Val Val Ala Glu Gly Leu Lys Gln Pro Val Thr Val
    210                 215                 220

Thr Thr Ala Gly Lys Gly Ile Arg Glu Gly Ile Val Ala Asn Leu Ala
225                 230                 235                 240

Ala Leu Glu Glu Ala Gly Ile Gln Val Ser Asp Pro Lys Ala Pro
                245                 250                 255

Lys Ala Pro Lys Ala Gly Asp Ser Thr Ala Gln Leu Gln Val Val Leu
            260                 265                 270

Thr Asp Asp Tyr Leu Gln Pro Glu Leu Ala Ala Ile Asn Lys Glu Ala
        275                 280                 285

Leu Glu Arg Gln Gln Pro Trp Leu Leu Val Lys Pro Val Gly Ser Ile
    290                 295                 300

Leu Trp Leu Gly Pro Leu Phe Val Pro Gly Glu Thr Gly Cys Trp His
305                 310                 315                 320

Cys Leu Ala Gln Arg Leu Arg Gly Asn Arg Glu Val Glu Ala Ser Val
                325                 330                 335

Leu Gln Gln Lys Arg Ala Leu Gln Glu Arg Asn Gly Gln Asn Lys Asn
            340                 345                 350

Gly Ala Val Ser Cys Leu Pro Thr Ala Arg Ala Thr Leu Pro Ser Thr
```

```
                355                 360                 365
Leu Gln Thr Gly Leu Gln Trp Ala Ala Thr Glu Ile Ala Lys Trp Met
370                 375                 380

Val Lys Arg His Leu Asn Ala Ile Ala Pro Gly Thr Ala Arg Phe Pro
385                 390                 395                 400

Thr Leu Ala Gly Lys Ile Phe Thr Phe Asn Gln Thr Thr Leu Glu Leu
                405                 410                 415

Lys Ala His Pro Leu Ser Arg Arg Pro Gln Cys Pro Thr Cys Gly Asp
                420                 425                 430

Gln Glu Ile Leu Gln Arg Arg Gly Phe Glu Pro Leu Lys Leu Glu Ser
                435                 440                 445

Arg Pro Lys His Phe Thr Ser Asp Gly Gly His Arg Ala Thr Thr Pro
                450                 455                 460

Glu Gln Thr Val Gln Lys Tyr Gln His Leu Ile Gly Pro Ile Thr Gly
465                 470                 475                 480

Val Val Thr Glu Leu Val Arg Ile Ser Asp Pro Ala Asn Pro Leu Val
                485                 490                 495

His Thr Tyr Arg Ala Gly His Ser Phe Gly Ser Ser Ala Gly Ser Leu
                500                 505                 510

Arg Gly Leu Arg Asn Thr Leu Arg Tyr Lys Ser Ser Lys Gly Lys
                515                 520                 525

Thr Asp Ser Gln Ser Arg Ala Ser Gly Leu Cys Glu Ala Ile Glu Arg
530                 535                 540

Tyr Ser Gly Ile Phe Leu Gly Asp Glu Pro Arg Lys Arg Ala Thr Leu
545                 550                 555                 560

Ala Glu Leu Gly Asp Leu Ala Ile His Pro Glu Gln Cys Leu His Phe
                565                 570                 575

Ser Asp Arg Gln Tyr Asp Asn Arg Asp Ala Leu Asn Ala Glu Gly Ser
                580                 585                 590

Ala Ala Ala Tyr Arg Trp Ile Pro His Arg Phe Ala Ala Ser Gln Ala
                595                 600                 605

Ile Asp Trp Thr Pro Leu Trp Ser Leu Thr Glu Gln Lys His Lys Tyr
610                 615                 620

Val Pro Thr Ala Ile Cys Tyr Tyr Asn Tyr Leu Leu Pro Pro Ala Asp
625                 630                 635                 640

Arg Phe Cys Lys Ala Asp Ser Asn Gly Asn Ala Ala Gly Asn Ser Leu
                645                 650                 655

Glu Glu Ala Ile Leu Gln Gly Phe Met Glu Leu Val Glu Arg Asp Ser
                660                 665                 670

Val Ala Leu Trp Trp Tyr Asn Arg Leu Arg Arg Pro Glu Val Glu Leu
                675                 680                 685

Ser Ser Phe Glu Glu Pro Tyr Phe Leu Gln Leu Gln Gln Phe Tyr Arg
                690                 695                 700

Ser Gln Asn Arg Glu Leu Trp Val Leu Asp Leu Thr Ala Asp Leu Gly
705                 710                 715                 720

Ile Pro Ala Phe Ala Gly Leu Ser Arg Arg Thr Val Gly Ser Ser Glu
                725                 730                 735

Arg Val Ser Ile Gly Phe Gly Ala His Leu Asp Pro Lys Ile Ala Ile
                740                 745                 750

Leu Arg Ala Leu Thr Glu Val Ser Gln Val Gly Leu Glu Leu Asp Lys
                755                 760                 765

Val Pro Asp Glu Lys Leu Asp Gly Glu Ser Lys Asp Trp Met Leu Glu
770                 775                 780
```

```
Val Thr Leu Glu Thr His Pro Cys Leu Ala Pro Asp Pro Ser Gln Pro
785                 790                 795                 800

Arg Lys Thr Ala Asn Asp Tyr Pro Lys Arg Trp Ser Asp Ile Tyr
            805                 810                 815

Thr Asp Val Met Ala Cys Val Glu Met Ala Lys Val Ala Gly Leu Glu
            820                 825                 830

Thr Leu Val Leu Asp Gln Thr Arg Pro Asp Ile Gly Leu Asn Val Val
            835                 840                 845

Lys Val Met Ile Pro Gly Met Arg Thr Phe Trp Ser Arg Tyr Gly Pro
            850                 855                 860

Gly Arg Leu Tyr Asp Val Pro Val Gln Leu Gly Trp Leu Lys Glu Pro
865                 870                 875                 880

Leu Ala Glu Ala Glu Met Asn Pro Thr Asn Ile Pro Phe
                    885                 890
```

<210> SEQ ID NO 10  
<211> LENGTH: 913  
<212> TYPE: PRT  
<213> ORGANISM: Artificial  
<220> FEATURE:  
<223> OTHER INFORMATION: Synthesized Peptide.

<400> SEQUENCE: 10

```
Met Gly His His His His His His His His Ser Ser Gly His
1               5                   10                  15

Ile Glu Gly Arg Ala Ser Asn Lys Lys Asn Ile Leu Pro Gln Gln Gly
                20                  25                  30

Gln Pro Val Ile Arg Leu Thr Ala Gly Gln Leu Ser Ser Gln Leu Ala
            35                  40                  45

Glu Leu Ser Glu Glu Ala Leu Gly Asp Ala Gly Ser Gly Ser Gly Ser
    50                  55                  60

Gly Ser Gly Ser Gly Ser Gly Ser Gly Ser Gly Ser Gly Ser Gly Ser
65                  70                  75                  80

Gly Ser Gly Ser Gly Ser Gly Ser Gly Ser Gly Ser Gly Ser Gly Ser
                85                  90                  95

Gly Ser Gly Ser Gly Ser Gly Ser Gly Ser Gly Ser Gly Ser Gly Ser
            100                 105                 110

Gly Ser Gly Ser Gly Ser Gly Ser Gly Ser Gly Ser Gly Ser Gly Ser
        115                 120                 125

His Met Gln Pro Thr Ala Leu Gln Ile Lys Pro His Phe His Val Glu
    130                 135                 140

Ile Ile Glu Pro Lys Gln Val Tyr Leu Leu Gly Glu Gln Gly Asn His
145                 150                 155                 160

Ala Leu Thr Gly Gln Leu Tyr Cys Gln Ile Leu Pro Phe Leu Asn Gly
                165                 170                 175

Glu Tyr Thr Arg Glu Gln Ile Val Glu Lys Leu Asp Gly Gln Val Pro
            180                 185                 190

Glu Glu Tyr Ile Asp Phe Val Leu Ser Arg Leu Val Glu Lys Gly Tyr
        195                 200                 205

Leu Thr Glu Val Ala Pro Glu Leu Ser Leu Glu Val Ala Ala Phe Trp
    210                 215                 220

Ser Glu Leu Gly Ile Ala Pro Ser Val Ala Glu Gly Leu Lys Gln
225                 230                 235                 240

Pro Val Thr Val Thr Thr Ala Gly Lys Gly Ile Arg Glu Gly Ile Val
                245                 250                 255
```

```
Ala Asn Leu Ala Ala Leu Glu Glu Ala Gly Ile Gln Val Ser Asp
            260                 265                 270

Pro Lys Ala Pro Lys Ala Pro Lys Ala Gly Asp Ser Thr Ala Gln Leu
275                 280                 285

Gln Val Val Leu Thr Asp Asp Tyr Leu Gln Pro Glu Leu Ala Ala Ile
    290                 295                 300

Asn Lys Glu Ala Leu Glu Arg Gln Gln Pro Trp Leu Leu Val Lys Pro
305                 310                 315                 320

Val Gly Ser Ile Leu Trp Leu Gly Pro Leu Phe Val Pro Gly Glu Thr
                325                 330                 335

Gly Cys Trp His Cys Leu Ala Gln Arg Leu Arg Gly Asn Arg Glu Val
                340                 345                 350

Glu Ala Ser Val Leu Gln Gln Lys Arg Ala Leu Gln Glu Arg Asn Gly
            355                 360                 365

Gln Asn Lys Asn Gly Ala Val Ser Cys Leu Pro Thr Ala Arg Ala Thr
    370                 375                 380

Leu Pro Ser Thr Leu Gln Thr Gly Leu Gln Trp Ala Ala Thr Glu Ile
385                 390                 395                 400

Ala Lys Trp Met Val Lys Arg His Leu Asn Ala Ile Ala Pro Gly Thr
                405                 410                 415

Ala Arg Phe Pro Thr Leu Ala Gly Lys Ile Phe Thr Phe Asn Gln Thr
                420                 425                 430

Thr Leu Glu Leu Lys Ala His Pro Leu Ser Arg Arg Pro Gln Cys Pro
            435                 440                 445

Thr Cys Gly Asp Gln Glu Ile Leu Gln Arg Arg Gly Phe Glu Pro Leu
    450                 455                 460

Lys Leu Glu Ser Arg Pro Lys His Phe Thr Ser Asp Gly Gly His Arg
465                 470                 475                 480

Ala Thr Thr Pro Glu Gln Thr Val Gln Lys Tyr Gln His Leu Ile Gly
                485                 490                 495

Pro Ile Thr Gly Val Val Thr Glu Leu Val Arg Ile Ser Asp Pro Ala
                500                 505                 510

Asn Pro Leu Val His Thr Tyr Arg Ala Gly His Ser Phe Gly Ser Ser
            515                 520                 525

Ala Gly Ser Leu Arg Gly Leu Arg Asn Thr Leu Arg Tyr Lys Ser Ser
    530                 535                 540

Gly Lys Gly Lys Thr Asp Ser Gln Ser Arg Ala Ser Gly Leu Cys Glu
545                 550                 555                 560

Ala Ile Glu Arg Tyr Ser Gly Ile Phe Leu Gly Asp Glu Pro Arg Lys
                565                 570                 575

Arg Ala Thr Leu Ala Glu Leu Gly Asp Leu Ala Ile His Pro Glu Gln
                580                 585                 590

Cys Leu His Phe Ser Asp Arg Gln Tyr Asp Asn Arg Asp Ala Leu Asn
            595                 600                 605

Ala Glu Gly Ser Ala Ala Tyr Arg Trp Ile Pro His Arg Phe Ala
    610                 615                 620

Ala Ser Gln Ala Ile Asp Trp Thr Pro Leu Trp Ser Leu Thr Glu Gln
625                 630                 635                 640

Lys His Lys Tyr Val Pro Thr Ala Ile Cys Tyr Tyr Asn Tyr Leu Leu
                645                 650                 655

Pro Pro Ala Asp Arg Phe Cys Lys Ala Asp Ser Asn Gly Asn Ala Ala
                660                 665                 670
```

-continued

Gly Asn Ser Leu Glu Glu Ala Ile Leu Gln Gly Phe Met Glu Leu Val
                675                 680                 685

Glu Arg Asp Ser Val Ala Leu Trp Trp Tyr Asn Arg Leu Arg Arg Pro
        690                 695                 700

Glu Val Glu Leu Ser Ser Phe Glu Pro Tyr Phe Leu Gln Leu Gln
705                 710                 715                 720

Gln Phe Tyr Arg Ser Gln Asn Arg Glu Leu Trp Val Leu Asp Leu Thr
                725                 730                 735

Ala Asp Leu Gly Ile Pro Ala Phe Ala Gly Leu Ser Arg Arg Thr Val
                740                 745                 750

Gly Ser Ser Glu Arg Val Ser Ile Gly Phe Gly Ala His Leu Asp Pro
        755                 760                 765

Lys Ile Ala Ile Leu Arg Ala Leu Thr Glu Val Ser Gln Val Gly Leu
        770                 775                 780

Glu Leu Asp Lys Val Pro Asp Glu Lys Leu Asp Gly Glu Ser Lys Asp
785                 790                 795                 800

Trp Met Leu Glu Val Thr Leu Glu Thr His Pro Cys Leu Ala Pro Asp
                805                 810                 815

Pro Ser Gln Pro Arg Lys Thr Ala Asn Asp Tyr Pro Lys Arg Trp Ser
                820                 825                 830

Asp Asp Ile Tyr Thr Asp Val Met Ala Cys Val Glu Met Ala Lys Val
                835                 840                 845

Ala Gly Leu Glu Thr Leu Val Leu Asp Gln Thr Arg Pro Asp Ile Gly
        850                 855                 860

Leu Asn Val Val Lys Val Met Ile Pro Gly Met Arg Thr Phe Trp Ser
865                 870                 875                 880

Arg Tyr Gly Pro Gly Arg Leu Tyr Asp Val Pro Val Gln Leu Gly Trp
                885                 890                 895

Leu Lys Glu Pro Leu Ala Glu Ala Glu Met Asn Pro Thr Asn Ile Pro
                900                 905                 910

Phe

<210> SEQ ID NO 11
<211> LENGTH: 918
<212> TYPE: PRT
<213> ORGANISM: Artificial
<220> FEATURE:
<223> OTHER INFORMATION: Synthesized Peptide.

<400> SEQUENCE: 11

Met Gly His His His His His His His His Ser Ser Gly His
1               5                   10                  15

Ile Glu Gly Arg Ala Ser Asn Lys Lys Asn Ile Leu Pro Gln Gln Gly
                20                  25                  30

Gln Pro Val Ile Arg Leu Thr Ala Gly Gln Leu Ser Ser Gln Leu Ala
                35                  40                  45

Glu Leu Ser Glu Glu Ala Leu Gly Asp Ala Gly Leu Glu Ala Ser Gly
        50                  55                  60

Ser Gly Ser Gly Ser Gly Ser Gly Ser Gly Ser Gly Ser Gly Ser Gly
65                  70                  75                  80

Ser Gly Ser Gly Ser Gly Ser Gly Ser Gly Ser Gly Ser Gly Ser Gly
                85                  90                  95

Ser Gly Ser Gly Ser Gly Ser Gly Ser Gly Ser Gly Ser Gly Ser Gly
                100                 105                 110

Ser Gly Ser Gly Ser Gly Ser Gly Ser Gly Ser Gly Ser Gly Ser Gly

```
                115                 120                 125
    Ser Gly Ser Gly Ser His Met Gln Pro Thr Ala Leu Gln Ile Lys Pro
    130                 135                 140
    His Phe His Val Glu Ile Ile Glu Pro Lys Gln Val Tyr Leu Leu Gly
145                 150                 155                 160
    Glu Gln Gly Asn His Ala Leu Thr Gly Gln Leu Tyr Cys Gln Ile Leu
                    165                 170                 175
    Pro Phe Leu Asn Gly Glu Tyr Thr Arg Glu Gln Ile Val Glu Lys Leu
                    180                 185                 190
    Asp Gly Gln Val Pro Glu Glu Tyr Ile Asp Phe Val Leu Ser Arg Leu
                    195                 200                 205
    Val Glu Lys Gly Tyr Leu Thr Glu Val Ala Pro Glu Leu Ser Leu Glu
    210                 215                 220
    Val Ala Ala Phe Trp Ser Glu Leu Gly Ile Ala Pro Ser Val Val Ala
    225                 230                 235                 240
    Glu Gly Leu Lys Gln Pro Val Thr Val Thr Ala Gly Lys Gly Ile
                        245                 250                 255
    Arg Glu Gly Ile Val Ala Asn Leu Ala Ala Ala Leu Glu Glu Ala Gly
                    260                 265                 270
    Ile Gln Val Ser Asp Pro Lys Ala Pro Lys Ala Pro Lys Ala Gly Asp
                    275                 280                 285
    Ser Thr Ala Gln Leu Gln Val Val Leu Thr Asp Asp Tyr Leu Gln Pro
    290                 295                 300
    Glu Leu Ala Ala Ile Asn Lys Glu Ala Leu Glu Arg Gln Gln Pro Trp
    305                 310                 315                 320
    Leu Leu Val Lys Pro Val Gly Ser Ile Leu Trp Leu Gly Pro Leu Phe
                        325                 330                 335
    Val Pro Gly Glu Thr Gly Cys Trp His Cys Leu Ala Gln Arg Leu Arg
                    340                 345                 350
    Gly Asn Arg Glu Val Glu Ala Ser Val Leu Gln Gln Lys Arg Ala Leu
                    355                 360                 365
    Gln Glu Arg Asn Gly Gln Asn Lys Asn Gly Ala Val Ser Cys Leu Pro
    370                 375                 380
    Thr Ala Arg Ala Thr Leu Pro Ser Thr Leu Gln Thr Gly Leu Gln Trp
    385                 390                 395                 400
    Ala Ala Thr Glu Ile Ala Lys Trp Met Val Lys Arg His Leu Asn Ala
                        405                 410                 415
    Ile Ala Pro Gly Thr Ala Arg Phe Pro Thr Leu Ala Gly Lys Ile Phe
                    420                 425                 430
    Thr Phe Asn Gln Thr Thr Leu Glu Leu Lys Ala His Pro Leu Ser Arg
                    435                 440                 445
    Arg Pro Gln Cys Pro Thr Cys Gly Asp Gln Glu Ile Leu Gln Arg Arg
    450                 455                 460
    Gly Phe Glu Pro Leu Lys Leu Glu Ser Arg Pro Lys His Phe Thr Ser
    465                 470                 475                 480
    Asp Gly Gly His Arg Ala Thr Thr Pro Glu Gln Thr Val Gln Lys Tyr
                        485                 490                 495
    Gln His Leu Ile Gly Pro Ile Thr Gly Val Val Thr Glu Leu Val Arg
                    500                 505                 510
    Ile Ser Asp Pro Ala Asn Pro Leu Val His Thr Tyr Arg Ala Gly His
                    515                 520                 525
    Ser Phe Gly Ser Ser Ala Gly Ser Leu Arg Gly Leu Arg Asn Thr Leu
    530                 535                 540
```

Arg Tyr Lys Ser Ser Gly Lys Gly Lys Thr Asp Ser Gln Ser Arg Ala
545                 550                 555                 560

Ser Gly Leu Cys Glu Ala Ile Glu Arg Tyr Ser Gly Ile Phe Leu Gly
            565                 570                 575

Asp Glu Pro Arg Lys Arg Ala Thr Leu Ala Glu Leu Gly Asp Leu Ala
        580                 585                 590

Ile His Pro Glu Gln Cys Leu His Phe Ser Asp Arg Gln Tyr Asp Asn
    595                 600                 605

Arg Asp Ala Leu Asn Ala Glu Gly Ser Ala Ala Tyr Arg Trp Ile
610                 615                 620

Pro His Arg Phe Ala Ala Ser Gln Ala Ile Asp Trp Thr Pro Leu Trp
625                 630                 635                 640

Ser Leu Thr Glu Gln Lys His Lys Tyr Val Pro Thr Ala Ile Cys Tyr
            645                 650                 655

Tyr Asn Tyr Leu Leu Pro Pro Ala Asp Arg Phe Cys Lys Ala Asp Ser
        660                 665                 670

Asn Gly Asn Ala Ala Gly Asn Ser Leu Glu Glu Ala Ile Leu Gln Gly
    675                 680                 685

Phe Met Glu Leu Val Glu Arg Asp Ser Val Ala Leu Trp Trp Tyr Asn
690                 695                 700

Arg Leu Arg Arg Pro Glu Val Glu Leu Ser Ser Phe Glu Pro Tyr
705                 710                 715                 720

Phe Leu Gln Leu Gln Gln Phe Tyr Arg Ser Gln Asn Arg Glu Leu Trp
            725                 730                 735

Val Leu Asp Leu Thr Ala Asp Leu Gly Ile Pro Ala Phe Ala Gly Leu
        740                 745                 750

Ser Arg Arg Thr Val Gly Ser Ser Glu Arg Val Ser Ile Gly Phe Gly
    755                 760                 765

Ala His Leu Asp Pro Lys Ile Ala Ile Leu Arg Ala Leu Thr Glu Val
    770                 775                 780

Ser Gln Val Gly Leu Glu Leu Asp Lys Val Pro Asp Glu Lys Leu Asp
785                 790                 795                 800

Gly Glu Ser Lys Asp Trp Met Leu Glu Val Thr Leu Gly Thr His Pro
            805                 810                 815

Cys Leu Ala Pro Asp Pro Ser Gln Pro Arg Lys Thr Ala Asn Asp Tyr
        820                 825                 830

Pro Lys Arg Trp Ser Asp Asp Ile Tyr Thr Asp Val Met Ala Cys Val
    835                 840                 845

Glu Met Ala Lys Val Ala Gly Leu Glu Thr Leu Val Leu Asp Gln Thr
    850                 855                 860

Arg Pro Asp Ile Gly Leu Asn Val Val Lys Val Met Ile Pro Gly Met
865                 870                 875                 880

Arg Thr Phe Trp Ser Arg Tyr Gly Pro Gly Arg Leu Tyr Asp Val Pro
            885                 890                 895

Val Gln Leu Gly Trp Leu Lys Glu Pro Leu Ala Glu Ala Glu Met Asn
        900                 905                 910

Pro Thr Asn Ile Pro Phe
        915

<210> SEQ ID NO 12
<211> LENGTH: 855
<212> TYPE: PRT
<213> ORGANISM: Artificial
<220> FEATURE:

<223> OTHER INFORMATION: Synthesized Peptide.

<400> SEQUENCE: 12

```
Met Gly His His His His His His His His Ser Ser Gly His
1               5                   10                  15

Ile Glu Gly Arg His Met Gln Pro Thr Ala Leu Gln Ile Lys Pro His
            20                  25                  30

Phe His Val Glu Ile Ile Glu Pro Lys Gln Val Tyr Leu Leu Gly Glu
                35                  40                  45

Gln Gly Asn His Ala Leu Thr Gly Gln Leu Tyr Cys Gln Ile Leu Pro
    50                  55                  60

Phe Leu Asn Gly Glu Tyr Thr Arg Glu Gln Ile Val Glu Lys Leu Asp
65                  70                  75                  80

Gly Gln Val Pro Glu Glu Tyr Ile Asp Phe Val Leu Ser Arg Leu Val
                85                  90                  95

Glu Lys Gly Tyr Leu Thr Glu Val Ala Pro Glu Leu Ser Leu Glu Val
            100                 105                 110

Ala Ala Phe Trp Ser Glu Leu Gly Ile Ala Pro Ser Val Val Ala Glu
        115                 120                 125

Gly Leu Lys Gln Pro Val Thr Val Thr Thr Ala Gly Lys Gly Ile Arg
    130                 135                 140

Glu Gly Ile Val Ala Asn Leu Ala Ala Ala Leu Glu Glu Ala Gly Ile
145                 150                 155                 160

Gln Val Ser Asp Pro Lys Ala Pro Lys Ala Pro Lys Ala Gly Asp Ser
                165                 170                 175

Thr Ala Gln Leu Gln Val Val Leu Thr Asp Asp Tyr Leu Gln Pro Glu
            180                 185                 190

Leu Ala Ala Ile Asn Lys Glu Ala Leu Glu Arg Gln Gln Pro Trp Leu
        195                 200                 205

Leu Val Lys Pro Val Gly Ser Ile Leu Trp Leu Gly Pro Leu Phe Val
    210                 215                 220

Pro Gly Glu Thr Gly Cys Trp His Cys Leu Ala Gln Arg Leu Arg Gly
225                 230                 235                 240

Asn Arg Glu Val Glu Ala Ser Val Leu Gln Gln Lys Ala Leu Gln
                245                 250                 255

Glu Arg Asn Gly Gln Asn Lys Asn Gly Ala Val Ser Cys Leu Pro Thr
            260                 265                 270

Ala Arg Ala Thr Leu Pro Ser Thr Leu Gln Thr Gly Leu Gln Trp Ala
        275                 280                 285

Ala Thr Glu Ile Ala Lys Trp Met Val Lys Arg His Leu Asn Ala Ile
    290                 295                 300

Ala Pro Gly Thr Ala Arg Phe Pro Thr Leu Ala Gly Lys Ile Phe Thr
305                 310                 315                 320

Phe Asn Gln Thr Thr Leu Glu Leu Lys Ala His Pro Leu Ser Arg Arg
                325                 330                 335

Pro Gln Cys Pro Thr Cys Gly Asp Gln Glu Ile Leu Gln Arg Arg Gly
            340                 345                 350

Phe Glu Pro Leu Lys Leu Glu Ser Arg Pro Lys His Phe Thr Ser Asp
        355                 360                 365

Gly Gly His Arg Ala Thr Thr Pro Glu Gln Thr Val Gln Lys Tyr Gln
    370                 375                 380

His Leu Ile Gly Pro Ile Thr Gly Val Val Thr Glu Leu Val Arg Ile
385                 390                 395                 400
```

```
Ser Asp Pro Ala Asn Pro Leu Val His Thr Tyr Arg Ala Gly His Ser
                    405                 410                 415

Phe Gly Ser Ser Ala Gly Ser Leu Arg Gly Leu Arg Asn Thr Leu Arg
                420                 425                 430

Tyr Lys Ser Ser Gly Lys Gly Lys Thr Asp Ser Gln Ser Arg Ala Ser
            435                 440                 445

Gly Leu Cys Glu Ala Ile Glu Arg Tyr Ser Gly Ile Phe Leu Gly Asp
        450                 455                 460

Glu Pro Arg Lys Arg Ala Thr Leu Ala Glu Leu Gly Asp Leu Ala Ile
465                 470                 475                 480

His Pro Glu Gln Cys Leu His Phe Ser Asp Arg Gln Tyr Asp Asn Arg
                485                 490                 495

Asp Ala Leu Asn Ala Glu Gly Ser Ala Ala Tyr Arg Trp Ile Pro
                500                 505                 510

His Arg Phe Ala Ala Ser Gln Ala Ile Asp Trp Thr Pro Leu Trp Ser
            515                 520                 525

Leu Thr Glu Gln Lys His Lys Tyr Val Pro Thr Ala Ile Cys Tyr Tyr
        530                 535                 540

Asn Tyr Leu Leu Pro Pro Ala Asp Arg Phe Cys Lys Ala Asp Ser Asn
545                 550                 555                 560

Gly Asn Ala Ala Gly Asn Ser Leu Glu Glu Ala Ile Leu Gln Gly Phe
                565                 570                 575

Met Glu Leu Val Glu Arg Asp Ser Val Ala Leu Trp Trp Tyr Asn Arg
                580                 585                 590

Leu Arg Arg Pro Glu Val Glu Leu Ser Ser Phe Glu Glu Pro Tyr Phe
            595                 600                 605

Leu Gln Leu Gln Gln Phe Tyr Arg Ser Gln Asn Arg Glu Leu Trp Val
        610                 615                 620

Leu Asp Leu Thr Ala Asp Leu Gly Ile Pro Ala Phe Ala Gly Leu Ser
625                 630                 635                 640

Arg Arg Thr Val Gly Ser Ser Glu Arg Val Ser Ile Gly Phe Gly Ala
                645                 650                 655

His Leu Asp Pro Lys Ile Ala Ile Leu Arg Ala Leu Thr Glu Val Ser
            660                 665                 670

Gln Val Gly Leu Glu Leu Asp Lys Val Pro Asp Glu Lys Leu Asp Gly
        675                 680                 685

Glu Ser Lys Asp Trp Met Leu Glu Val Thr Leu Glu Thr His Pro Cys
    690                 695                 700

Leu Ala Pro Asp Pro Ser Gln Pro Arg Lys Thr Ala Asn Asp Tyr Pro
705                 710                 715                 720

Lys Arg Trp Ser Asp Asp Ile Tyr Thr Asp Val Met Ala Cys Val Glu
                725                 730                 735

Met Ala Lys Val Ala Gly Leu Glu Thr Leu Val Leu Asp Gln Thr Arg
            740                 745                 750

Pro Asp Ile Gly Leu Asn Val Val Lys Val Met Ile Pro Gly Met Arg
        755                 760                 765

Thr Phe Trp Ser Arg Tyr Gly Pro Gly Arg Leu Tyr Asp Val Pro Val
    770                 775                 780

Gln Leu Gly Trp Leu Lys Glu Pro Leu Ala Glu Ala Glu Met Asn Pro
785                 790                 795                 800

Thr Asn Ile Pro Phe Gly Ser Leu Glu Gly Ser Gly Ser Gly Ser Gly
                805                 810                 815

Ser Gly Ser Asn Lys Lys Asn Ile Leu Pro Gln Gln Gly Gln Pro Val
```

```
                    820                 825                 830
Ile Arg Leu Thr Ala Gly Gln Leu Ser Ser Gln Leu Ala Glu Leu Ser
            835                 840                 845

Glu Glu Ala Leu Gly Asp Ala
        850                 855

<210> SEQ ID NO 13
<211> LENGTH: 875
<212> TYPE: PRT
<213> ORGANISM: Artificial
<220> FEATURE:
<223> OTHER INFORMATION: Synthesized Peptide.

<400> SEQUENCE: 13

Met Gly His His His His His His His His Ser Ser Gly His
1               5                   10                  15

Ile Glu Gly Arg His Met Gln Pro Thr Ala Leu Gln Ile Lys Pro His
            20                  25                  30

Phe His Val Glu Ile Ile Glu Pro Lys Gln Val Tyr Leu Leu Gly Glu
        35                  40                  45

Gln Gly Asn His Ala Leu Thr Gly Gln Leu Tyr Cys Gln Ile Leu Pro
    50                  55                  60

Phe Leu Asn Gly Glu Tyr Thr Arg Glu Gln Ile Val Glu Lys Leu Asp
65                  70                  75                  80

Gly Gln Val Pro Glu Glu Tyr Ile Asp Phe Val Leu Ser Arg Leu Val
                85                  90                  95

Glu Lys Gly Tyr Leu Thr Glu Val Ala Pro Glu Leu Ser Leu Glu Val
            100                 105                 110

Ala Ala Phe Trp Ser Glu Leu Gly Ile Ala Pro Ser Val Val Ala Glu
        115                 120                 125

Gly Leu Lys Gln Pro Val Thr Val Thr Ala Gly Lys Gly Ile Arg
    130                 135                 140

Glu Gly Ile Val Ala Asn Leu Ala Ala Leu Glu Glu Ala Gly Ile
145                 150                 155                 160

Gln Val Ser Asp Pro Lys Ala Pro Lys Ala Pro Lys Ala Gly Asp Ser
                165                 170                 175

Thr Ala Gln Leu Gln Val Val Leu Thr Asp Asp Tyr Leu Gln Pro Glu
            180                 185                 190

Leu Ala Ala Ile Asn Lys Glu Ala Leu Glu Arg Gln Gln Pro Trp Leu
        195                 200                 205

Leu Val Lys Pro Val Gly Ser Ile Leu Trp Leu Gly Pro Leu Phe Val
    210                 215                 220

Pro Gly Glu Thr Gly Cys Trp His Cys Leu Ala Gln Arg Leu Arg Gly
225                 230                 235                 240

Asn Arg Glu Val Glu Ala Ser Val Leu Gln Gln Lys Arg Ala Leu Gln
                245                 250                 255

Glu Arg Asn Gly Gln Asn Lys Asn Gly Ala Val Ser Cys Leu Pro Thr
            260                 265                 270

Ala Arg Ala Thr Leu Pro Ser Thr Leu Gln Thr Gly Leu Gln Trp Ala
        275                 280                 285

Ala Thr Glu Ile Ala Lys Trp Met Val Lys Arg His Leu Asn Ala Ile
    290                 295                 300

Ala Pro Gly Thr Ala Arg Phe Pro Thr Leu Ala Gly Lys Ile Phe Thr
305                 310                 315                 320

Phe Asn Gln Thr Thr Leu Glu Leu Lys Ala His Pro Leu Ser Arg Arg
```

```
                325                 330                 335
Pro Gln Cys Pro Thr Cys Gly Asp Gln Glu Ile Leu Gln Arg Arg Gly
            340                 345                 350
Phe Glu Pro Leu Lys Leu Glu Ser Arg Pro Lys His Phe Thr Ser Asp
            355                 360                 365
Gly Gly His Arg Ala Thr Thr Pro Glu Gln Thr Val Gln Lys Tyr Gln
            370                 375                 380
His Leu Ile Gly Pro Ile Thr Gly Val Val Thr Glu Leu Val Arg Ile
385                 390                 395                 400
Ser Asp Pro Ala Asn Pro Leu Val His Thr Tyr Arg Ala Gly His Ser
                405                 410                 415
Phe Gly Ser Ser Ala Gly Ser Leu Arg Gly Leu Arg Asn Thr Leu Arg
                420                 425                 430
Tyr Lys Ser Ser Gly Lys Gly Lys Thr Asp Ser Gln Ser Arg Ala Ser
                435                 440                 445
Gly Leu Cys Glu Ala Ile Glu Arg Tyr Ser Gly Ile Phe Leu Gly Asp
                450                 455                 460
Glu Pro Arg Lys Arg Ala Thr Leu Ala Glu Leu Gly Asp Leu Ala Ile
465                 470                 475                 480
His Pro Glu Gln Cys Leu His Phe Ser Asp Arg Gln Tyr Asp Asn Arg
                485                 490                 495
Asp Ala Leu Asn Ala Glu Gly Ser Ala Ala Tyr Arg Trp Ile Pro
                500                 505                 510
His Arg Phe Ala Ala Ser Gln Ala Ile Asp Trp Thr Pro Leu Trp Ser
                515                 520                 525
Leu Thr Glu Gln Lys His Lys Tyr Val Pro Thr Ala Ile Cys Tyr Tyr
                530                 535                 540
Asn Tyr Leu Leu Pro Pro Ala Asp Arg Phe Cys Lys Ala Asp Ser Asn
545                 550                 555                 560
Gly Asn Ala Ala Gly Asn Ser Leu Glu Glu Ala Ile Leu Gln Gly Phe
                565                 570                 575
Met Glu Leu Val Glu Arg Asp Ser Val Ala Leu Trp Trp Tyr Asn Arg
                580                 585                 590
Leu Arg Arg Pro Glu Val Glu Leu Ser Ser Phe Glu Glu Pro Tyr Phe
                595                 600                 605
Leu Gln Leu Gln Gln Phe Tyr Arg Ser Gln Asn Arg Glu Leu Trp Val
                610                 615                 620
Leu Asp Leu Thr Ala Asp Leu Gly Ile Pro Ala Phe Ala Gly Leu Ser
625                 630                 635                 640
Arg Arg Thr Val Gly Ser Ser Glu Arg Val Ser Ile Gly Phe Gly Ala
                645                 650                 655
His Leu Asp Pro Lys Ile Ala Ile Leu Arg Ala Leu Thr Glu Val Ser
                660                 665                 670
Gln Val Gly Leu Glu Leu Asp Lys Val Pro Asp Glu Lys Leu Asp Gly
                675                 680                 685
Glu Ser Lys Asp Trp Met Leu Glu Val Thr Leu Glu Thr His Pro Cys
                690                 695                 700
Leu Ala Pro Asp Pro Ser Gln Pro Arg Lys Thr Ala Asn Asp Tyr Pro
705                 710                 715                 720
Lys Arg Trp Ser Asp Asp Ile Tyr Thr Asp Val Met Ala Cys Val Glu
                725                 730                 735
Met Ala Lys Val Ala Gly Leu Glu Thr Leu Val Leu Asp Gln Thr Arg
                740                 745                 750
```

```
Pro Asp Ile Gly Leu Asn Val Val Lys Val Met Ile Pro Gly Met Arg
        755                 760                 765

Thr Phe Trp Ser Arg Tyr Gly Pro Gly Arg Leu Tyr Asp Val Pro Val
        770                 775                 780

Gln Leu Gly Trp Leu Lys Glu Pro Leu Ala Glu Ala Glu Met Asn Pro
785                 790                 795                 800

Thr Asn Ile Pro Phe Gly Ser Leu Glu Gly Ser Gly Ser Gly Ser Gly
                805                 810                 815

Ser Gly Ser Gly Ser Gly Ser Gly Ser Gly Ser Gly Ser Gly Ser Gly
            820                 825                 830

Ser Gly Ser Gly Ser Gly Ser Asn Lys Lys Asn Ile Leu Pro Gln Gln
            835                 840                 845

Gly Gln Pro Val Ile Arg Leu Thr Ala Gly Gln Leu Ser Ser Gln Leu
        850                 855                 860

Ala Glu Leu Ser Glu Glu Ala Leu Gly Asp Ala
865                 870                 875

<210> SEQ ID NO 14
<211> LENGTH: 895
<212> TYPE: PRT
<213> ORGANISM: Artificial
<220> FEATURE:
<223> OTHER INFORMATION: Synthesized Peptide.

<400> SEQUENCE: 14

Met Gly His His His His His His His His Ser Ser Gly His
1               5                   10                  15

Ile Glu Gly Arg His Met Gln Pro Thr Ala Leu Gln Ile Lys Pro His
            20                  25                  30

Phe His Val Glu Ile Ile Glu Pro Lys Gln Val Tyr Leu Leu Gly Glu
        35                  40                  45

Gln Gly Asn His Ala Leu Thr Gly Gln Leu Tyr Cys Gln Ile Leu Pro
    50                  55                  60

Phe Leu Asn Gly Glu Tyr Thr Arg Glu Gln Ile Val Glu Lys Leu Asp
65                  70                  75                  80

Gly Gln Val Pro Glu Glu Tyr Ile Asp Phe Val Leu Ser Arg Leu Val
                85                  90                  95

Glu Lys Gly Tyr Leu Thr Glu Val Ala Pro Glu Leu Ser Leu Glu Val
            100                 105                 110

Ala Ala Phe Trp Ser Glu Leu Gly Ile Ala Pro Ser Val Val Ala Glu
        115                 120                 125

Gly Leu Lys Gln Pro Val Thr Val Thr Thr Ala Gly Lys Gly Ile Arg
    130                 135                 140

Glu Gly Ile Val Ala Asn Leu Ala Ala Ala Leu Glu Glu Ala Gly Ile
145                 150                 155                 160

Gln Val Ser Asp Pro Lys Ala Pro Lys Ala Pro Lys Ala Gly Asp Ser
                165                 170                 175

Thr Ala Gln Leu Gln Val Val Leu Thr Asp Asp Tyr Leu Gln Pro Glu
            180                 185                 190

Leu Ala Ala Ile Asn Lys Glu Ala Leu Glu Arg Gln Gln Pro Trp Leu
        195                 200                 205

Leu Val Lys Pro Val Gly Ser Ile Leu Trp Leu Gly Pro Leu Phe Val
    210                 215                 220

Pro Gly Glu Thr Gly Cys Trp His Cys Leu Ala Gln Arg Leu Arg Gly
225                 230                 235                 240
```

```
Asn Arg Glu Val Glu Ala Ser Val Leu Gln Gln Lys Arg Ala Leu Gln
                245                 250                 255

Glu Arg Asn Gly Gln Asn Lys Asn Gly Ala Val Ser Cys Leu Pro Thr
            260                 265                 270

Ala Arg Ala Thr Leu Pro Ser Thr Leu Gln Thr Gly Leu Gln Trp Ala
        275                 280                 285

Ala Thr Glu Ile Ala Lys Trp Met Val Lys Arg His Leu Asn Ala Ile
    290                 295                 300

Ala Pro Gly Thr Ala Arg Phe Pro Thr Leu Ala Gly Lys Ile Phe Thr
305                 310                 315                 320

Phe Asn Gln Thr Thr Leu Glu Leu Lys Ala His Pro Leu Ser Arg Arg
                325                 330                 335

Pro Gln Cys Pro Thr Cys Gly Asp Gln Glu Ile Leu Gln Arg Arg Gly
            340                 345                 350

Phe Glu Pro Leu Lys Leu Glu Ser Arg Pro Lys His Phe Thr Ser Asp
        355                 360                 365

Gly Gly His Arg Ala Thr Thr Pro Glu Gln Thr Val Gln Lys Tyr Gln
    370                 375                 380

His Leu Ile Gly Pro Ile Thr Gly Val Val Thr Glu Leu Val Arg Ile
385                 390                 395                 400

Ser Asp Pro Ala Asn Pro Leu Val His Thr Tyr Arg Ala Gly His Ser
                405                 410                 415

Phe Gly Ser Ser Ala Gly Ser Leu Arg Gly Leu Arg Asn Thr Leu Arg
            420                 425                 430

Tyr Lys Ser Ser Gly Lys Gly Lys Thr Asp Ser Gln Ser Arg Ala Ser
        435                 440                 445

Gly Leu Cys Glu Ala Ile Glu Arg Tyr Ser Gly Ile Phe Leu Gly Asp
    450                 455                 460

Glu Pro Arg Lys Arg Ala Thr Leu Ala Glu Leu Gly Asp Leu Ala Ile
465                 470                 475                 480

His Pro Glu Gln Cys Leu His Phe Ser Asp Arg Gln Tyr Asp Asn Arg
                485                 490                 495

Asp Ala Leu Asn Ala Glu Gly Ser Ala Ala Tyr Arg Trp Ile Pro
            500                 505                 510

His Arg Phe Ala Ala Ser Gln Ala Ile Asp Trp Thr Pro Leu Trp Ser
        515                 520                 525

Leu Thr Glu Gln Lys His Lys Tyr Val Pro Thr Ala Ile Cys Tyr Tyr
    530                 535                 540

Asn Tyr Leu Leu Pro Pro Ala Asp Arg Phe Cys Lys Ala Asp Ser Asn
545                 550                 555                 560

Gly Asn Ala Ala Gly Asn Ser Leu Glu Glu Ala Ile Leu Gln Gly Phe
                565                 570                 575

Met Glu Leu Val Glu Arg Asp Ser Val Ala Leu Trp Trp Tyr Asn Arg
            580                 585                 590

Leu Arg Arg Pro Glu Val Glu Leu Ser Ser Phe Glu Pro Tyr Phe
        595                 600                 605

Leu Gln Leu Gln Gln Phe Tyr Arg Ser Gln Asn Arg Glu Leu Trp Val
    610                 615                 620

Leu Asp Leu Thr Ala Asp Leu Gly Ile Pro Ala Phe Ala Gly Leu Ser
625                 630                 635                 640

Arg Arg Thr Val Gly Ser Ser Glu Arg Val Ser Ile Gly Phe Gly Ala
                645                 650                 655
```

```
His Leu Asp Pro Lys Ile Ala Ile Leu Arg Ala Leu Thr Glu Val Ser
            660                 665                 670

Gln Val Gly Leu Glu Leu Asp Lys Val Pro Asp Glu Lys Leu Asp Gly
        675                 680                 685

Glu Ser Lys Asp Trp Met Leu Glu Val Thr Leu Glu Thr His Pro Cys
    690                 695                 700

Leu Ala Pro Asp Pro Ser Gln Pro Arg Lys Thr Ala Asn Asp Tyr Pro
705                 710                 715                 720

Lys Arg Trp Ser Asp Asp Ile Tyr Thr Asp Val Met Ala Cys Val Glu
                725                 730                 735

Met Ala Lys Val Ala Gly Leu Glu Thr Leu Val Leu Asp Gln Thr Arg
            740                 745                 750

Pro Asp Ile Gly Leu Asn Val Val Lys Val Met Ile Pro Gly Met Arg
        755                 760                 765

Thr Phe Trp Ser Arg Tyr Gly Pro Gly Arg Leu Tyr Asp Val Pro Val
    770                 775                 780

Gln Leu Gly Trp Leu Lys Glu Pro Leu Ala Glu Ala Glu Met Asn Pro
785                 790                 795                 800

Thr Asn Ile Pro Phe Gly Ser Leu Glu Gly Ser Gly Ser Gly Ser Gly
                805                 810                 815

Ser Gly Ser Gly Ser Gly Ser Gly Ser Gly Ser Gly Ser Gly Ser Gly
            820                 825                 830

Ser Gly Ser Gly Ser Gly Ser Gly Ser Gly Ser Gly Ser Gly Ser Gly
        835                 840                 845

Ser Gly Ser Gly Ser Gly Ser Gly Ser Asn Lys Lys Asn Ile
    850                 855                 860

Leu Pro Gln Gln Gly Gln Pro Val Ile Arg Leu Thr Ala Gly Gln Leu
865                 870                 875                 880

Ser Ser Gln Leu Ala Glu Leu Ser Glu Glu Ala Leu Gly Asp Ala
                885                 890                 895

<210> SEQ ID NO 15
<211> LENGTH: 915
<212> TYPE: PRT
<213> ORGANISM: Artificial
<220> FEATURE:
<223> OTHER INFORMATION: Synthesized Peptide.

<400> SEQUENCE: 15

Met Gly His His His His His His His His Ser Ser Gly His
1               5                   10                  15

Ile Glu Gly Arg His Met Gln Pro Thr Ala Leu Gln Ile Lys Pro His
            20                  25                  30

Phe His Val Glu Ile Ile Glu Pro Lys Gln Val Tyr Leu Leu Gly Glu
        35                  40                  45

Gln Gly Asn His Ala Leu Thr Gly Gln Leu Tyr Cys Gln Ile Leu Pro
    50                  55                  60

Phe Leu Asn Gly Glu Tyr Thr Arg Glu Gln Ile Val Glu Lys Leu Asp
65                  70                  75                  80

Gly Gln Val Pro Glu Glu Tyr Ile Asp Phe Val Leu Ser Arg Leu Val
                85                  90                  95

Glu Lys Gly Tyr Leu Thr Glu Val Ala Pro Glu Leu Ser Leu Glu Val
            100                 105                 110

Ala Ala Phe Trp Ser Gly Leu Gly Ile Ala Pro Ser Val Val Ala Glu
        115                 120                 125
```

```
Gly Leu Lys Gln Pro Val Thr Val Thr Thr Ala Gly Lys Gly Ile Arg
130                 135                 140

Glu Gly Ile Val Ala Asn Leu Ala Ala Ala Leu Glu Glu Ala Gly Ile
145                 150                 155                 160

Gln Val Ser Asp Pro Lys Ala Pro Lys Ala Pro Lys Ala Gly Asp Ser
                165                 170                 175

Thr Ala Gln Leu Gln Val Val Leu Thr Asp Asp Tyr Leu Gln Pro Glu
            180                 185                 190

Leu Ala Ala Ile Asn Lys Glu Ala Leu Glu Arg Gln Gln Pro Trp Leu
        195                 200                 205

Leu Val Lys Pro Val Gly Ser Ile Leu Trp Leu Gly Pro Leu Phe Val
210                 215                 220

Pro Gly Glu Thr Gly Cys Trp His Cys Leu Ala Gln Arg Leu Arg Gly
225                 230                 235                 240

Asn Arg Glu Val Glu Ala Ser Val Leu Gln Gln Lys Arg Ala Leu Gln
                245                 250                 255

Glu Arg Asn Gly Gln Asn Lys Asn Gly Ala Val Ser Cys Leu Pro Thr
            260                 265                 270

Ala Arg Ala Thr Leu Pro Ser Thr Leu Gln Thr Gly Leu Gln Trp Ala
        275                 280                 285

Ala Thr Glu Ile Ala Lys Trp Met Val Lys Arg His Leu Asn Ala Ile
290                 295                 300

Ala Pro Gly Thr Ala Arg Phe Pro Thr Leu Ala Gly Lys Ile Phe Thr
305                 310                 315                 320

Phe Asn Gln Thr Thr Leu Glu Leu Lys Ala His Pro Leu Ser Arg Arg
                325                 330                 335

Pro Gln Cys Pro Thr Cys Gly Asp Gln Glu Ile Leu Gln Arg Arg Gly
            340                 345                 350

Phe Glu Pro Leu Lys Leu Glu Ser Arg Pro Lys His Phe Thr Ser Asp
        355                 360                 365

Gly Gly His Arg Ala Thr Thr Pro Glu Gln Thr Val Gln Lys Tyr Gln
370                 375                 380

His Leu Ile Gly Pro Ile Thr Gly Val Val Thr Glu Leu Val Arg Ile
385                 390                 395                 400

Ser Asp Pro Ala Asn Pro Leu Val His Thr Tyr Arg Ala Gly His Ser
                405                 410                 415

Phe Gly Ser Ser Ala Gly Ser Leu Arg Gly Leu Arg Asn Thr Leu Arg
            420                 425                 430

Tyr Lys Ser Ser Gly Lys Gly Lys Thr Asp Ser Gln Ser Arg Ala Ser
        435                 440                 445

Gly Leu Cys Glu Ala Ile Glu Arg Tyr Ser Gly Ile Phe Leu Gly Asp
450                 455                 460

Glu Pro Arg Lys Arg Ala Thr Leu Ala Glu Leu Gly Asp Leu Ala Ile
465                 470                 475                 480

His Pro Glu Gln Cys Leu His Phe Ser Asp Arg Gln Tyr Asp Asn Arg
                485                 490                 495

Asp Ala Leu Asn Ala Glu Gly Ser Ala Ala Tyr Arg Trp Ile Pro
            500                 505                 510

His Arg Phe Ala Ala Ser Gln Ala Ile Asp Trp Thr Pro Leu Trp Ser
        515                 520                 525

Leu Thr Glu Gln Lys His Lys Tyr Val Pro Thr Ala Ile Cys Tyr Tyr
530                 535                 540

Asn Tyr Leu Leu Pro Pro Ala Asp Arg Phe Cys Lys Ala Asp Ser Asn
```

```
            545                 550                 555                 560
        Gly Asn Ala Ala Gly Asn Ser Leu Glu Glu Ala Ile Leu Gln Gly Phe
                            565                 570                 575

Met Glu Leu Val Glu Arg Asp Ser Val Ala Leu Trp Trp Tyr Asn Arg
                            580                 585                 590

Leu Arg Arg Pro Glu Val Glu Leu Ser Ser Phe Glu Pro Tyr Phe
                            595                 600                 605

Leu Gln Leu Gln Gln Phe Tyr Arg Ser Gln Asn Arg Glu Leu Trp Val
                            610                 615                 620

Leu Asp Leu Thr Ala Asp Leu Gly Ile Pro Ala Phe Ala Gly Leu Ser
        625                 630                 635                 640

Arg Arg Thr Val Gly Ser Ser Glu Arg Val Ser Ile Gly Phe Gly Ala
                            645                 650                 655

His Leu Asp Pro Lys Ile Ala Ile Leu Arg Ala Leu Thr Glu Val Ser
                            660                 665                 670

Gln Val Gly Leu Glu Leu Asp Lys Val Pro Asp Glu Lys Leu Asp Gly
                            675                 680                 685

Glu Ser Lys Asp Trp Met Leu Glu Val Thr Leu Glu Thr His Pro Cys
                            690                 695                 700

Leu Ala Pro Asp Pro Ser Gln Pro Arg Lys Thr Ala Asn Asp Tyr Pro
        705                 710                 715                 720

Lys Arg Trp Ser Asp Ile Tyr Thr Asp Val Met Ala Cys Val Glu
                            725                 730                 735

Met Ala Lys Val Ala Gly Leu Glu Thr Leu Val Leu Asp Gln Thr Arg
                            740                 745                 750

Pro Asp Ile Gly Leu Asn Val Val Lys Val Met Ile Pro Gly Met Arg
                            755                 760                 765

Thr Phe Trp Ser Arg Tyr Gly Pro Gly Arg Leu Tyr Asp Val Pro Val
                            770                 775                 780

Gln Leu Gly Trp Leu Lys Glu Pro Leu Ala Glu Ala Glu Met Asn Pro
        785                 790                 795                 800

Thr Asn Ile Pro Phe Gly Ser Leu Glu Gly Ser Gly Ser Gly Ser Gly
                            805                 810                 815

Ser Gly Ser Gly Ser Gly Ser Gly Ser Gly Ser Gly Ser Gly Ser Gly
                            820                 825                 830

Ser Gly Ser Gly Ser Gly Ser Gly Ser Gly Ser Gly Ser Gly Ser Gly
                            835                 840                 845

Ser Gly Ser Gly Ser Gly Ser Gly Ser Gly Ser Gly Ser Gly Ser Gly
        850                 855                 860

Ser Gly Ser Gly Ser Gly Ser Gly Ser Gly Ser Gly Ser Gly Ser Asn
        865                 870                 875                 880

Lys Lys Asn Ile Leu Pro Gln Gln Gly Gln Pro Val Ile Arg Leu Thr
                            885                 890                 895

Ala Gly Gln Leu Ser Ser Gln Leu Ala Glu Leu Ser Glu Glu Ala Leu
                            900                 905                 910

Gly Asp Ala
                915

<210> SEQ ID NO 16
<211> LENGTH: 13
<212> TYPE: PRT
<213> ORGANISM: Artificial
<220> FEATURE:
<223> OTHER INFORMATION: Synthesized Peptide.
```

```
<400> SEQUENCE: 16

Met Gly Val Thr Ala Cys Ile Thr Phe Cys Gly Gly Gly
1               5                   10

<210> SEQ ID NO 17
<211> LENGTH: 13
<212> TYPE: PRT
<213> ORGANISM: Artificial
<220> FEATURE:
<223> OTHER INFORMATION: Synthesized Peptide.

<400> SEQUENCE: 17

Met Gly Val Cys Ala Cys Ile Cys Phe Cys Gly Gly Gly
1               5                   10

<210> SEQ ID NO 18
<211> LENGTH: 13
<212> TYPE: PRT
<213> ORGANISM: Artificial
<220> FEATURE:
<223> OTHER INFORMATION: Synthesized Peptide.

<400> SEQUENCE: 18

Met Gly Val Thr Ala Thr Ile Thr Phe Thr Gly Gly Gly
1               5                   10

<210> SEQ ID NO 19
<211> LENGTH: 13
<212> TYPE: PRT
<213> ORGANISM: Artificial
<220> FEATURE:
<223> OTHER INFORMATION: Synthesized Peptide.

<400> SEQUENCE: 19

Met Gly Val Ser Ala Ser Ile Ser Phe Ser Gly Gly Gly
1               5                   10

<210> SEQ ID NO 20
<211> LENGTH: 22
<212> TYPE: PRT
<213> ORGANISM: Artificial
<220> FEATURE:
<223> OTHER INFORMATION: Synthesized Peptide.

<400> SEQUENCE: 20

Met Gly Leu Glu Ala Ser Val Cys Ala Cys Ile Cys Phe Cys Ala Tyr
1               5                   10                  15

Asp Gly Val Glu Pro Ser
            20

<210> SEQ ID NO 21
<211> LENGTH: 19
<212> TYPE: PRT
<213> ORGANISM: Artificial
<220> FEATURE:
<223> OTHER INFORMATION: Synthesized Peptide.

<400> SEQUENCE: 21

Met Gly Leu Glu Ala Ser Val Cys Ala Cys Ile Cys Phe Cys Ala Tyr
1               5                   10                  15

Asp Gly Val

<210> SEQ ID NO 22
<211> LENGTH: 17
<212> TYPE: PRT
```

```
<213> ORGANISM: Artificial
<220> FEATURE:
<223> OTHER INFORMATION: Synthesized Peptide.

<400> SEQUENCE: 22

Met Gly Leu Glu Ala Ser Val Cys Ala Cys Ile Cys Phe Cys Ala Tyr
1               5                   10                  15

Asp

<210> SEQ ID NO 23
<211> LENGTH: 15
<212> TYPE: PRT
<213> ORGANISM: Artificial
<220> FEATURE:
<223> OTHER INFORMATION: Synthesized Peptide.

<400> SEQUENCE: 23

Met Gly Leu Glu Ala Ser Val Cys Ala Cys Ile Cys Phe Cys Ala
1               5                   10                  15

<210> SEQ ID NO 24
<211> LENGTH: 14
<212> TYPE: PRT
<213> ORGANISM: Artificial
<220> FEATURE:
<223> OTHER INFORMATION: Synthesized Peptide.

<400> SEQUENCE: 24

Met Gly Leu Glu Ala Ser Val Cys Ala Cys Ile Cys Phe Cys
1               5                   10

<210> SEQ ID NO 25
<211> LENGTH: 20
<212> TYPE: PRT
<213> ORGANISM: Artificial
<220> FEATURE:
<223> OTHER INFORMATION: Synthesized Peptide.

<400> SEQUENCE: 25

Met Glu Ala Ser Val Cys Ala Cys Ile Cys Phe Cys Ala Tyr Asp Gly
1               5                   10                  15

Val Glu Pro Ser
            20

<210> SEQ ID NO 26
<211> LENGTH: 18
<212> TYPE: PRT
<213> ORGANISM: Artificial
<220> FEATURE:
<223> OTHER INFORMATION: Synthesized Peptide.

<400> SEQUENCE: 26

Met Ser Val Cys Ala Cys Ile Cys Phe Cys Ala Tyr Asp Gly Val Glu
1               5                   10                  15

Pro Ser

<210> SEQ ID NO 27
<211> LENGTH: 17
<212> TYPE: PRT
<213> ORGANISM: Artificial
<220> FEATURE:
<223> OTHER INFORMATION: Synthesized Peptide.

<400> SEQUENCE: 27

Met Val Cys Ala Cys Ile Cys Phe Cys Ala Tyr Asp Gly Val Glu Pro
```

```
                   1               5                  10                  15
Ser

<210> SEQ ID NO 28
<211> LENGTH: 22
<212> TYPE: PRT
<213> ORGANISM: Artificial
<220> FEATURE:
<223> OTHER INFORMATION: Synthesized Peptide.

<400> SEQUENCE: 28

Met Gly Gly Gly Gly Gly Val Cys Ala Cys Ile Cys Phe Cys Gly Gly
  1               5                  10                  15

Gly Gly Gly Gly Gly Gly
            20

<210> SEQ ID NO 29
<211> LENGTH: 19
<212> TYPE: PRT
<213> ORGANISM: Artificial
<220> FEATURE:
<223> OTHER INFORMATION: Synthesized Peptide.

<400> SEQUENCE: 29

Met Gly Gly Gly Gly Gly Val Cys Ala Cys Ile Cys Phe Cys Gly Gly
  1               5                  10                  15

Gly Gly Gly

<210> SEQ ID NO 30
<211> LENGTH: 17
<212> TYPE: PRT
<213> ORGANISM: Artificial
<220> FEATURE:
<223> OTHER INFORMATION: Synthesized Peptide.

<400> SEQUENCE: 30

Met Gly Gly Gly Gly Gly Val Cys Ala Cys Ile Cys Phe Cys Gly Gly
  1               5                  10                  15

Gly

<210> SEQ ID NO 31
<211> LENGTH: 15
<212> TYPE: PRT
<213> ORGANISM: Artificial
<220> FEATURE:
<223> OTHER INFORMATION: Synthesized Peptide.

<400> SEQUENCE: 31

Met Gly Gly Gly Gly Gly Val Cys Ala Cys Ile Cys Phe Cys Gly
  1               5                  10                  15

<210> SEQ ID NO 32
<211> LENGTH: 14
<212> TYPE: PRT
<213> ORGANISM: Artificial
<220> FEATURE:
<223> OTHER INFORMATION: Synthesized Peptide.

<400> SEQUENCE: 32

Met Gly Gly Gly Gly Gly Val Cys Ala Cys Ile Cys Phe Cys
  1               5                  10

<210> SEQ ID NO 33
<211> LENGTH: 20
```

```
<212> TYPE: PRT
<213> ORGANISM: Artificial
<220> FEATURE:
<223> OTHER INFORMATION: Synthesized Peptide.

<400> SEQUENCE: 33

Met Gly Gly Gly Val Cys Ala Cys Ile Cys Phe Cys Gly Gly Gly
1               5                   10                  15

Gly Gly Gly Gly
            20

<210> SEQ ID NO 34
<211> LENGTH: 17
<212> TYPE: PRT
<213> ORGANISM: Artificial
<220> FEATURE:
<223> OTHER INFORMATION: Synthesized Peptide.

<400> SEQUENCE: 34

Met Val Cys Ala Cys Ile Cys Phe Cys Gly Gly Gly Gly Gly Gly
1               5                   10                  15

Gly

<210> SEQ ID NO 35
<211> LENGTH: 11
<212> TYPE: PRT
<213> ORGANISM: Artificial
<220> FEATURE:
<223> OTHER INFORMATION: Synthesized Peptide.

<400> SEQUENCE: 35

Met Gly Val Cys Ala Cys Ile Cys Phe Cys Ala
1               5                   10

<210> SEQ ID NO 36
<211> LENGTH: 13
<212> TYPE: PRT
<213> ORGANISM: Artificial
<220> FEATURE:
<223> OTHER INFORMATION: Synthesized Peptide.

<400> SEQUENCE: 36

Met Gly Val Cys Ala Cys Ile Cys Phe Cys Ala Tyr Asp
1               5                   10

<210> SEQ ID NO 37
<211> LENGTH: 15
<212> TYPE: PRT
<213> ORGANISM: Artificial
<220> FEATURE:
<223> OTHER INFORMATION: Synthesized Peptide.

<400> SEQUENCE: 37

Met Gly Val Cys Ala Cys Ile Cys Phe Cys Ala Tyr Asp Gly Val
1               5                   10                  15

<210> SEQ ID NO 38
<211> LENGTH: 18
<212> TYPE: PRT
<213> ORGANISM: Artificial
<220> FEATURE:
<223> OTHER INFORMATION: Synthesized Peptide.

<400> SEQUENCE: 38

Met Gly Val Cys Ala Cys Ile Cys Phe Cys Ala Tyr Asp Gly Val Glu
1               5                   10                  15
```

Pro Ser

<210> SEQ ID NO 39
<211> LENGTH: 13
<212> TYPE: PRT
<213> ORGANISM: Artificial
<220> FEATURE:
<223> OTHER INFORMATION: Synthesized Peptide.

<400> SEQUENCE: 39

Met Gly Val Cys Ala Cys Glu Cys Phe Cys Ala Tyr Asp
1               5                   10

<210> SEQ ID NO 40
<211> LENGTH: 15
<212> TYPE: PRT
<213> ORGANISM: Artificial
<220> FEATURE:
<223> OTHER INFORMATION: Synthesized Peptide.

<400> SEQUENCE: 40

Met Gly Val Cys Ala Cys Glu Cys Phe Cys Ala Tyr Asp Gly Val
1               5                   10                  15

<210> SEQ ID NO 41
<211> LENGTH: 18
<212> TYPE: PRT
<213> ORGANISM: Artificial
<220> FEATURE:
<223> OTHER INFORMATION: Synthesized Peptide.

<400> SEQUENCE: 41

Met Gly Val Cys Ala Cys Glu Cys Phe Cys Ala Tyr Asp Gly Val Glu
1               5                   10                  15

Pro Ser

<210> SEQ ID NO 42
<211> LENGTH: 15
<212> TYPE: PRT
<213> ORGANISM: Artificial
<220> FEATURE:
<223> OTHER INFORMATION: Synthesized Peptide.

<400> SEQUENCE: 42

Met Gly Gly Gly Val Cys Ala Cys Glu Cys Phe Cys Ala Tyr Asp
1               5                   10                  15

<210> SEQ ID NO 43
<211> LENGTH: 15
<212> TYPE: PRT
<213> ORGANISM: Artificial
<220> FEATURE:
<223> OTHER INFORMATION: Synthesized Peptide.

<400> SEQUENCE: 43

Met Glu Ala Ala Val Cys Ala Cys Glu Cys Phe Cys Ala Tyr Asp
1               5                   10                  15

<210> SEQ ID NO 44
<211> LENGTH: 13
<212> TYPE: PRT
<213> ORGANISM: Artificial
<220> FEATURE:
<223> OTHER INFORMATION: Synthesized Peptide.

<400> SEQUENCE: 44

```
Met Gly Val Cys Ala Cys Glu Cys Phe Cys Ala Tyr Asp
1               5                   10
```

<210> SEQ ID NO 45
<211> LENGTH: 15
<212> TYPE: PRT
<213> ORGANISM: Artificial
<220> FEATURE:
<223> OTHER INFORMATION: Synthesized Peptide.

<400> SEQUENCE: 45

```
Met Gly Val Cys Ala Cys Glu Cys Phe Cys Ala Tyr Asp Gly Val
1               5                   10                  15
```

<210> SEQ ID NO 46
<211> LENGTH: 18
<212> TYPE: PRT
<213> ORGANISM: Artificial
<220> FEATURE:
<223> OTHER INFORMATION: Synthesized Peptide.

<400> SEQUENCE: 46

```
Met Gly Val Cys Ala Cys Glu Cys Phe Cys Ala Tyr Asp Gly Val Glu
1               5                   10                  15

Pro Ser
```

<210> SEQ ID NO 47
<211> LENGTH: 15
<212> TYPE: PRT
<213> ORGANISM: Artificial
<220> FEATURE:
<223> OTHER INFORMATION: Synthesized Peptide.

<400> SEQUENCE: 47

```
Met Gly Gly Gly Val Cys Ala Cys Glu Cys Phe Cys Ala Tyr Asp
1               5                   10                  15
```

<210> SEQ ID NO 48
<211> LENGTH: 17
<212> TYPE: PRT
<213> ORGANISM: Artificial
<220> FEATURE:
<223> OTHER INFORMATION: Synthesized Peptide.

<400> SEQUENCE: 48

```
Met Gly Gly Gly Val Cys Ala Cys Glu Cys Phe Cys Ala Tyr Asp Gly
1               5                   10                  15

Val
```

<210> SEQ ID NO 49
<211> LENGTH: 20
<212> TYPE: PRT
<213> ORGANISM: Artificial
<220> FEATURE:
<223> OTHER INFORMATION: Synthesized Peptide.

<400> SEQUENCE: 49

```
Met Gly Gly Gly Val Cys Ala Cys Glu Cys Phe Cys Ala Tyr Asp Gly
1               5                   10                  15

Val Glu Pro Ser
            20
```

<210> SEQ ID NO 50
<211> LENGTH: 15

<212> TYPE: PRT
<213> ORGANISM: Artificial
<220> FEATURE:
<223> OTHER INFORMATION: Synthesized Peptide.

<400> SEQUENCE: 50

Met Glu Ala Ala Val Cys Ala Cys Glu Cys Phe Cys Ala Tyr Asp
1               5                   10                  15

<210> SEQ ID NO 51
<211> LENGTH: 17
<212> TYPE: PRT
<213> ORGANISM: Artificial
<220> FEATURE:
<223> OTHER INFORMATION: Synthesized Peptide.

<400> SEQUENCE: 51

Met Glu Ala Ala Val Cys Ala Cys Glu Cys Phe Cys Ala Tyr Asp Gly
1               5                   10                  15

Val

<210> SEQ ID NO 52
<211> LENGTH: 20
<212> TYPE: PRT
<213> ORGANISM: Artificial
<220> FEATURE:
<223> OTHER INFORMATION: Synthesized Peptide.

<400> SEQUENCE: 52

Met Glu Ala Ala Val Cys Ala Cys Glu Cys Phe Cys Ala Tyr Asp Gly
1               5                   10                  15

Val Glu Pro Ser
            20

<210> SEQ ID NO 53
<211> LENGTH: 13
<212> TYPE: PRT
<213> ORGANISM: Artificial
<220> FEATURE:
<223> OTHER INFORMATION: Synthesized Peptide.

<400> SEQUENCE: 53

Met Gly Val Thr Ala Cys Ile Thr Phe Cys Ala Tyr Asp
1               5                   10

<210> SEQ ID NO 54
<211> LENGTH: 13
<212> TYPE: PRT
<213> ORGANISM: Artificial
<220> FEATURE:
<223> OTHER INFORMATION: Synthesized Peptide.

<400> SEQUENCE: 54

Met Gly Val Thr Ala Cys Ile Thr Phe Cys Gly Gly Gly
1               5                   10

<210> SEQ ID NO 55
<211> LENGTH: 13
<212> TYPE: PRT
<213> ORGANISM: Artificial
<220> FEATURE:
<223> OTHER INFORMATION: Synthesized Peptide.

<400> SEQUENCE: 55

Met Gly Val Cys Ala Cys Ile Cys Phe Cys Ala Tyr Asp
1               5                   10

<210> SEQ ID NO 56
<211> LENGTH: 13
<212> TYPE: PRT
<213> ORGANISM: Artificial
<220> FEATURE:
<223> OTHER INFORMATION: Synthesized Peptide.

<400> SEQUENCE: 56

Met Gly Val Cys Ala Cys Ile Cys Phe Cys Gly Gly Gly
1               5                   10

<210> SEQ ID NO 57
<211> LENGTH: 13
<212> TYPE: PRT
<213> ORGANISM: Artificial
<220> FEATURE:
<223> OTHER INFORMATION: Synthesized Peptide.

<400> SEQUENCE: 57

Met Gly Val Thr Ala Thr Ile Thr Phe Thr Ala Tyr Asp
1               5                   10

<210> SEQ ID NO 58
<211> LENGTH: 13
<212> TYPE: PRT
<213> ORGANISM: Artificial
<220> FEATURE:
<223> OTHER INFORMATION: Synthesized Peptide.

<400> SEQUENCE: 58

Met Gly Val Thr Ala Thr Ile Thr Phe Thr Gly Gly Gly
1               5                   10

<210> SEQ ID NO 59
<211> LENGTH: 9
<212> TYPE: PRT
<213> ORGANISM: Artificial
<220> FEATURE:
<223> OTHER INFORMATION: Synthesized Peptide.

<400> SEQUENCE: 59

Met Gly Val Thr Ala Cys Ala Tyr Asp
1               5

<210> SEQ ID NO 60
<211> LENGTH: 9
<212> TYPE: PRT
<213> ORGANISM: Artificial
<220> FEATURE:
<223> OTHER INFORMATION: Synthesized Peptide.

<400> SEQUENCE: 60

Met Gly Val Thr Ala Cys Gly Gly Gly
1               5

<210> SEQ ID NO 61
<211> LENGTH: 13
<212> TYPE: PRT
<213> ORGANISM: Artificial
<220> FEATURE:
<223> OTHER INFORMATION: Synthesized Peptide.

<400> SEQUENCE: 61

Met Gly Val Thr Ala Cys Arg Thr Phe Cys Ala Tyr Asp
1               5                   10

<210> SEQ ID NO 62
<211> LENGTH: 13
<212> TYPE: PRT
<213> ORGANISM: Artificial
<220> FEATURE:
<223> OTHER INFORMATION: Synthesized Peptide.

<400> SEQUENCE: 62

Met Gly Val Thr Ala Cys Arg Thr Phe Cys Gly Gly Gly
1               5                   10

<210> SEQ ID NO 63
<211> LENGTH: 9
<212> TYPE: PRT
<213> ORGANISM: Artificial
<220> FEATURE:
<223> OTHER INFORMATION: Synthesized Peptide.

<400> SEQUENCE: 63

Met Gly Val Cys Ala Cys Gly Gly Gly
1               5

<210> SEQ ID NO 64
<211> LENGTH: 13
<212> TYPE: PRT
<213> ORGANISM: Artificial
<220> FEATURE:
<223> OTHER INFORMATION: Synthesized Peptide.

<400> SEQUENCE: 64

Met Gly Val Cys Ala Cys Ile Cys Phe Cys Gly Gly Gly
1               5                   10

<210> SEQ ID NO 65
<211> LENGTH: 17
<212> TYPE: PRT
<213> ORGANISM: Artificial
<220> FEATURE:
<223> OTHER INFORMATION: Synthesized Peptide.

<400> SEQUENCE: 65

Met Gly Val Cys Ala Cys Ile Cys Phe Cys Val Cys Ala Cys Gly Gly
1               5                   10                  15

Gly

<210> SEQ ID NO 66
<211> LENGTH: 21
<212> TYPE: PRT
<213> ORGANISM: Artificial
<220> FEATURE:
<223> OTHER INFORMATION: Synthesized Peptide.

<400> SEQUENCE: 66

Met Gly Val Cys Ala Cys Ile Cys Phe Cys Val Cys Ala Cys Val Cys
1               5                   10                  15

Ile Cys Gly Gly Gly
            20

<210> SEQ ID NO 67
<211> LENGTH: 27
<212> TYPE: PRT
<213> ORGANISM: Artificial
<220> FEATURE:
<223> OTHER INFORMATION: Synthesized Peptide.

<400> SEQUENCE: 67

```
Met Gly Val Cys Ala Cys Ile Cys Phe Cys Val Cys Ala Val Cys
1               5                   10                  15

Ile Cys Tyr Cys Phe Cys Ile Cys Gly Gly Gly
            20                  25
```

<210> SEQ ID NO 68
<211> LENGTH: 9
<212> TYPE: PRT
<213> ORGANISM: Artificial
<220> FEATURE:
<223> OTHER INFORMATION: Synthesized Peptide.

<400> SEQUENCE: 68

```
Met Gly Val Cys Ala Cys Ala Tyr Asp
1               5
```

<210> SEQ ID NO 69
<211> LENGTH: 13
<212> TYPE: PRT
<213> ORGANISM: Artificial
<220> FEATURE:
<223> OTHER INFORMATION: Synthesized Peptide.

<400> SEQUENCE: 69

```
Met Gly Val Cys Ala Cys Ile Cys Phe Cys Ala Tyr Asp
1               5                   10
```

<210> SEQ ID NO 70
<211> LENGTH: 17
<212> TYPE: PRT
<213> ORGANISM: Artificial
<220> FEATURE:
<223> OTHER INFORMATION: Synthesized Peptide.

<400> SEQUENCE: 70

```
Met Gly Val Cys Ala Cys Ile Cys Phe Cys Val Cys Ala Cys Ala Tyr
1               5                   10                  15

Asp
```

<210> SEQ ID NO 71
<211> LENGTH: 21
<212> TYPE: PRT
<213> ORGANISM: Artificial
<220> FEATURE:
<223> OTHER INFORMATION: Synthesized Peptide.

<400> SEQUENCE: 71

```
Met Gly Val Cys Ala Cys Ile Cys Phe Cys Val Cys Ala Cys Val Cys
1               5                   10                  15

Ile Cys Ala Tyr Asp
            20
```

<210> SEQ ID NO 72
<211> LENGTH: 27
<212> TYPE: PRT
<213> ORGANISM: Artificial
<220> FEATURE:
<223> OTHER INFORMATION: Synthesized Peptide.

<400> SEQUENCE: 72

```
Met Gly Val Cys Ala Cys Ile Cys Phe Cys Val Cys Ala Cys Val Cys
1               5                   10                  15

Ile Cys Tyr Cys Phe Cys Ile Cys Ala Tyr Asp
            20                  25
```

<210> SEQ ID NO 73
<211> LENGTH: 9
<212> TYPE: PRT
<213> ORGANISM: Artificial
<220> FEATURE:
<223> OTHER INFORMATION: Synthesized Peptide.

<400> SEQUENCE: 73

Met Gly Val Thr Ala Cys Gly Gly Gly
1               5

<210> SEQ ID NO 74
<211> LENGTH: 13
<212> TYPE: PRT
<213> ORGANISM: Artificial
<220> FEATURE:
<223> OTHER INFORMATION: Synthesized Peptide.

<400> SEQUENCE: 74

Met Gly Val Thr Ala Cys Ile Thr Phe Cys Gly Gly Gly
1               5                   10

<210> SEQ ID NO 75
<211> LENGTH: 17
<212> TYPE: PRT
<213> ORGANISM: Artificial
<220> FEATURE:
<223> OTHER INFORMATION: Synthesized Peptide.

<400> SEQUENCE: 75

Met Gly Val Thr Ala Cys Ile Thr Phe Cys Val Thr Ala Cys Gly Gly
1               5                   10                  15

Gly

<210> SEQ ID NO 76
<211> LENGTH: 21
<212> TYPE: PRT
<213> ORGANISM: Artificial
<220> FEATURE:
<223> OTHER INFORMATION: Synthesized Peptide.

<400> SEQUENCE: 76

Met Gly Val Thr Ala Cys Ile Thr Phe Cys Val Thr Ala Cys Val Thr
1               5                   10                  15

Ile Cys Gly Gly Gly
            20

<210> SEQ ID NO 77
<211> LENGTH: 27
<212> TYPE: PRT
<213> ORGANISM: Artificial
<220> FEATURE:
<223> OTHER INFORMATION: Synthesized Peptide.

<400> SEQUENCE: 77

Met Gly Val Thr Ala Cys Ile Thr Phe Cys Val Thr Ala Cys Val Thr
1               5                   10                  15

Ile Cys Tyr Thr Phe Cys Ile Thr Gly Gly Gly
            20                  25

<210> SEQ ID NO 78
<211> LENGTH: 21
<212> TYPE: PRT
<213> ORGANISM: Artificial

```
<220> FEATURE:
<223> OTHER INFORMATION: Synthesized Peptide.

<400> SEQUENCE: 78

Met Gly Val Thr Ala Cys Ile Thr Phe Cys Val Thr Ala Cys Val Thr
1               5                   10                  15

Ile Cys Ala Tyr Asp
            20

<210> SEQ ID NO 79
<211> LENGTH: 9
<212> TYPE: PRT
<213> ORGANISM: Artificial
<220> FEATURE:
<223> OTHER INFORMATION: Synthesized Peptide.

<400> SEQUENCE: 79

Met Gly Val Thr Ala Thr Gly Gly Gly
1               5

<210> SEQ ID NO 80
<211> LENGTH: 13
<212> TYPE: PRT
<213> ORGANISM: Artificial
<220> FEATURE:
<223> OTHER INFORMATION: Synthesized Peptide.

<400> SEQUENCE: 80

Met Gly Val Thr Ala Thr Ile Thr Phe Thr Gly Gly Gly
1               5                   10

<210> SEQ ID NO 81
<211> LENGTH: 17
<212> TYPE: PRT
<213> ORGANISM: Artificial
<220> FEATURE:
<223> OTHER INFORMATION: Synthesized Peptide.

<400> SEQUENCE: 81

Met Gly Val Thr Ala Thr Ile Thr Phe Thr Val Thr Ala Thr Gly Gly
1               5                   10                  15

Gly

<210> SEQ ID NO 82
<211> LENGTH: 21
<212> TYPE: PRT
<213> ORGANISM: Artificial
<220> FEATURE:
<223> OTHER INFORMATION: Synthesized Peptide.

<400> SEQUENCE: 82

Met Gly Val Thr Ala Thr Ile Thr Phe Thr Val Thr Ala Thr Val Thr
1               5                   10                  15

Ile Thr Gly Gly Gly
            20

<210> SEQ ID NO 83
<211> LENGTH: 27
<212> TYPE: PRT
<213> ORGANISM: Artificial
<220> FEATURE:
<223> OTHER INFORMATION: Synthesized Peptide.

<400> SEQUENCE: 83

Met Gly Val Thr Ala Thr Ile Thr Phe Thr Val Thr Ala Thr Val Thr
```

1               5                  10                  15
Ile Thr Tyr Thr Phe Thr Ile Thr Gly Gly Gly
            20                  25

<210> SEQ ID NO 84
<211> LENGTH: 21
<212> TYPE: PRT
<213> ORGANISM: Artificial
<220> FEATURE:
<223> OTHER INFORMATION: Synthesized Peptide.

<400> SEQUENCE: 84

Met Gly Val Thr Ala Thr Ile Thr Phe Thr Val Thr Ala Thr Val Thr
1               5                  10                  15

Ile Thr Ala Tyr Asp
            20

<210> SEQ ID NO 85
<211> LENGTH: 13
<212> TYPE: PRT
<213> ORGANISM: Artificial
<220> FEATURE:
<223> OTHER INFORMATION: Synthesized Peptide.

<400> SEQUENCE: 85

Met Gly Val Cys Ala Cys Asn Cys Phe Cys Ala Tyr Asp
1               5                  10

<210> SEQ ID NO 86
<211> LENGTH: 13
<212> TYPE: PRT
<213> ORGANISM: Artificial
<220> FEATURE:
<223> OTHER INFORMATION: Synthesized Peptide.

<400> SEQUENCE: 86

Met Gly Val Cys Ala Cys Gln Cys Phe Cys Ala Tyr Asp
1               5                  10

<210> SEQ ID NO 87
<211> LENGTH: 13
<212> TYPE: PRT
<213> ORGANISM: Artificial
<220> FEATURE:
<223> OTHER INFORMATION: Synthesized Peptide.

<400> SEQUENCE: 87

Met Gly Val Cys Ala Cys Lys Cys Phe Cys Ala Tyr Asp
1               5                  10

<210> SEQ ID NO 88
<211> LENGTH: 13
<212> TYPE: PRT
<213> ORGANISM: Artificial
<220> FEATURE:
<223> OTHER INFORMATION: Synthesized Peptide.

<400> SEQUENCE: 88

Met Gly Val Cys Ala Cys His Cys Phe Cys Ala Tyr Asp
1               5                  10

<210> SEQ ID NO 89
<211> LENGTH: 13
<212> TYPE: PRT
<213> ORGANISM: Artificial
<220> FEATURE:

<223> OTHER INFORMATION: Synthesized Peptide.

<400> SEQUENCE: 89

Met Gly Val Cys Ala Cys Arg Cys Phe Cys Ala Tyr Asp
1               5                   10

<210> SEQ ID NO 90
<211> LENGTH: 13
<212> TYPE: PRT
<213> ORGANISM: Artificial
<220> FEATURE:
<223> OTHER INFORMATION: Synthesized Peptide.

<400> SEQUENCE: 90

Met Gly Val Cys Ala Cys Asp Cys Phe Cys Ala Tyr Asp
1               5                   10

<210> SEQ ID NO 91
<211> LENGTH: 13
<212> TYPE: PRT
<213> ORGANISM: Artificial
<220> FEATURE:
<223> OTHER INFORMATION: Synthesized Peptide.

<400> SEQUENCE: 91

Met Gly Val Cys Ala Cys Glu Cys Phe Cys Ala Tyr Asp
1               5                   10

<210> SEQ ID NO 92
<211> LENGTH: 13
<212> TYPE: PRT
<213> ORGANISM: Artificial
<220> FEATURE:
<223> OTHER INFORMATION: Synthesized Peptide.

<400> SEQUENCE: 92

Met Gly Val Cys Ala Cys Pro Cys Phe Cys Ala Tyr Asp
1               5                   10

<210> SEQ ID NO 93
<211> LENGTH: 18
<212> TYPE: PRT
<213> ORGANISM: Artificial
<220> FEATURE:
<223> OTHER INFORMATION: Synthesized Peptide.

<400> SEQUENCE: 93

Met Gly Val Cys Ala Cys Asn Cys Phe Cys Gly Gly Gly Gly Gly
1               5                   10                  15

Gly Gly

<210> SEQ ID NO 94
<211> LENGTH: 18
<212> TYPE: PRT
<213> ORGANISM: Artificial
<220> FEATURE:
<223> OTHER INFORMATION: Synthesized Peptide.

<400> SEQUENCE: 94

Met Gly Val Cys Ala Cys Gln Cys Phe Cys Gly Gly Gly Gly Gly
1               5                   10                  15

Gly Gly

<210> SEQ ID NO 95
<211> LENGTH: 18

<212> TYPE: PRT
<213> ORGANISM: Artificial
<220> FEATURE:
<223> OTHER INFORMATION: Synthesized Peptide.

<400> SEQUENCE: 95

Met Gly Val Cys Ala Cys Lys Cys Phe Cys Gly Gly Gly Gly Gly
1               5                   10                  15

Gly Gly

<210> SEQ ID NO 96
<211> LENGTH: 18
<212> TYPE: PRT
<213> ORGANISM: Artificial
<220> FEATURE:
<223> OTHER INFORMATION: Synthesized Peptide.

<400> SEQUENCE: 96

Met Gly Val Cys Ala Cys His Cys Phe Cys Gly Gly Gly Gly Gly
1               5                   10                  15

Gly Gly

<210> SEQ ID NO 97
<211> LENGTH: 18
<212> TYPE: PRT
<213> ORGANISM: Artificial
<220> FEATURE:
<223> OTHER INFORMATION: Synthesized Peptide.

<400> SEQUENCE: 97

Met Gly Val Cys Ala Cys Arg Cys Phe Cys Gly Gly Gly Gly Gly
1               5                   10                  15

Gly Gly

<210> SEQ ID NO 98
<211> LENGTH: 18
<212> TYPE: PRT
<213> ORGANISM: Artificial
<220> FEATURE:
<223> OTHER INFORMATION: Synthesized Peptide.

<400> SEQUENCE: 98

Met Gly Val Cys Ala Cys Asp Cys Phe Cys Gly Gly Gly Gly Gly
1               5                   10                  15

Gly Gly

<210> SEQ ID NO 99
<211> LENGTH: 18
<212> TYPE: PRT
<213> ORGANISM: Artificial
<220> FEATURE:
<223> OTHER INFORMATION: Synthesized Peptide.

<400> SEQUENCE: 99

Met Gly Val Cys Ala Cys Glu Cys Phe Cys Gly Gly Gly Gly Gly
1               5                   10                  15

Gly Gly

<210> SEQ ID NO 100
<211> LENGTH: 18
<212> TYPE: PRT
<213> ORGANISM: Artificial
<220> FEATURE:
<223> OTHER INFORMATION: Synthesized Peptide.

<400> SEQUENCE: 100

Met Gly Val Thr Ala Cys Asn Thr Phe Cys Gly Gly Gly Gly Gly Gly
1               5                   10                  15

Gly Gly

<210> SEQ ID NO 101
<211> LENGTH: 18
<212> TYPE: PRT
<213> ORGANISM: Artificial
<220> FEATURE:
<223> OTHER INFORMATION: Synthesized Peptide.

<400> SEQUENCE: 101

Met Gly Val Thr Ala Cys Gln Thr Phe Cys Gly Gly Gly Gly Gly Gly
1               5                   10                  15

Gly Gly

<210> SEQ ID NO 102
<211> LENGTH: 18
<212> TYPE: PRT
<213> ORGANISM: Artificial
<220> FEATURE:
<223> OTHER INFORMATION: Synthesized Peptide.

<400> SEQUENCE: 102

Met Gly Val Thr Ala Cys Lys Thr Phe Cys Gly Gly Gly Gly Gly Gly
1               5                   10                  15

Gly Gly

<210> SEQ ID NO 103
<211> LENGTH: 18
<212> TYPE: PRT
<213> ORGANISM: Artificial
<220> FEATURE:
<223> OTHER INFORMATION: Synthesized Peptide.

<400> SEQUENCE: 103

Met Gly Val Thr Ala Cys His Thr Phe Cys Gly Gly Gly Gly Gly Gly
1               5                   10                  15

Gly Gly

<210> SEQ ID NO 104
<211> LENGTH: 18
<212> TYPE: PRT
<213> ORGANISM: Artificial
<220> FEATURE:
<223> OTHER INFORMATION: Synthesized Peptide.

<400> SEQUENCE: 104

Met Gly Val Thr Ala Cys Arg Thr Phe Cys Gly Gly Gly Gly Gly Gly
1               5                   10                  15

Gly Gly

<210> SEQ ID NO 105
<211> LENGTH: 18
<212> TYPE: PRT
<213> ORGANISM: Artificial
<220> FEATURE:
<223> OTHER INFORMATION: Synthesized Peptide.

<400> SEQUENCE: 105

Met Gly Val Thr Ala Cys Asp Thr Phe Cys Gly Gly Gly Gly Gly Gly

```
<210> SEQ ID NO 106
<211> LENGTH: 18
<212> TYPE: PRT
<213> ORGANISM: Artificial
<220> FEATURE:
<223> OTHER INFORMATION: Synthesized Peptide.

<400> SEQUENCE: 106

Met Gly Val Thr Ala Cys Glu Thr Phe Cys Gly Gly Gly Gly Gly
1               5                   10                  15

Gly Gly

<210> SEQ ID NO 107
<211> LENGTH: 13
<212> TYPE: PRT
<213> ORGANISM: Artificial
<220> FEATURE:
<223> OTHER INFORMATION: Synthesized Peptide.

<400> SEQUENCE: 107

Met Gly Val Thr Ala Cys Asn Thr Phe Cys Gly Gly Gly
1               5                   10

<210> SEQ ID NO 108
<211> LENGTH: 13
<212> TYPE: PRT
<213> ORGANISM: Artificial
<220> FEATURE:
<223> OTHER INFORMATION: Synthesized Peptide.

<400> SEQUENCE: 108

Met Gly Val Thr Ala Cys Gln Thr Phe Cys Gly Gly Gly
1               5                   10

<210> SEQ ID NO 109
<211> LENGTH: 13
<212> TYPE: PRT
<213> ORGANISM: Artificial
<220> FEATURE:
<223> OTHER INFORMATION: Synthesized Peptide.

<400> SEQUENCE: 109

Met Gly Val Thr Ala Cys Lys Thr Phe Cys Gly Gly Gly
1               5                   10

<210> SEQ ID NO 110
<211> LENGTH: 13
<212> TYPE: PRT
<213> ORGANISM: Artificial
<220> FEATURE:
<223> OTHER INFORMATION: Synthesized Peptide.

<400> SEQUENCE: 110

Met Gly Val Thr Ala Cys His Thr Phe Cys Gly Gly Gly
1               5                   10

<210> SEQ ID NO 111
<211> LENGTH: 13
<212> TYPE: PRT
<213> ORGANISM: Artificial
<220> FEATURE:
<223> OTHER INFORMATION: Synthesized Peptide.
```

```
<400> SEQUENCE: 111

Met Gly Val Thr Ala Cys Arg Thr Phe Cys Gly Gly Gly
1               5                   10

<210> SEQ ID NO 112
<211> LENGTH: 13
<212> TYPE: PRT
<213> ORGANISM: Artificial
<220> FEATURE:
<223> OTHER INFORMATION: Synthesized Peptide.

<400> SEQUENCE: 112

Met Gly Val Thr Ala Cys Asp Thr Phe Cys Gly Gly Gly
1               5                   10

<210> SEQ ID NO 113
<211> LENGTH: 13
<212> TYPE: PRT
<213> ORGANISM: Artificial
<220> FEATURE:
<223> OTHER INFORMATION: Synthesized Peptide.

<400> SEQUENCE: 113

Met Gly Val Thr Ala Cys Glu Thr Phe Cys Gly Gly Gly
1               5                   10

<210> SEQ ID NO 114
<211> LENGTH: 13
<212> TYPE: PRT
<213> ORGANISM: Artificial
<220> FEATURE:
<223> OTHER INFORMATION: Synthesized Peptide.

<400> SEQUENCE: 114

Met Gly Ala Leu Ile Cys Val Ala Leu Cys Ala Tyr Asp
1               5                   10

<210> SEQ ID NO 115
<211> LENGTH: 13
<212> TYPE: PRT
<213> ORGANISM: Artificial
<220> FEATURE:
<223> OTHER INFORMATION: Synthesized Peptide.

<400> SEQUENCE: 115

Met Gly Leu Ile Val Cys Ala Ala Leu Cys Ala Tyr Asp
1               5                   10

<210> SEQ ID NO 116
<211> LENGTH: 14
<212> TYPE: PRT
<213> ORGANISM: Artificial
<220> FEATURE:
<223> OTHER INFORMATION: Synthesized Peptide.

<400> SEQUENCE: 116

Met Gly Ala Leu Cys Val Ala Cys Ile Leu Cys Ala Tyr Asp
1               5                   10

<210> SEQ ID NO 117
<211> LENGTH: 13
<212> TYPE: PRT
<213> ORGANISM: Artificial
<220> FEATURE:
<223> OTHER INFORMATION: Synthesized Peptide.

<400> SEQUENCE: 117
```

Met Gly Asp Asn His Cys Lys Arg Asn Cys Ala Tyr Asp
1               5                   10

<210> SEQ ID NO 118
<211> LENGTH: 13
<212> TYPE: PRT
<213> ORGANISM: Artificial
<220> FEATURE:
<223> OTHER INFORMATION: Synthesized Peptide.

<400> SEQUENCE: 118

Met Gly Glu Arg Lys Cys Asn His Glu Cys Ala Tyr Asp
1               5                   10

<210> SEQ ID NO 119
<211> LENGTH: 13
<212> TYPE: PRT
<213> ORGANISM: Artificial
<220> FEATURE:
<223> OTHER INFORMATION: Synthesized Peptide.

<400> SEQUENCE: 119

Met Gly Tyr Phe Trp Cys Phe Phe Trp Cys Ala Tyr Asp
1               5                   10

<210> SEQ ID NO 120
<211> LENGTH: 13
<212> TYPE: PRT
<213> ORGANISM: Artificial
<220> FEATURE:
<223> OTHER INFORMATION: Synthesized Peptide.

<400> SEQUENCE: 120

Met Gly Phe Trp Trp Cys Tyr Phe Tyr Cys Ala Tyr Asp
1               5                   10

<210> SEQ ID NO 121
<211> LENGTH: 13
<212> TYPE: PRT
<213> ORGANISM: Artificial
<220> FEATURE:
<223> OTHER INFORMATION: Synthesized Peptide.

<400> SEQUENCE: 121

Met Gly Ala Asn Ile Cys Lys Ala Asn Cys Ala Tyr Asp
1               5                   10

<210> SEQ ID NO 122
<211> LENGTH: 13
<212> TYPE: PRT
<213> ORGANISM: Artificial
<220> FEATURE:
<223> OTHER INFORMATION: Synthesized Peptide.

<400> SEQUENCE: 122

Met Gly Ala Asn Ile Cys Ala Lys Ala Cys Ala Tyr Asp
1               5                   10

<210> SEQ ID NO 123
<211> LENGTH: 13
<212> TYPE: PRT
<213> ORGANISM: Artificial
<220> FEATURE:
<223> OTHER INFORMATION: Synthesized Peptide.

<400> SEQUENCE: 123

```
Met Gly Leu Asn Val Cys Lys Ala Asn Cys Ala Tyr Asp
1               5                   10
```

<210> SEQ ID NO 124
<211> LENGTH: 13
<212> TYPE: PRT
<213> ORGANISM: Artificial
<220> FEATURE:
<223> OTHER INFORMATION: Synthesized Peptide.

<400> SEQUENCE: 124

```
Met Gly Tyr Arg Trp Cys Asn Phe Glu Cys Ala Tyr Asp
1               5                   10
```

<210> SEQ ID NO 125
<211> LENGTH: 13
<212> TYPE: PRT
<213> ORGANISM: Artificial
<220> FEATURE:
<223> OTHER INFORMATION: Synthesized Peptide.

<400> SEQUENCE: 125

```
Met Gly Tyr Arg Trp Cys Phe Asn Phe Cys Ala Tyr Asp
1               5                   10
```

<210> SEQ ID NO 126
<211> LENGTH: 13
<212> TYPE: PRT
<213> ORGANISM: Artificial
<220> FEATURE:
<223> OTHER INFORMATION: Synthesized Peptide.

<400> SEQUENCE: 126

```
Met Gly Ala Tyr Leu Cys Trp Ile Phe Cys Ala Tyr Asp
1               5                   10
```

<210> SEQ ID NO 127
<211> LENGTH: 13
<212> TYPE: PRT
<213> ORGANISM: Artificial
<220> FEATURE:
<223> OTHER INFORMATION: Synthesized Peptide.

<400> SEQUENCE: 127

```
Met Gly Ala Tyr Asn Cys Ile Trp Arg Cys Ala Tyr Asp
1               5                   10
```

<210> SEQ ID NO 128
<211> LENGTH: 13
<212> TYPE: PRT
<213> ORGANISM: Artificial
<220> FEATURE:
<223> OTHER INFORMATION: Synthesized Peptide.

<400> SEQUENCE: 128

```
Met Gly Ala Asn Tyr Cys Ile Arg Trp Cys Ala Tyr Asp
1               5                   10
```

<210> SEQ ID NO 129
<211> LENGTH: 18
<212> TYPE: PRT
<213> ORGANISM: Artificial
<220> FEATURE:
<223> OTHER INFORMATION: Synthesized Peptide.

<400> SEQUENCE: 129

```
Met Gly Ala Leu Ile Cys Val Ala Leu Cys Gly Gly Gly Gly Gly Gly
```

```
1               5                  10                 15

Gly Gly

<210> SEQ ID NO 130
<211> LENGTH: 18
<212> TYPE: PRT
<213> ORGANISM: Artificial
<220> FEATURE:
<223> OTHER INFORMATION: Synthesized Peptide.

<400> SEQUENCE: 130

Met Gly Leu Ile Val Cys Ala Ala Leu Cys Gly Gly Gly Gly Gly
1               5                  10                 15

Gly Gly

<210> SEQ ID NO 131
<211> LENGTH: 19
<212> TYPE: PRT
<213> ORGANISM: Artificial
<220> FEATURE:
<223> OTHER INFORMATION: Synthesized Peptide.

<400> SEQUENCE: 131

Met Gly Ala Leu Cys Val Ala Cys Ile Leu Cys Gly Gly Gly Gly
1               5                  10                 15

Gly Gly Gly

<210> SEQ ID NO 132
<211> LENGTH: 18
<212> TYPE: PRT
<213> ORGANISM: Artificial
<220> FEATURE:
<223> OTHER INFORMATION: Synthesized Peptide.

<400> SEQUENCE: 132

Met Gly Asp Asn His Cys Lys Arg Asn Cys Gly Gly Gly Gly Gly
1               5                  10                 15

Gly Gly

<210> SEQ ID NO 133
<211> LENGTH: 18
<212> TYPE: PRT
<213> ORGANISM: Artificial
<220> FEATURE:
<223> OTHER INFORMATION: Synthesized Peptide.

<400> SEQUENCE: 133

Met Gly Glu Arg Lys Cys Asn His Glu Cys Gly Gly Gly Gly Gly
1               5                  10                 15

Gly Gly

<210> SEQ ID NO 134
<211> LENGTH: 18
<212> TYPE: PRT
<213> ORGANISM: Artificial
<220> FEATURE:
<223> OTHER INFORMATION: Synthesized Peptide.

<400> SEQUENCE: 134

Met Gly Tyr Phe Trp Cys Phe Phe Trp Cys Gly Gly Gly Gly Gly
1               5                  10                 15

Gly Gly
```

```
<210> SEQ ID NO 135
<211> LENGTH: 18
<212> TYPE: PRT
<213> ORGANISM: Artificial
<220> FEATURE:
<223> OTHER INFORMATION: Synthesized Peptide.

<400> SEQUENCE: 135

Met Gly Phe Trp Trp Cys Tyr Phe Tyr Cys Gly Gly Gly Gly Gly
1               5                   10                  15

Gly Gly

<210> SEQ ID NO 136
<211> LENGTH: 18
<212> TYPE: PRT
<213> ORGANISM: Artificial
<220> FEATURE:
<223> OTHER INFORMATION: Synthesized Peptide.

<400> SEQUENCE: 136

Met Gly Ala Asn Ile Cys Lys Ala Asn Cys Gly Gly Gly Gly Gly
1               5                   10                  15

Gly Gly

<210> SEQ ID NO 137
<211> LENGTH: 18
<212> TYPE: PRT
<213> ORGANISM: Artificial
<220> FEATURE:
<223> OTHER INFORMATION: Synthesized Peptide.

<400> SEQUENCE: 137

Met Gly Leu Asn Val Cys Lys Ala Asn Cys Gly Gly Gly Gly Gly
1               5                   10                  15

Gly Gly

<210> SEQ ID NO 138
<211> LENGTH: 18
<212> TYPE: PRT
<213> ORGANISM: Artificial
<220> FEATURE:
<223> OTHER INFORMATION: Synthesized Peptide.

<400> SEQUENCE: 138

Met Gly Tyr Arg Trp Cys Asn Phe Glu Cys Gly Gly Gly Gly Gly
1               5                   10                  15

Gly Gly

<210> SEQ ID NO 139
<211> LENGTH: 13
<212> TYPE: PRT
<213> ORGANISM: Artificial
<220> FEATURE:
<223> OTHER INFORMATION: Synthesized Peptide.

<400> SEQUENCE: 139

Met Gly Ala Leu Ile Cys Val Ala Leu Cys Ala Tyr Asp
1               5                   10

<210> SEQ ID NO 140
<211> LENGTH: 17
<212> TYPE: PRT
<213> ORGANISM: Artificial
<220> FEATURE:
```

<223> OTHER INFORMATION: Synthesized Peptide.

<400> SEQUENCE: 140

Met Gly Ala Leu Ile Cys Val Ala Leu Cys Val Leu Ala Cys Ala Tyr
1               5                   10                  15

Asp

<210> SEQ ID NO 141
<211> LENGTH: 21
<212> TYPE: PRT
<213> ORGANISM: Artificial
<220> FEATURE:
<223> OTHER INFORMATION: Synthesized Peptide.

<400> SEQUENCE: 141

Met Gly Ala Leu Ile Cys Val Ala Leu Cys Val Leu Ala Cys Ile Ile
1               5                   10                  15

Val Cys Ala Tyr Asp
            20

<210> SEQ ID NO 142
<211> LENGTH: 16
<212> TYPE: PRT
<213> ORGANISM: Artificial
<220> FEATURE:
<223> OTHER INFORMATION: Synthesized Peptide.

<400> SEQUENCE: 142

Ala Met Asx Phe Arg Val Arg Val Cys Asp Tyr Asp Leu Trp Gly Gly
1               5                   10                  15

<210> SEQ ID NO 143
<211> LENGTH: 18
<212> TYPE: PRT
<213> ORGANISM: Artificial
<220> FEATURE:
<223> OTHER INFORMATION: Synthesized Peptide.

<400> SEQUENCE: 143

Ala Met Asx Phe Arg Val Arg Val Cys Ala Ala Asp Tyr Asp Leu Trp
1               5                   10                  15

Gly Gly

<210> SEQ ID NO 144
<211> LENGTH: 20
<212> TYPE: PRT
<213> ORGANISM: Artificial
<220> FEATURE:
<223> OTHER INFORMATION: Synthesized Peptide.

<400> SEQUENCE: 144

Ala Met Asx Phe Arg Val Arg Val Cys Ala Cys Ala Ala Asp Tyr Asp
1               5                   10                  15

Leu Trp Gly Gly
            20

<210> SEQ ID NO 145
<211> LENGTH: 22
<212> TYPE: PRT
<213> ORGANISM: Artificial
<220> FEATURE:
<223> OTHER INFORMATION: Synthesized Peptide.

<400> SEQUENCE: 145

Ala Met Asx Phe Arg Val Arg Val Cys Ala Cys Ala Cys Ala Ala Asp
1               5                   10                  15

Tyr Asp Leu Trp Gly Gly
            20

<210> SEQ ID NO 146
<211> LENGTH: 24
<212> TYPE: PRT
<213> ORGANISM: Artificial
<220> FEATURE:
<223> OTHER INFORMATION: Synthesized Peptide.

<400> SEQUENCE: 146

Ala Met Asx Phe Arg Val Arg Val Cys Ala Cys Ala Cys Ala Cys Ala
1               5                   10                  15

Ala Asp Tyr Asp Leu Trp Gly Gly
            20

<210> SEQ ID NO 147
<211> LENGTH: 19
<212> TYPE: PRT
<213> ORGANISM: Artificial
<220> FEATURE:
<223> OTHER INFORMATION: Synthesized Peptide.

<400> SEQUENCE: 147

Ala Met Asx Phe Arg Val Arg Val Cys Ala Ala Asp Tyr Asp Leu Trp
1               5                   10                  15

Ala Tyr Asp

<210> SEQ ID NO 148
<211> LENGTH: 21
<212> TYPE: PRT
<213> ORGANISM: Artificial
<220> FEATURE:
<223> OTHER INFORMATION: Synthesized Peptide.

<400> SEQUENCE: 148

Ala Met Asx Phe Arg Val Arg Val Cys Ala Cys Ala Ala Asp Tyr Asp
1               5                   10                  15

Leu Trp Ala Tyr Asp
            20

<210> SEQ ID NO 149
<211> LENGTH: 23
<212> TYPE: PRT
<213> ORGANISM: Artificial
<220> FEATURE:
<223> OTHER INFORMATION: Synthesized Peptide.

<400> SEQUENCE: 149

Ala Met Asx Phe Arg Val Arg Val Cys Ala Cys Ala Cys Ala Ala Asp
1               5                   10                  15

Tyr Asp Leu Trp Ala Tyr Asp
            20

<210> SEQ ID NO 150
<211> LENGTH: 25
<212> TYPE: PRT
<213> ORGANISM: Artificial
<220> FEATURE:
<223> OTHER INFORMATION: Synthesized Peptide.

<400> SEQUENCE: 150

```
Ala Met Asx Phe Arg Val Arg Val Cys Ala Cys Ala Cys Ala
1               5                   10                  15

Ala Asp Tyr Asp Leu Trp Ala Tyr Asp
            20                  25
```

<210> SEQ ID NO 151
<211> LENGTH: 13
<212> TYPE: PRT
<213> ORGANISM: Artificial
<220> FEATURE:
<223> OTHER INFORMATION: Synthesized Peptide.

<400> SEQUENCE: 151

```
Met Gly Val Thr Ala Cys Ile Thr Phe Cys Ala Tyr Asp
1               5                   10
```

<210> SEQ ID NO 152
<211> LENGTH: 16
<212> TYPE: PRT
<213> ORGANISM: Artificial
<220> FEATURE:
<223> OTHER INFORMATION: Synthesized Peptide.

<400> SEQUENCE: 152

```
Met Gly Val Thr Ala Cys Ile Thr Phe Cys Ala Tyr Asp Gly Ser Gly
1               5                   10                  15
```

<210> SEQ ID NO 153
<211> LENGTH: 13
<212> TYPE: PRT
<213> ORGANISM: Artificial
<220> FEATURE:
<223> OTHER INFORMATION: Synthesized Peptide.

<400> SEQUENCE: 153

```
Met Gly Ala Asn Ile Cys Lys Ala Asn Cys Ala Tyr Asp
1               5                   10
```

<210> SEQ ID NO 154
<211> LENGTH: 16
<212> TYPE: PRT
<213> ORGANISM: Artificial
<220> FEATURE:
<223> OTHER INFORMATION: Synthesized Peptide.

<400> SEQUENCE: 154

```
Met Gly Ala Asn Ile Cys Lys Ala Asn Cys Ala Tyr Asp Gly Ser Gly
1               5                   10                  15
```

<210> SEQ ID NO 155
<211> LENGTH: 13
<212> TYPE: PRT
<213> ORGANISM: Artificial
<220> FEATURE:
<223> OTHER INFORMATION: Synthesized Peptide.

<400> SEQUENCE: 155

```
Met Gly Ala Asn Ile Cys Ala Lys Ala Cys Ala Tyr Asp
1               5                   10
```

<210> SEQ ID NO 156
<211> LENGTH: 16
<212> TYPE: PRT
<213> ORGANISM: Artificial
<220> FEATURE:
<223> OTHER INFORMATION: Synthesized Peptide.

```
<400> SEQUENCE: 156

Met Gly Ala Asn Ile Cys Ala Lys Ala Cys Ala Tyr Asp Gly Ser Gly
1               5                   10                  15

<210> SEQ ID NO 157
<211> LENGTH: 13
<212> TYPE: PRT
<213> ORGANISM: Artificial
<220> FEATURE:
<223> OTHER INFORMATION: Synthesized Peptide.

<400> SEQUENCE: 157

Met Gly Tyr Arg Trp Cys Phe Asn Phe Cys Ala Tyr Asp
1               5                   10

<210> SEQ ID NO 158
<211> LENGTH: 16
<212> TYPE: PRT
<213> ORGANISM: Artificial
<220> FEATURE:
<223> OTHER INFORMATION: Synthesized Peptide.

<400> SEQUENCE: 158

Met Gly Tyr Arg Trp Cys Phe Asn Phe Cys Ala Tyr Asp Gly Ser Gly
1               5                   10                  15

<210> SEQ ID NO 159
<211> LENGTH: 12
<212> TYPE: PRT
<213> ORGANISM: Artificial
<220> FEATURE:
<223> OTHER INFORMATION: Synthesized Peptide.

<400> SEQUENCE: 159

Met Gly Ile Ala Ile Cys Glu Ile Ile Ala Tyr Asp
1               5                   10

<210> SEQ ID NO 160
<211> LENGTH: 15
<212> TYPE: PRT
<213> ORGANISM: Artificial
<220> FEATURE:
<223> OTHER INFORMATION: Synthesized Peptide.

<400> SEQUENCE: 160

Met Gly Ile Ala Ile Cys Glu Ile Ile Ala Tyr Asp Gly Ser Gly
1               5                   10                  15

<210> SEQ ID NO 161
<211> LENGTH: 12
<212> TYPE: PRT
<213> ORGANISM: Artificial
<220> FEATURE:
<223> OTHER INFORMATION: Synthesized Peptide.

<400> SEQUENCE: 161

Met Gly Ile Ile Arg Cys Ile Ala Ile Ala Tyr Asp
1               5                   10

<210> SEQ ID NO 162
<211> LENGTH: 15
<212> TYPE: PRT
<213> ORGANISM: Artificial
<220> FEATURE:
<223> OTHER INFORMATION: Synthesized Peptide.

<400> SEQUENCE: 162
```

Met Gly Ile Ile Arg Cys Ile Ala Ile Ala Tyr Asp Gly Ser Gly
1               5                   10                  15

<210> SEQ ID NO 163
<211> LENGTH: 13
<212> TYPE: PRT
<213> ORGANISM: Artificial
<220> FEATURE:
<223> OTHER INFORMATION: Synthesized Peptide.

<400> SEQUENCE: 163

Met Gly Ala Leu Ile Cys Val Ala Leu Cys Ala Tyr Asp
1               5                   10

<210> SEQ ID NO 164
<211> LENGTH: 14
<212> TYPE: PRT
<213> ORGANISM: Artificial
<220> FEATURE:
<223> OTHER INFORMATION: Synthesized Peptide.

<400> SEQUENCE: 164

Met Gly Ala Leu Ile Cys Val Ala Leu Cys Val Ala Tyr Asp
1               5                   10

<210> SEQ ID NO 165
<211> LENGTH: 15
<212> TYPE: PRT
<213> ORGANISM: Artificial
<220> FEATURE:
<223> OTHER INFORMATION: Synthesized Peptide.

<400> SEQUENCE: 165

Met Gly Ala Leu Ile Cys Val Ala Leu Cys Val Leu Ala Tyr Asp
1               5                   10                  15

<210> SEQ ID NO 166
<211> LENGTH: 16
<212> TYPE: PRT
<213> ORGANISM: Artificial
<220> FEATURE:
<223> OTHER INFORMATION: Synthesized Peptide.

<400> SEQUENCE: 166

Met Gly Ala Leu Ile Cys Val Ala Leu Cys Ala Tyr Asp Gly Ser Gly
1               5                   10                  15

<210> SEQ ID NO 167
<211> LENGTH: 17
<212> TYPE: PRT
<213> ORGANISM: Artificial
<220> FEATURE:
<223> OTHER INFORMATION: Synthesized Peptide.

<400> SEQUENCE: 167

Met Gly Ala Leu Ile Cys Val Ala Leu Cys Val Ala Tyr Asp Gly Ser
1               5                   10                  15

Gly

<210> SEQ ID NO 168
<211> LENGTH: 18
<212> TYPE: PRT
<213> ORGANISM: Artificial
<220> FEATURE:
<223> OTHER INFORMATION: Synthesized Peptide.

<400> SEQUENCE: 168

Met Gly Ala Leu Ile Cys Val Ala Leu Cys Val Leu Ala Tyr Asp Gly
1               5                   10                  15
Ser Gly

<210> SEQ ID NO 169
<211> LENGTH: 9
<212> TYPE: PRT
<213> ORGANISM: Artificial
<220> FEATURE:
<223> OTHER INFORMATION: Synthesized Peptide.

<400> SEQUENCE: 169

Met Gly Ile Cys Phe Trp Ala Tyr Asp
1               5

<210> SEQ ID NO 170
<211> LENGTH: 9
<212> TYPE: PRT
<213> ORGANISM: Artificial
<220> FEATURE:
<223> OTHER INFORMATION: Synthesized Peptide.

<400> SEQUENCE: 170

Met Gly Ile Thr Phe Trp Ala Tyr Asp
1               5

<210> SEQ ID NO 171
<211> LENGTH: 9
<212> TYPE: PRT
<213> ORGANISM: Artificial
<220> FEATURE:
<223> OTHER INFORMATION: Synthesized Peptide.

<400> SEQUENCE: 171

Met Gly Ile Ser Phe Trp Ala Tyr Asp
1               5

<210> SEQ ID NO 172
<211> LENGTH: 13
<212> TYPE: PRT
<213> ORGANISM: Artificial
<220> FEATURE:
<223> OTHER INFORMATION: Synthesized Peptide.

<400> SEQUENCE: 172

Met Gly Val Phe Ala Trp Ile Cys Phe Trp Ala Tyr Asp
1               5                   10

<210> SEQ ID NO 173
<211> LENGTH: 13
<212> TYPE: PRT
<213> ORGANISM: Artificial
<220> FEATURE:
<223> OTHER INFORMATION: Synthesized Peptide.

<400> SEQUENCE: 173

Met Gly Val Phe Ala Trp Ile Thr Phe Trp Ala Tyr Asp
1               5                   10

<210> SEQ ID NO 174
<211> LENGTH: 13
<212> TYPE: PRT
<213> ORGANISM: Artificial
<220> FEATURE:
<223> OTHER INFORMATION: Synthesized Peptide.

```
<400> SEQUENCE: 174

Met Gly Val Phe Ala Trp Ile Ser Phe Trp Ala Tyr Asp
1               5                   10

<210> SEQ ID NO 175
<211> LENGTH: 7
<212> TYPE: PRT
<213> ORGANISM: Artificial
<220> FEATURE:
<223> OTHER INFORMATION: Synthesized Peptide.

<400> SEQUENCE: 175

Met Gly Val Cys Ala Tyr Asp
1               5

<210> SEQ ID NO 176
<211> LENGTH: 12
<212> TYPE: PRT
<213> ORGANISM: Artificial
<220> FEATURE:
<223> OTHER INFORMATION: Synthesized Peptide.

<400> SEQUENCE: 176

Met Gly Ile Asn Ile Cys Ile Asn Ile Ala Tyr Asp
1               5                   10

<210> SEQ ID NO 177
<211> LENGTH: 12
<212> TYPE: PRT
<213> ORGANISM: Artificial
<220> FEATURE:
<223> OTHER INFORMATION: Synthesized Peptide.

<400> SEQUENCE: 177

Met Gly Ile Ile Asn Cys Ile Asn Ile Ala Tyr Asp
1               5                   10

<210> SEQ ID NO 178
<211> LENGTH: 12
<212> TYPE: PRT
<213> ORGANISM: Artificial
<220> FEATURE:
<223> OTHER INFORMATION: Synthesized Peptide.

<400> SEQUENCE: 178

Met Gly Ile Asn Ile Cys Asn Ile Ile Ala Tyr Asp
1               5                   10

<210> SEQ ID NO 179
<211> LENGTH: 12
<212> TYPE: PRT
<213> ORGANISM: Artificial
<220> FEATURE:
<223> OTHER INFORMATION: Synthesized Peptide.

<400> SEQUENCE: 179

Met Gly Ile Ile Asn Cys Asn Ile Ile Ala Tyr Asp
1               5                   10

<210> SEQ ID NO 180
<211> LENGTH: 12
<212> TYPE: PRT
<213> ORGANISM: Artificial
<220> FEATURE:
<223> OTHER INFORMATION: Synthesized Peptide.
```

<400> SEQUENCE: 180

Met Gly Ile Ala Ile Cys Asn Ile Ile Ala Tyr Asp
1               5                   10

<210> SEQ ID NO 181
<211> LENGTH: 12
<212> TYPE: PRT
<213> ORGANISM: Artificial
<220> FEATURE:
<223> OTHER INFORMATION: Synthesized Peptide.

<400> SEQUENCE: 181

Met Gly Ile Ala Ile Cys Gln Ile Ile Ala Tyr Asp
1               5                   10

<210> SEQ ID NO 182
<211> LENGTH: 12
<212> TYPE: PRT
<213> ORGANISM: Artificial
<220> FEATURE:
<223> OTHER INFORMATION: Synthesized Peptide.

<400> SEQUENCE: 182

Met Gly Ile Ala Ile Cys Lys Ile Ile Ala Tyr Asp
1               5                   10

<210> SEQ ID NO 183
<211> LENGTH: 12
<212> TYPE: PRT
<213> ORGANISM: Artificial
<220> FEATURE:
<223> OTHER INFORMATION: Synthesized Peptide.

<400> SEQUENCE: 183

Met Gly Ile Ala Ile Cys Arg Ile Ile Ala Tyr Asp
1               5                   10

<210> SEQ ID NO 184
<211> LENGTH: 12
<212> TYPE: PRT
<213> ORGANISM: Artificial
<220> FEATURE:
<223> OTHER INFORMATION: Synthesized Peptide.

<400> SEQUENCE: 184

Met Gly Ile Ala Ile Cys His Ile Ile Ala Tyr Asp
1               5                   10

<210> SEQ ID NO 185
<211> LENGTH: 12
<212> TYPE: PRT
<213> ORGANISM: Artificial
<220> FEATURE:
<223> OTHER INFORMATION: Synthesized Peptide.

<400> SEQUENCE: 185

Met Gly Ile Ala Ile Cys Glu Ile Ile Ala Tyr Asp
1               5                   10

<210> SEQ ID NO 186
<211> LENGTH: 12
<212> TYPE: PRT
<213> ORGANISM: Artificial
<220> FEATURE:
<223> OTHER INFORMATION: Synthesized Peptide.

<400> SEQUENCE: 186

Met Gly Ile Ile Asn Cys Ile Ala Ile Ala Tyr Asp
1               5                   10

<210> SEQ ID NO 187
<211> LENGTH: 12
<212> TYPE: PRT
<213> ORGANISM: Artificial
<220> FEATURE:
<223> OTHER INFORMATION: Synthesized Peptide.

<400> SEQUENCE: 187

Met Gly Ile Ile Gln Cys Ile Ala Ile Ala Tyr Asp
1               5                   10

<210> SEQ ID NO 188
<211> LENGTH: 12
<212> TYPE: PRT
<213> ORGANISM: Artificial
<220> FEATURE:
<223> OTHER INFORMATION: Synthesized Peptide.

<400> SEQUENCE: 188

Met Gly Ile Ile Lys Cys Ile Ala Ile Ala Tyr Asp
1               5                   10

<210> SEQ ID NO 189
<211> LENGTH: 12
<212> TYPE: PRT
<213> ORGANISM: Artificial
<220> FEATURE:
<223> OTHER INFORMATION: Synthesized Peptide.

<400> SEQUENCE: 189

Met Gly Ile Ile Arg Cys Ile Ala Ile Ala Tyr Asp
1               5                   10

<210> SEQ ID NO 190
<211> LENGTH: 12
<212> TYPE: PRT
<213> ORGANISM: Artificial
<220> FEATURE:
<223> OTHER INFORMATION: Synthesized Peptide.

<400> SEQUENCE: 190

Met Gly Ile Ile His Cys Ile Ala Ile Ala Tyr Asp
1               5                   10

<210> SEQ ID NO 191
<211> LENGTH: 12
<212> TYPE: PRT
<213> ORGANISM: Artificial
<220> FEATURE:
<223> OTHER INFORMATION: Synthesized Peptide.

<400> SEQUENCE: 191

Met Gly Ile Ile Asp Cys Ile Ala Ile Ala Tyr Asp
1               5                   10

<210> SEQ ID NO 192
<211> LENGTH: 12
<212> TYPE: PRT
<213> ORGANISM: Artificial
<220> FEATURE:
<223> OTHER INFORMATION: Synthesized Peptide.

<400> SEQUENCE: 192

```
Met Gly Ile Ile Glu Cys Ile Ala Ile Ala Tyr Asp
1               5                   10
```

<210> SEQ ID NO 193
<211> LENGTH: 12
<212> TYPE: PRT
<213> ORGANISM: Artificial
<220> FEATURE:
<223> OTHER INFORMATION: Synthesized Peptide.

<400> SEQUENCE: 193

```
Met Gly Ile Ile Pro Cys Ile Ala Ile Ala Tyr Asp
1               5                   10
```

<210> SEQ ID NO 194
<211> LENGTH: 12
<212> TYPE: PRT
<213> ORGANISM: Artificial
<220> FEATURE:
<223> OTHER INFORMATION: Synthesized Peptide.

<400> SEQUENCE: 194

```
Met Gly Ile Ile Thr Cys Ile Ala Ile Ala Tyr Asp
1               5                   10
```

<210> SEQ ID NO 195
<211> LENGTH: 12
<212> TYPE: PRT
<213> ORGANISM: Artificial
<220> FEATURE:
<223> OTHER INFORMATION: Synthesized Peptide.

<400> SEQUENCE: 195

```
Met Gly Ile Ile Ser Cys Ile Ala Ile Ala Tyr Asp
1               5                   10
```

<210> SEQ ID NO 196
<211> LENGTH: 12
<212> TYPE: PRT
<213> ORGANISM: Artificial
<220> FEATURE:
<223> OTHER INFORMATION: Synthesized Peptide.

<400> SEQUENCE: 196

```
Met Gly Ile Ile Cys Cys Ile Ala Ile Ala Tyr Asp
1               5                   10
```

<210> SEQ ID NO 197
<211> LENGTH: 12
<212> TYPE: PRT
<213> ORGANISM: Artificial
<220> FEATURE:
<223> OTHER INFORMATION: Synthesized Peptide.

<400> SEQUENCE: 197

```
Met Gly Ile Ile Met Cys Ile Ala Ile Ala Tyr Asp
1               5                   10
```

<210> SEQ ID NO 198
<211> LENGTH: 13
<212> TYPE: PRT
<213> ORGANISM: Artificial
<220> FEATURE:
<223> OTHER INFORMATION: Synthesized Peptide.

<400> SEQUENCE: 198

```
Met Gly Tyr Phe Trp Cys Phe Phe Trp Cys Ala Tyr Asp
```

<210> SEQ ID NO 199
<211> LENGTH: 17
<212> TYPE: PRT
<213> ORGANISM: Artificial
<220> FEATURE:
<223> OTHER INFORMATION: Synthesized Peptide.

<400> SEQUENCE: 199

Met Gly Tyr Phe Trp Cys Phe Phe Trp Cys Tyr Phe Tyr Cys Ala Tyr
1               5                   10                  15

Asp

<210> SEQ ID NO 200
<211> LENGTH: 13
<212> TYPE: PRT
<213> ORGANISM: Artificial
<220> FEATURE:
<223> OTHER INFORMATION: Synthesized Peptide.

<400> SEQUENCE: 200

Phe Ala Asn Ile Cys Ala Lys Ala Cys Trp Ala Tyr Asp
1               5                   10

<210> SEQ ID NO 201
<211> LENGTH: 20
<212> TYPE: PRT
<213> ORGANISM: Artificial
<220> FEATURE:
<223> OTHER INFORMATION: Synthesized Peptide.

<400> SEQUENCE: 201

Phe Val Thr Ala Cys Arg Thr Phe Cys Trp Ala Tyr Asp Tyr Lys Asp
1               5                   10                  15

Asp Asp Asp Lys
            20

<210> SEQ ID NO 202
<211> LENGTH: 20
<212> TYPE: PRT
<213> ORGANISM: Artificial
<220> FEATURE:
<223> OTHER INFORMATION: Synthesized Peptide.

<400> SEQUENCE: 202

Phe Val Cys Ala Cys Asn Cys Phe Cys Trp Ala Tyr Asp Tyr Lys Asp
1               5                   10                  15

Asp Asp Asp Lys
            20

<210> SEQ ID NO 203
<211> LENGTH: 20
<212> TYPE: PRT
<213> ORGANISM: Artificial
<220> FEATURE:
<223> OTHER INFORMATION: Synthesized Peptide.

<400> SEQUENCE: 203

Phe Val Cys Ala Cys Gln Cys Phe Cys Trp Ala Tyr Asp Tyr Lys Asp
1               5                   10                  15

Asp Asp Asp Lys
            20

```
<210> SEQ ID NO 204
<211> LENGTH: 20
<212> TYPE: PRT
<213> ORGANISM: Artificial
<220> FEATURE:
<223> OTHER INFORMATION: Synthesized Peptide.

<400> SEQUENCE: 204

Phe Val Cys Ala Cys Arg Cys Phe Cys Trp Ala Tyr Asp Tyr Lys Asp
1               5                   10                  15

Asp Asp Asp Lys
            20

<210> SEQ ID NO 205
<211> LENGTH: 20
<212> TYPE: PRT
<213> ORGANISM: Artificial
<220> FEATURE:
<223> OTHER INFORMATION: Synthesized Peptide.

<400> SEQUENCE: 205

Phe Val Cys Ala Cys His Cys Phe Cys Trp Ala Tyr Asp Tyr Lys Asp
1               5                   10                  15

Asp Asp Asp Lys
            20

<210> SEQ ID NO 206
<211> LENGTH: 20
<212> TYPE: PRT
<213> ORGANISM: Artificial
<220> FEATURE:
<223> OTHER INFORMATION: Synthesized Peptide.

<400> SEQUENCE: 206

Phe Val Cys Ala Cys Asp Cys Phe Cys Trp Ala Tyr Asp Tyr Lys Asp
1               5                   10                  15

Asp Asp Asp Lys
            20

<210> SEQ ID NO 207
<211> LENGTH: 20
<212> TYPE: PRT
<213> ORGANISM: Artificial
<220> FEATURE:
<223> OTHER INFORMATION: Synthesized Peptide.

<400> SEQUENCE: 207

Phe Ala Asn Ile Cys Lys Ala Asn Cys Trp Ala Tyr Asp Tyr Lys Asp
1               5                   10                  15

Asp Asp Asp Lys
            20

<210> SEQ ID NO 208
<211> LENGTH: 20
<212> TYPE: PRT
<213> ORGANISM: Artificial
<220> FEATURE:
<223> OTHER INFORMATION: Synthesized Peptide.

<400> SEQUENCE: 208

Phe Ala Asn Ile Cys Ala Lys Ala Cys Trp Ala Tyr Asp Tyr Lys Asp
1               5                   10                  15

Asp Asp Asp Lys
            20
```

METHOD FOR PRODUCING COMPOUND CONTAINING HETEROCYCLE

TECHNICAL FIELD

The present invention relates to a method for producing a heterocycle-containing compound, and the like.

BACKGROUND ART

In recent years, various peptides have attracted attentions as a drug candidate or research tool. There have been various attempts to develop a peptide library and screen peptides having affinity with a target substance.

As a method of artificially constructing a peptide library, a method using chemical synthesis, a method using a biosynthetic enzyme of a secondary metabolite, a translation synthesis system, and the like have been used conventionally.

It is however difficult to enhance the diversity of a library in the method using chemical synthesis. In addition, it takes time for screening or analyzing the relationship between the structure and activity of a compound.

The method using a biosynthetic enzyme of a secondary metabolite, on the other hand, permits rapid and convenient construction or chemical conversion of an elaborate backbone that cannot be achieved by the chemical synthesis method. Since enzymes have substrate specificity, however, kinds of compounds that can be synthesized are limited. This method is therefore not suited for use in the construction of a large-scale compound library.

When a translation system is used, a peptide library rich in diversity can be constructed in a short time by constructing an mRNA library and translating it in one pot. By using this system in combination with an mRNA display method or the like, a nucleic acid molecule which is a genotype and a peptide which is a phenotype can be associated with each other. A peptide that binds to a desired target molecule can be speedily and conveniently searched from the library and concentrated. Although synthesis of a peptide library by using such a translation system has many advantages, it can produce only peptidic compounds.

In screening using a library, identification of a compound that inhibits a target substance having protease activity is often required. The library of peptidic compounds is however cleaved by protease so that compounds that inhibit the activity of a target substance cannot be screened efficiently.

Each peptide of the peptide library may be modified in vitro with a post-translational modification enzyme, but an enzyme having desired activity does not always have activity in vitro. Furthermore, the expressed peptide library must be purified before the reaction with an enzyme and in addition, substrate specificity of the enzyme must be investigated so that it is not easy to obtain a library composed of peptides having a desired structure.

When the presence or absence, or degree of modification of a library is not known, the library is regarded to be inferior in usefulness because it needs correlation analysis between structure and activity as in the chemical synthesis system.

Patellamide produced by Prochloron didemni, that is, endozoic algae of sea squirt is a low molecular cyclic peptide which is presumed to have various physiological activities. It is biosynthesized via a unique pathway with products of a pat gene cluster consisting of patA to patG. The pat gene cluster and biosynthesis pathway of it are schematically shown in FIG. 6.

In this biosynthesis, PatE peptide which is a patE gene product becomes a precursor. Since the patE gene has a hypervariable region (cassette region), the product of it constructs a natural combinatorial library.

The PatE peptide has, on both sides of the cassette region thereof, a recognition sequence by a post-translational modification enzyme. The proteins which serve as the post-translational modification enzyme are PatA, PatD, and PatG. PatD introduces an azoline backbone into Cys, Ser, and Thr in the cassette of PatE and converts Cys into a thiazoline backbone and Ser and Thr into an oxazoline backbone.

PatA cleaves the N-terminal recognition sequence of the cassette region of the PatE.

PatG is composed of two domains. An N-terminal oxidase domain converts an azoline backbone introduced by PatD into an azole backbone, that is, converts a thiazoline backbone into a thiazole backbone. A C-terminal peptidase domain macrocyclizes, while cleaving a C-terminal recognition sequence of the cassette region of PatE.

The cassette regions of the above-described natural PatE have following similarities: (i) they are composed of 7 or 8 residues, (ii) they tend to have Ser/Thr/Cys to be modified at the 2nd, 4th, 6th, or 8th positions from the N-terminal of the cassette region, (iii) the residues (Ser/Thr/Cys) to be modified are not adjacent to each other in most cases, and (iv) many of the residues other than Ser/Thr/Cys are hydrophobic residues such as Val, Ala, Ile, Phe, and Leu (M. S. Donia et al.; Non-patent Document 1).

These similarities were presumed to be necessary for it becoming a substrate of PatD or PatG, a post-translational modification enzyme. It is however not known which residue of Ser, Thr, and Cys has been modified or not modified and substrate specificity of PatD and PatG has not been elucidated yet.

The present inventors have found that some of azoline backbone introducing enzymes have azoline backbone forming activity also in vitro; the sequence of the cassette region which becomes a substrate of such an azoline backbone-introducing enzyme is not limited to that described in Non-patent Document 1 but the cassette region can have various sequences; an azoline compound library can therefore be constructed efficiently in one pot by expressing a PatE library in a cell-free translation system and then modifying it with the azoline backbone introducing enzyme; and such a library can be used also for screening using a target substance having protease activity. A schematic view of an azoline backbone formation reaction of such a substrate having a leader sequence is shown in FIG. 1A.

The present inventors have confirmed further that even when PatE has, instead of the leader sequence or recognition sequence thereof, a predetermined sequence different from the natural sequence, it may become a substrate of an azoline backbone introducing enzyme; and as shown in FIG. 1B, even when a peptide separate from a cassette-region-containing peptide is used as a leader sequence portion, presence of such peptide in a reaction system containing an azoline backbone introducing enzyme permits introduction of an azoline backbone into the cassette region (according to Patent Document 1).

CITATION LIST

Patent Document

Patent Document 1: WO/2012/121392

Non-Patent Document

Non-patent Document 1: Donia, M. S. et al., Nat. Chem. Biol., 2006, 2:729-735.

DISCLOSURE OF THE INVENTION

Problem to be Solved by the Invention

The method disclosed in Patent Document 1 was very useful for cyclization of a peptide or the like because by removing leader sequence from a substrate peptide, an arbitrary amino acid or analog thereof can be placed at the N terminal of the substrate peptide.

This method however needs addition, to a reaction system, of a leader sequence as a peptide separate from a substrate peptide and it complicates the library thus obtained. Further, when a leader sequence is added as a separate peptide, an azoline backbone is not always introduced sufficiently.

An object of the present invention is therefore stable introduction of an azoline backbone into a substrate peptide.

Means for Solving the Problems

The present inventors have proceeded with their research in order to solve the above problems. As a result, it has been found that the leader sequence of a substrate contributes to activation of an azoline backbone introducing enzyme.

It has also been found that when the leader sequence is bound to an azoline backbone introducing enzyme, the azoline backbone introducing enzyme is always activated sufficiently and as shown in FIG. 1C, a heterocycle such as an azoline cycle can be introduced into a substrate peptide having no leader sequence. It has been confirmed that the leader sequence bound to the N terminal of an azoline backbone introducing enzyme particularly highly activates the enzyme and the leader sequence bound to the azoline backbone introducing enzyme via a spacer having a certain length is more effective.

It has been confirmed further that using an azoline backbone introducing enzyme to which a leader sequence has been bound can shorten, in a substrate peptide, two recognition sequences sandwiching therebetween a cassette sequence and at the same time, diversify the cassette sequence; by placing an amino acid or an amino acid analog necessary for cyclization at the N terminal of the substrate peptide, the peptide having a heterocycle introduced therein can be cyclized efficiently; and a library obtained by using the azoline backbone introducing enzyme to which the leader sequence has been bound has a constitution simple and easy to handle, leading to completion of the present invention.

The present invention relates to:

[1] a method for producing a compound having a heterocycle introduced by an azoline backbone introducing enzyme, including:
preparing a peptide represented by the following formula (I):

$$(Xaa_2)m\text{-}(Xaa_3)n\text{-}(Xaa_4)o \qquad (I)$$

[wherein,
$(Xaa_2)m$ represents m numbers of arbitrary amino acids and m represents an integer selected from 0 to 10;
$(Xaa_3)n$ represents n numbers of arbitrary amino acids, at least one of which is an amino acid selected from the group consisting of Cys, Ser, Thr, 2,3-diamino acids, homocysteine, homoserine, and 2,4-diamino acids, and analogs thereof, and n represents an integer selected from 2 to 40; and
$(Xaa_4)o$ represents o numbers of arbitrary amino acids and o represents an integer selected from 0 to 10], and
reacting the peptide with an azoline backbone introducing enzyme to which a leader sequence of a substrate or a partial sequence thereof has been bound to introduce a heterocycle into at least one of Cys, Ser, Thr, 2,3-diamino acids, homocysteine, homoserine, and 2,4-diamino acids, and analogs thereof of $(Xaa_3)n$;

[2] the method described above in [1], wherein the azoline backbone introducing enzyme has an N terminal to which the leader sequence of a substrate or the partial sequence thereof has been bound;

[3] the method as described above in [1] or [2], wherein the leader sequence or the partial sequence thereof has the following sequence: MNKKNILPQQGQPVIRLT-AGQLSSQLAELSEEALGDA (SEQ ID NO: 1) MKEQNSFNLLQEVTESELDLILGA (SEQ ID NO: 2) MILASLSTFQQMWISKQEYDEAGDA (SEQ ID NO: 3) MELQLRPSGLEKKQAPISELNIAQTQGGDSQVLA-LNA (SEQ ID NO: 4); or a partial sequence thereof;

[4] the method as described above in any one of [1] to [3], wherein the leader sequence has been bound to the azoline backbone introducing enzyme via a spacer:

[5] the method as described above in any one of [1] to [4], wherein the $(Xaa_3)n$ is $(Xaa_5\text{-}Xaa_6)p$:
[wherein, p numbers of $Xaa_5$ each independently represent an arbitrary amino acid, p numbers of $Xaa_6$ each independently represent an amino acid selected from the group consisting of Cys, Ser, Thr, 2,3-diamino acids, homocysteine, homoserine, and 2,4-diamino acids, and analogs thereof, and p is selected from 1 to 20];

[6] the method as described above in [5], wherein the $Xaa_6$ is Cys;

[7] the method as described above in any of [1] to [6], wherein the $(Xaa_4)o$ contains, at the N terminal thereof, Ala-Tyr-Asp;

[8] the method as described above in any of [1] to [7], wherein the step of preparing a peptide represented by the formula (I) includes:
preparing a nucleic acid encoding the peptide represented by the formula (I), and
translating the nucleic acid in a cell-free translation system;

[9] the method as described above in [1] to [8], wherein the peptide represented by the formula (I) contains an amino acid used for cyclization;

[10] the method as described above in [9], wherein the peptide represented by the formula (I) contains an amino acid having any of functional groups in the following Functional group 1 and an amino acid having a functional group corresponding thereto in the following Functional group 2;

TABLE 1

| Functional group 1 | Functional group 2 |
|---|---|
| (A) $-\overset{O}{\underset{\|}{C}}-\underset{H_2}{C}-X_1$ (A-1) | HS— (A-2) |

TABLE 1-continued

| | Functional group 1 | Functional group 2 |
|---|---|---|
| (B) | —C≡C—H (B-1) | $N_3$— (B-2) |
| (C) | —Ar—$CH_2NH_2$ (C-1) | 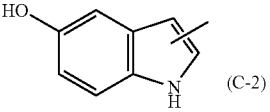 (C-2) |
| (D) | —C≡C—$CH_2$—$X_1$ (D-1) | HS— (D-2) |
| (E) | —Ar—$CH_2$—$X_1$ (E-1) | HS— (E-2) |

[wherein, $X_1$ represents Cl, Br, or I and Ar represents a substituted or unsubstituted aromatic ring];

[11] the method as described above in any one of [1] to [10], further including, after the step of introducing a heterocycle, cyclizing the heterocycle-containing compound;

[12] a method for producing a compound containing a heterocycle introduced by an azole backbone introducing enzyme, including after the step of introducing a heterocycle in the method as described above in any one of [1] to [11]:
reacting the peptide having a heterocycle introduced therein with the azole backbone introducing enzyme and thereby converting at least one of the heterocycles introduced by the azoline backbone introducing enzyme into a heterocycle introduced by the azole backbone introducing enzyme;

[13] a heterocycle-containing compound produced by the method described above in any one of [1] to [12];

[14] an azoline backbone introducing enzyme which is any of the following enzymes:
(i) an enzyme having an amino acid sequence represented by any one of SEQ ID NO: 5 to 15,
(ii) an enzyme having a sequence having 80% or more identity with any one of SEQ ID NO: 5 to 15 and having azoline backbone introducing activity, and
(iii) an enzyme having a sequence obtained by deletion, addition, or substitution of one or more amino acids in any one of SEQ ID NO: 5 to 15 and having azoline backbone introducing activity;

[15] a method of constructing a library including two or more compounds containing a heterocycle introduced by an azoline backbone introducing enzyme, including:
in the step of preparing a peptide in the method as described above in any one of [1] to [11], preparing a peptide library including two or more peptides represented by the formula (I) but different in (Xaa$_3$)n and, in the step of introducing a heterocycle by an azoline backbone introducing enzyme in the above-described method, introducing the heterocycle in the peptide library,
wherein the step of preparing a peptide library includes constructing a nucleic acid library encoding the peptide library and translating the nucleic acid library in a cell-free translation system to construct the peptide library;

[16] a method of constructing a library including two or more compounds containing a heterocycle introduced by an azoline backbone introducing enzyme, including:
in the step of preparing a peptide in the method as described above in any one of [1] to [11], preparing a peptide library including a complex of two or more peptides represented by the formula (I) but different in (Xaa$_3$)n and mRNAs encoding the peptides, and in the step of introducing a heterocycle by an azoline backbone introducing enzyme in the above-described method, introducing the heterocycle in the peptide library,
wherein the step of preparing a peptide library includes constructing an mRNA library encoding the peptide library, binding puromycin to the 3' end of each of the mRNAs to construct a puromycin-bound mRNA library, and translating the puromycin-bound mRNA library in a cell-free translation system to construct a peptide-mRNA complex library;

[17] a method of constructing a library including two or more compounds containing a heterocycle introduced by an azole backbone introducing enzyme, including:
constructing a library including two or more compounds containing a heterocycle introduced by an azoline backbone introducing enzyme by the method as described above in [15] or [16], and
reacting the library with the azole backbone introducing enzyme to convert at least one of the heterocycles introduced by the azoline backbone introducing enzyme into a heterocycle introduced by the azole backbone introducing enzyme;

[18] a screening method for identifying a compound containing a heterocycle that binds to a target substance, including:
bringing a compound library constructed by the method as described above in any of [15] to [17] into contact with the target substance and then incubating; and
selecting the compound that has bound to the target substance; and

[19] a screening kit for identifying a compound containing a heterocycle that binds to a target substance, including:
a compound library constructed by the method as described above in any one of [15] to [17].

EFFECT OF THE INVENTION

According to the method of the present invention, an azoline backbone introducing enzyme can be activated constantly so that a heterocycle such as azoline ring can be introduced efficiently even into a substrate peptide having no leader sequence. A compound containing an intended heterocycle can therefore be obtained without carrying out an operation such as removal of an excess leader sequence after introduction of the heterocycle.

When a heterocycle-containing compound library is constructed using an azoline backbone introducing enzyme to which a leader sequence has been bound, reaction conditions for library construction can be simplified because the leader sequence is not added as an independent peptide. In addition, screening of an active species can be carried out without removing an excess leader sequence because the heterocycle-containing compound has no leader sequence. Further, the heterocycle-containing compound having no leader sequence facilitates arrangement designing for forming a macrocyclic backbone. If such a heterocycle-containing compound library is used for screening, a compound that binds to the target substance can be screened even when the target substance has protease activity.

Further, since the heterocycle-containing compound library can be used in the mRNA display method, a compound having binding activity to a target substance can be concentrated and the nucleic acid sequence encoding the peptide portion of the compound obtained can be identified easily.

BRIEF DESCRIPTION OF THE DRAWINGS

FIG. 2A shows respective amino acid sequences of examples of LS-fusion PatD (Ndel-LS-GS15-PatD (SEQ ID NO: 5) and Ndel-LS-GS35-PatD (SEQ ID NO: 6)).

FIG. 2B shows respective amino acid sequences of examples of LS-fusion PatD (Nhel-LS-GS5-PatD (SEQ ID NO: 7) and Nhel-LS-GS15-PatD (SEQ ID NO: 8)).

FIG. 2C shows respective amino acid sequences of examples of LS-fusion PatD (Nhel-LS-GS25-PatD (SEQ ID NO: 9) and Nhel-LS-GS35-PatD (SEQ ID NO: 10)).

FIG. 2D shows an amino acid sequence of an example of LS-fusion PatD (Nhel-LS-RS-GS35-PatD (SEQ ID NO: 11)).

FIG. 2E shows respective amino acid sequences of examples of LS-fusion PatD (PatD-GS5-LS (SEQ ID NO: 12) and PatD-GS15-LS (SEQ ID NO: 13).

FIG. 2F shows respective amino acid sequences of examples of LS-fusion PatD (PatD-GS25-LS (SEQ ID NO: 14) and PatD-GS35-LS (SEQ ID NO: 15)).

FIG. 4A shows the results of studying the modification of substrate peptides different in recognition sequence with LS-fusion PatD.

FIGS. 4B-1 shows the results of studying modification of substrate peptides different in recognition sequence with LS-fusion PatD.

FIG. 4B-2 shows the results of studying the modification of different cassette sequences and substrate peptides with LS-fusion PatD.

FIG. 4B-3 shows the results of studying the modification of different cassette sequences and substrate peptides with LS-fusion PatD.

FIG. 4D-1 shows the results of studying the modification of substrate peptides different in cassette sequence with the LS-fusion PatD.

FIG. 4D-2 shows the results of studying the modification of substrate peptides different in cassette sequence with the LS-fusion PatD.

FIG. 4D-3 shows the results of studying the modification of substrate peptides different in cassette sequence with the LS-fusion PatD.

FIG. 4D-4 shows the results of studying the modification of substrate peptides different in cassette sequence with the LS-fusion PatD.

FIG. 4E shows the results of studying the modification of substrate peptides different in cassette sequence with the LS-fusion PatD.

FIG. 4F shows the results of studying the modification of substrate peptides different in cassette sequence with the LS-fusion PatD.

FIG. 4G-1 shows the results of studying the modification of substrate peptides different in cassette sequence with the LS-fusion PatD.

FIG. 4G-2 shows the results of studying the modification of substrate peptides different in cassette sequence with the LS-fusion PatD.

FIG. 4H shows the results of studying the modification of substrate peptides different in cassette sequence with the LS-fusion PatD.

FIG. 5B-1 shows the results of studying the number of azoline rings in a cyclized compound.

FIG. 5B-2 shows the results of studying the number of azoline rings in a cyclized compound.

Figure 1A:
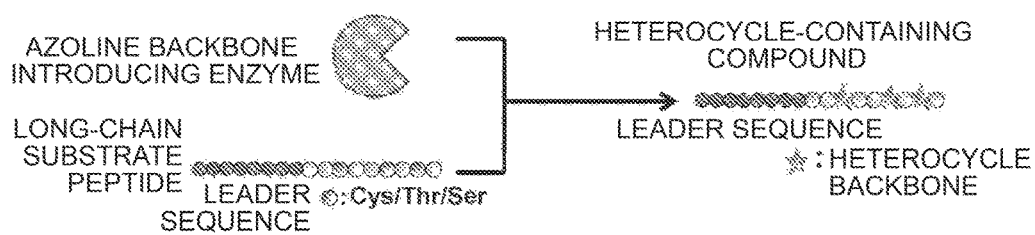
FIG. 1A shows a backbone conversion reaction of a wild type azoline backbone introducing enzyme with a wild type substrate having a leader sequence.

EMBODIMENT FOR CARRYING OUT THE INVENTION (Method for Producing Heterocycle-containing Compound [1])

The present invention provides a method of producing a compound containing a heterocycle introduced by an azoline backbone introducing enzyme.

The term "compound having a heterocycle introduced by an azoline backbone introducing enzyme" as used herein means a compound obtained by introducing, by an azoline backbone introducing enzyme, a heterocycle into at least one of Cys, Ser, Thr, 2,3-diamino acids, homocysteine, homoserine, and 2,4-diamino acids, and analogs thereof contained in $(Xaa_3)n$ of a peptide represented by the following formula (I):

$$(Xaa_2)m\text{-}(Xaa_3)n\text{-}(Xaa_4)o \qquad (I)$$

[wherein, $(Xaa_2)m$ represents m numbers of arbitrary amino acids and m represents an integer selected from 0 to 10;

$(Xaa_3)n$ represents n numbers of arbitrary amino acids, at least one of which is an amino acid selected from the group consisting of Cys, Ser, Thr, 2,3-diamino acids, homocysteine, homoserine, 2,4-diamino acids, homocysteine, homoserine, and 2,4-diamino acids, and analogs thereof, and n represents an integer selected from 2 to 40; and $(Xaa_4)o$ represents o numbers of arbitrary amino acids and o represents an integer selected from 0 to 10].

The term "amino acid" is used herein in the broadest meaning and includes, in addition to natural amino acids, derivatives thereof and artificial amino acids. Examples of the amino acid as described herein include natural proteinogenic L-amino acids, non-natural amino acids, and chemically synthesized compounds having properties known per se in the art and characteristic to amino acids. Examples of the non-natural amino acids include, but not limited to amino acids having main chain structure different from that of natural amino acids such as α,α-disubstituted amino acids (such as α-methylalanine), N-alkyl-α-amino acids, D-amino acids, β-amino acids, and α-hydroxy acids; amino acids having a side chain structure different from that of natural amino acids (norleucine, homohistidine, and the like); amino acids having excess methylene on the side chain thereof ("homo"amino acids, homophenylalanine, homohistidine, and the like); and amino acids obtained by substituting carboxylic acid functional group in the side chain thereof with a sulfonic acid group (such as cysteic acid).

The amino acids herein may be represented by commonly used single-letter or three-letter codes, respectively. The amino acids represented by single-letter or three-letter codes may include mutants or derivatives thereof.

In the formula (I), n numbers of $Xaa_3$ each independently represent an arbitrary amino acid insofar as it contains at least one Cys, Ser, Thr, 2,3-diamino acids, homocysteine, homoserine, or 2,4-diamino acids, or an analog thereof.

In the above formula, n is an integer selected from 2 to 40. Although n is not particularly limited, it may be from 2 to 30, 4 to 26, or the like.

Amino acids constituting $(Xaa_3)n$ may be, as well as a natural amino acid, a derivative thereof or an artificial amino acid. Although a process for preparing a peptide containing a derivative of a natural amino acid or an artificial amino acid is not particularly limited, a natural amino acid, a derivative thereof, or an artificial amino acid can be introduced into a peptide, for example, by carrying out reprogramming of a genetic code making use of a reconstruction type translation system and an artificial RNA aminoacylation catalyst "Flexizyme" developed by the present inventors (WO2007/066627, WO2012/026566).

The $(Xaa_3)n$ may be $(Xaa_5-Xaa_6)p$. In the formula, p numbers of $Xaa_5$ each independently represent an arbitrary amino acid and p numbers of $Xaa_6$ each independently represent an amino acid selected from the group consisting of Cys, Ser, Thr, 2,3-diamino acids, homocysteine, homoserine, and 2,4-diamino acids, and analogs thereof, and p represents an integer half of n and is selected from 1 to 20.

Such a constitution, in which Cys, Ser, Thr, a 2,3-diamino acids, homocysteine, homoserine, or a 2,4-diamino acids, or an analog thereof is located at an even-numbered one of $(Xaa_3)n$, facilitates introduction of a heterocycle such as azoline ring because of the properties of the azoline backbone introducing enzyme. The $Xaa_5$ may be Cys, Ser, Thr, a 2,3-diamino acids, homocysteine, homoserine, or a 2,4-diamino acids, or an analog thereof.

$Xaa_6$s may each be composed only of Cys into which an azoline backbone can be introduced easily.

Examples of the analog of Thr include, but not limited to, those represented by the following formula:

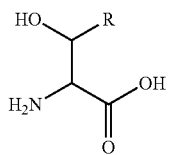

[Chemical formula 1]

[wherein, R represents a hydrogen atom or a substituted or unsubstituted alkyl group having from 1 to 10 carbon atoms, or a substituted or unsubstituted aromatic group].

Examples of the analog of Cys include, but not limited to, those represented by the following formula:

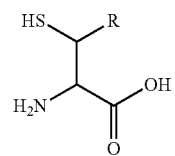

[Chemical formula 2]

[wherein, R represents a hydrogen atom or a substituted or unsubstituted alkyl group having from 1 to 10 carbon atoms, or a substituted or unsubstituted aromatic group].

Examples of the analog of Ser and Thr include, but not limited to, those represented by the following formula:

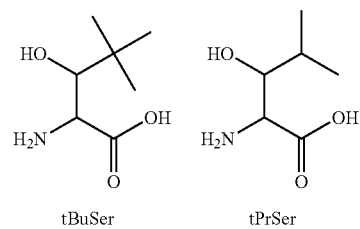

tBuSer    tPrSer

[Chemical formula 3]

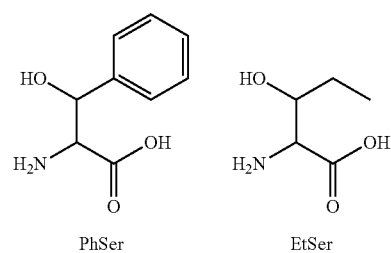

PhSer    EtSer

Examples of the 2,3-diamino acids and analog thereof include, but not limited to, those represented by the following formula:

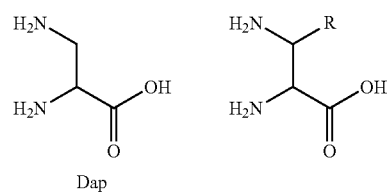

Dap

[Chemical formula 4]

[wherein, R represents a hydrogen atom or a substituted or unsubstituted alkyl group having from 1 to 10 carbon atoms, or a substituted or unsubstituted aromatic group].

Examples of the homocysteine and analog thereof include, but not limited to, those represented by the following formula:

[Chemical formula 5]

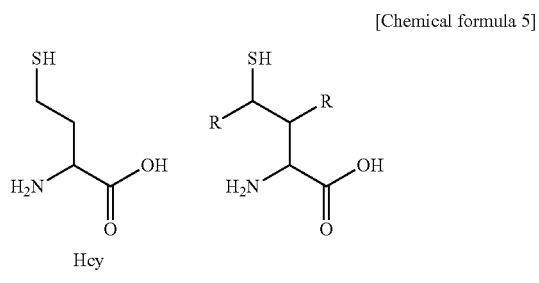

Hcy

[wherein, R represents a hydrogen atom or a substituted or unsubstituted alkyl group having from 1 to 10 carbon atoms, or a substituted or unsubstituted aromatic group].

Examples of homoserine and analog thereof include, but not limited to those represented by the following formula:

[Chemical formula 6]

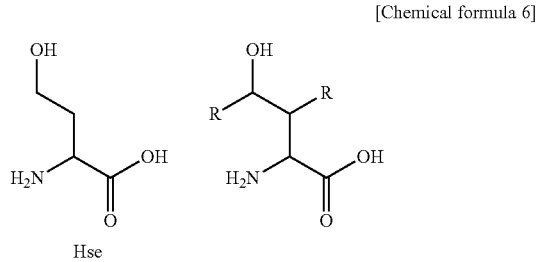

Hse

[wherein, R represents a hydrogen atom or a substituted or unsubstituted alkyl group having from 1 to 10 carbon atoms, or a substituted or unsubstituted aromatic group].

Examples of the 2,4-diamino acids and analog thereof include, but not limited to, those represented by the following formula:

[Chemical formula 7]

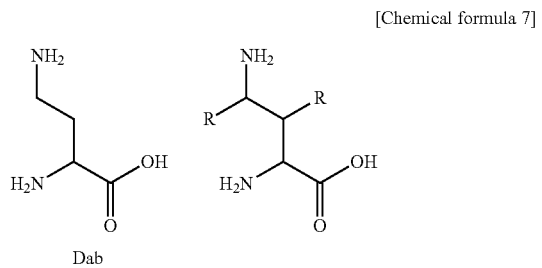

Dab

[wherein, R represents a hydrogen atom or a substituted or unsubstituted alkyl group having from 1 to 10 carbon atoms, or a substituted or unsubstituted aromatic group].

The term "introducing a heterocycle into at least one of Cys, Ser, Thr, 2,3-diamino acids, homocysteine, homoserine, 2,4-diamino acids, and analogs thereof" as used herein means introducing an azoline ring, a dihydrothiazine ring, a dihydroxazine ring, or a dihydropyrimidine ring represented by the following formula by a dehydration reaction at Cys, Ser, Thr, a 2,3-diamino acid, homocysteine, homoserine, or a 2,4-diamino acid as a result of the reaction with an azoline backbone introducing enzyme.

[Chemical formula 8]

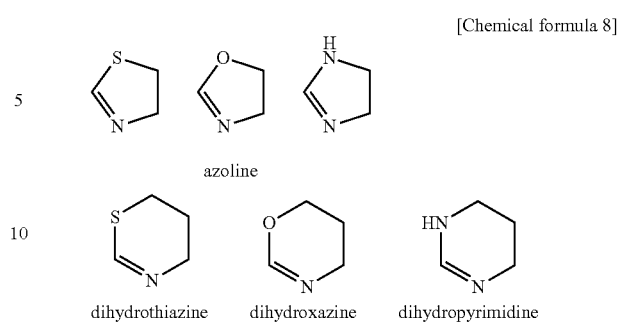

Introduction of a heterocycle into Ser, Thr, Cys, 2,3-diaminopropionic acid, homocysteine, homoserine, or 2,3-diaminobutyric acid produces an oxazoline, thiazoline, or imidazoline backbone as shown below, respectively.

Ser:

[Chemical formula 9]

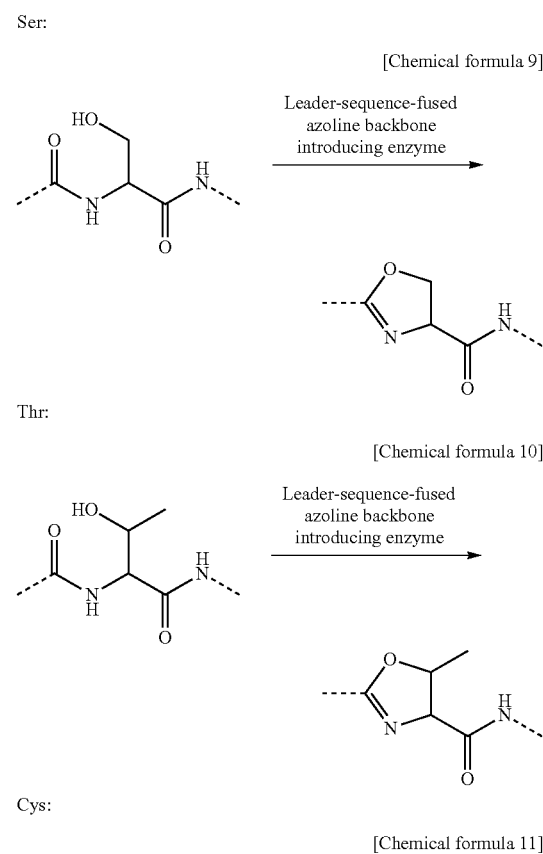

Thr:

[Chemical formula 10]

Cys:

[Chemical formula 11]

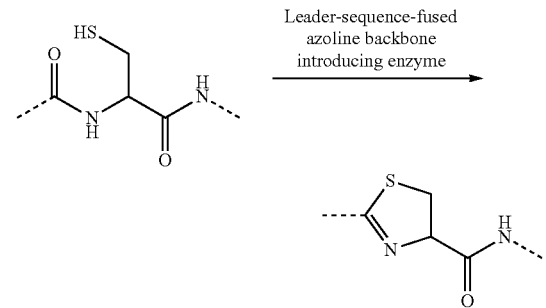

-continued 2,3-Diaminopropionic acid:

[Chemical formula 12]

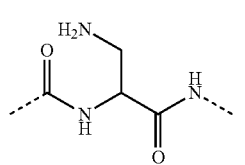

Leader-sequence-fused azoline backbone introducing enzyme →

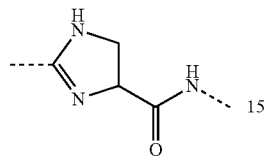

Homocysteine:

[Chemical formula 13]

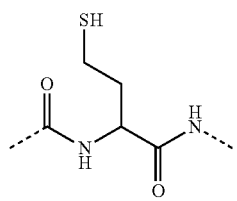

Leader-sequence-fused azoline backbone introducing enzyme →

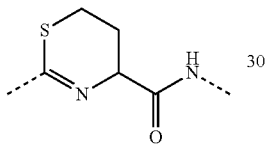

Homoserine:

[Chemical formula 14]

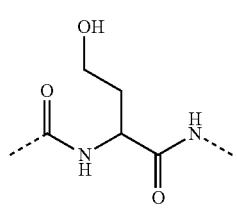

Leader-sequence-fused azoline backbone introducing enzyme →

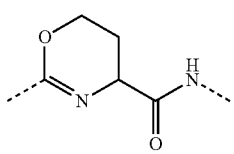

2,3-Diaminobutyric acid

[Chemical formula 15]

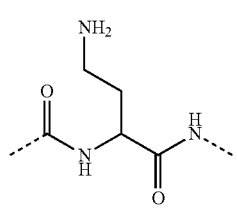

Leader-sequence-fused azoline backbone introducing enzyme →

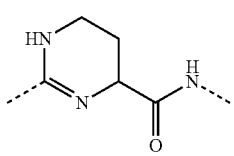

For example, introduction of a heterocycle into the above-mentioned Thr analog residue produces the following oxazoline backbone.

[Chemical formula 16]

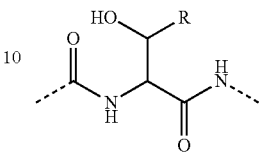

Leader-sequence-fused azoline backbone introducing enzyme →

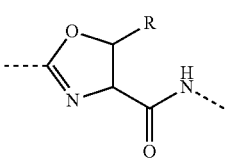

Introduction of a heterocycle into the above-mentioned Cys analog residue produces the following thiazoline backbone.

[Chemical formula 17]

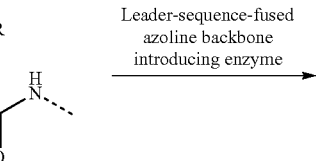

Leader-sequence-fused azoline backbone introducing enzyme →

Introduction of a heterocycle into the above-mentioned 2,3-diamino acid analog residue produces the following imidazoline backbone.

[Chemical formula 18]

Leader-sequence-fused azoline backbone introducing enzyme →

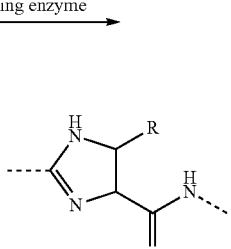

Introduction of a heterocycle into the above-mentioned homocysteine analog residue produces the following dihydrothiazine backbone.

[Chemical formula 19]

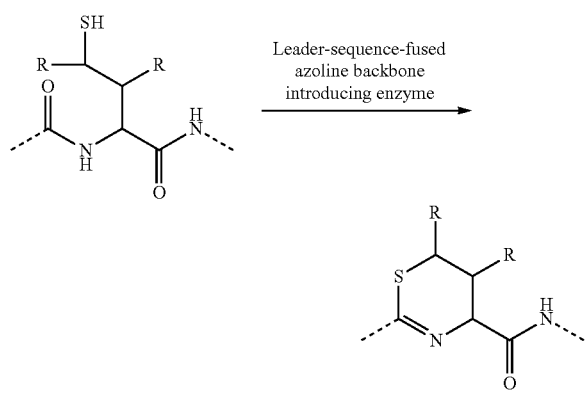

Introduction of a heterocycle into the above-mentioned homoserine analog residue produces the following dihydroxazine backbone.

[Chemical formula 20]

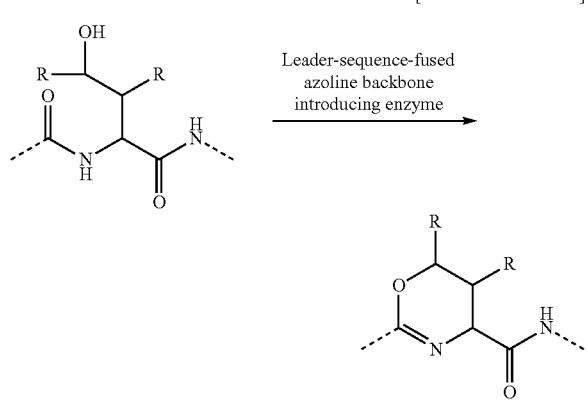

Introduction of a heterocycle into the above-mentioned 2,4-diamino acid analog residue produces the following dihydropyrimidine backbone.

[Chemical formula 21]

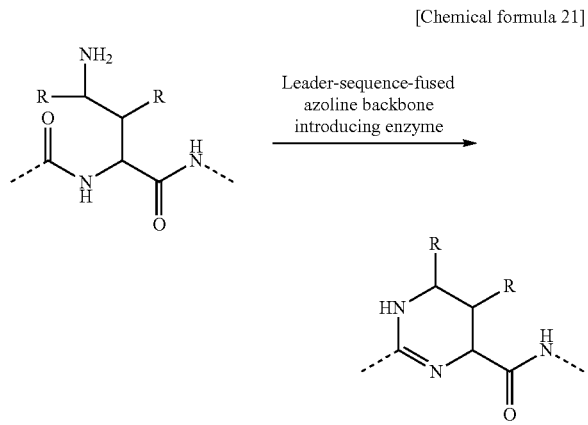

In $(Xaa_3)n$, Cys, Ser, Thr, 2,3-diamino acids, homocysteine, homoserine, or 2,4-diamino acids, or analog thereof has preferably no hydrophilic amino acid adjacent to the N-terminal side thereof. As shown later in Examples, a heterocycle is likely to be introduced when Cys, Ser, Thr, 2,3-diamino acids, homocysteine, homoserine, or 2,4-diamino acids, or analog thereof has no hydrophilic amino acid adjacent to the N-terminal side thereof.

The term "hydrophilic amino acid" as used herein means, but not limited to, Asp, Glu, Arg, Lys, Asn, or Gln, or a hydrophilic derivative thereof.

In the formula (I), o numbers of $Xaa_4$s each independently represent an arbitrary amino acid and they may have any sequence insofar as the peptide represented by the formula (I) becomes a substrate of an azoline backbone introducing enzyme. In the formula, o represents an arbitrary integer selected from 0 to 10 and it may be, for example, from 1 to 5 or 1 to 3. The $(Xaa_4)o$ may have, at the N terminal thereof, Ala-Tyr-Asp. $(Xaa_4)o$ may be composed only of Ala-Tyr-As. $(Xaa_4)o$ may contain, in addition to natural amino acids, derivatives thereof or artificial amino acids. A preparation method of a peptide containing a derivative of a natural amino acid or an artificial amino acid is not particularly limited, but a translation system using extension or reprogramming of genetic code can be used. As one example, usable is a method of extending/reprogramming the genetic code by making use of a cell-free translation system and an artificial RNA aminoacylation catalyst "Flexizyme" developed by the present inventors (WO2007/066627, WO2012/026566).

In the formula (I), m numbers of $Xaa_2$s each independently represent an arbitrary amino acid and they may have any sequence insofar as the peptide represented by the formula (I) becomes a substrate of an azoline backbone introducing enzyme. In the formula, m represents an arbitrary integer selected from 0 to 10 and it may be, for example, 0 or 1. $(Xaa_2)m$ may contain, in addition to natural amino acids, derivatives thereof or artificial amino acids. A preparation method of a peptide containing a derivative of a natural amino acid or an artificial amino acid is not particularly limited, but a translation system using extension or reprogramming of genetic code can be used. As one example, usable is a method of extending/reprogramming the genetic code by making use of a cell-free translation system and an artificial RNA aminoacylation catalyst "Flexizyme" developed by the present inventors (WO2007/066627, WO2012/026566).

No particular limitation is imposed on the process for preparing the peptide of the formula (I) and it can be prepared by a known process or a process equivalent thereto, for example, chemical synthesis such as liquid phase synthesis, solid phase synthesis, or hybrid synthesis using solid phase synthesis and liquid phase synthesis in combination, genetic recombination or synthesis using cell-free translation system.

When the cell-free translation system is used, the peptide of the formula (I) can be obtained by preparing a nucleic acid encoding the peptide and then translating the nucleic acid in the cell-free translation system. The nucleic acid encoding the peptide represented by the formula (I) can be designed as needed by those skilled in the art by using a genetic code used in the translation system of living organism or a reprogrammed genetic code, or a combination thereof. The nucleic acid may be either DNA or RNA.

In the cell-free translation system, using non-natural aminoacyl tRNA permits use of not only natural amino acids but also derivatives thereof or artificial amino acids. For example, the artificial RNA aminoacilation catalyst "Flexizyme" developed by the present inventors can be used.

In the cell-free translation system, the N-terminal amino acid of $(Xaa_2)m$ of the formula (I) (which will hereinafter be called "Xaa₁") is used as an amino acid encoded by a start codon. In the translation system of living organism, a start codon AUG encodes fMet and Met in prokaryotic cells and eukaryotic cells, respectively. On the other hand, using non-natural aminoacyl initiation tRNA enables use of an arbitrary start amino acid. For example, by using a cell-free translation system and an artificial RNA aminoacylation catalyst "Flexizyme" developed by the present inventors, a genetic code composed of triplets of mRNA can be reprogrammed so that it encodes an amino acid different from that of the translation system of living microorganism (WO2008/059823).

As the cell-free translation system, an *Escherichia coli* extract or wheat germ extract may be used. A rabbit erythrocyte extract or insect cell extract may also be used. A re-constituted cell-free translation system may be used, which is obtained by reconstituting, after purification, ribosome protein, aminoacyl tRNA synthetase (ARS), ribosome RNA, amino acid, rRNA, GTP, ATP, translation initiation factor (IF), extension factor (EF), release factor (RF), ribosome regeneration factor (RRF), and other factors necessary for translation.

From several hundred micrograms to several milligram/mL of proteins can be produced by continuously supplying the system containing these factors with energy under dialysis. The system may contain an RNA polymerase for performing transcription from DNA. Examples of the commercially available cell-free translation systems usable here include *E. coli*-derived systems such as "RTS-100" (registered trademark), product of Roche Diagnostics, reconstituted translation systems such as "PURESYSTEM" (registered trademark), product of PGI, and PURExpressR In Vitro Protein Synthesis Kit, product of New England BioLabs, and systems using a wheat germ extract available from ZOEGENE Corporation and CellFree Sciences Co., Ltd.

As a system using ribosome of *Escherichia coli*, for example, the technology described in the following documents are known: H. F. Kung et al., 1977. The Journal of Biological Chemistry Vol. 252, No. 19, 6889-6894; M. C. Gonza et al., 1985, Proceeding of National Academy of Sciences of the United States of America Vol. 82, 1648-1652; M. Y. Pavlov and M. Ehrenberg, 1996, Archives of Biochemistry and Biophysics Vol. 328, No. 1, 9-16; Y. Shimizu et al., 2001, Nature Biotechnology Vol. 19, No. 8, 751-755; H. Ohashi et al., 2007, Biochemical and Biophysical Research Communications Vol. 352, No. 1, 270-276.

By the cell-free translation system, a high purity product can be obtained without purifying the expressed product.

Flexizyme is, on the other hand, an artificial RNA catalyst (an RNA catalyst having acyl tRNA synthetase-like activity) capable of binding (acylating) an arbitrary amino acid or hydroxy acid to an arbitrary tRNA. In a reconstituted translation system, when Flexizyme is used instead of natural aminoacyl tRNA synthetases, a desired amino acid or hydroxy acid can be associated to an arbitrary codon, which is different from that in a natural genetic code.

As the Flexizyme, for example, those described in the following documents are known: H. Murakami, H. Saito, and H. Suga, (2003), Chemistry & Biology, Vol. 10, 655-662; H. Murakami, D. Kourouklis, and H. Suga, (2003), Chemistry & Biology, Vol. 10, 1077-1084; H. Murakami, A. Ohta, H. Ashigai, H. Suga (2006) Nature Methods 3, 357-359; N. Niwa, Y. Yamagishi, H. Murakami, H. Suga (2009) Bioorganic & Medicinal Chemistry Letters 19, 3892-3894; and WO2007/066627 "Multi-purpose acylation catalyst and use thereof". Flexizymes are also known to include original flexizyme (Fx) and modified ones such as dinitrobenzyl flexizyme (dFx), enhanced flexizyme (eFx), and amino flexizyme (aFx).

As a method of binding an arbitrary amino acid to an arbitrary tRNA, not only a method using a flexizyme but also another method can be used in the present invention.

For genetic code reprogramming, usable is a translation system which is made by arbitrarily removing the components from a translation system and reconstituting only necessary components, according to the purpose. For example, when a translation system is reconstituted after removal of a specific amino acid, the codon corresponding to the amino acid becomes a vacant codon. An arbitrary amino acid is bound to a tRNA having an anticodon complementary to the vacant codon by making use of a Flexizyme or the like, followed by translation. As a result, the arbitrary amino acid is coded by such codon and a peptide having the desired amino acid introduced therein instead of the removed amino acid is translated.

By using this method, any of amino acids of the peptide represented by the formula (I) can be used for macrocyclization of the peptide. In this method, $Xaa_1$ may be not Met but an arbitrary amino acid so that $Xaa_1$ may be used as an amino acid to be used for cyclization.

The amino acid to be used for macrocyclization may be contained in any of $(Xaa_2)m$, $(Xaa_3)n$, and $(Xaa_4)o$. An amino acid having a heterocycle introduced therein may be one of amino acids constituting a macrocycle or one of amino acids not constituting a macrocycle.

A macrocyclization method is not particularly limited, but macrocyclization may be performed, for example, by incorporating, in the peptide represented by the formula (I), an amino acid having the following functional group 1 and an amino acid having the following functional group 2 corresponding thereto. Either of the functional group 1 or the functional group 2 may be on the N-terminal side.

For example, a cyclization reaction can be performed after expressing the peptide represented by the formula (I) that includes an amino acid having the following functional group 1 as any of amino acids of $Xaa_2s$ and an amino acid having the functional group 2 corresponding thereto in $(Xaa_4)o$. Alternatively, an amino acid having the functional group 2 may be used as any of amino acids of $Xaa_2s$ and an amino acid having the functional group 1 corresponding thereto may be incorporated in $(Xaa_4)o$.

TABLE 2

| | Functional group 1 | Functional group 2 |
|---|---|---|
| (A) | 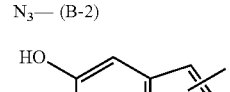 (A-1) | HS— (A-2) |
| (B) | —C≡C—H (B-1) | $N_3$— (B-2) |
| (C) | —Ar—CH₂NH₂ (C-1) | 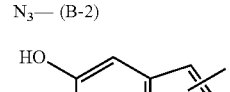 (C-2) |
| (D) | —C≡C—CH₂—X₁ (D-1) | HS— (D-2) |
| (E) | —Ar—CH₂—X₁ (E-1) | HS— (E-2) |

In the above formulas, $X_1$ represents Cl, Br, or I and Ar represents a substituted or unsubstituted aromatic ring.

As the amino acid (A-1), for example, a chloroacetylated amino acid can be used. Examples of the chloroacetylated amino acid include N-chloroacetyl-L-alanine, N-chloroacetyl-L-phenylalanine, N-chloroacetyl-L-tyrosine, N-chloroacetyl-L-tryptophan, N-3-(2-chloroacetamido)benzoyl-L-phenylalanine, N-3-(2-chloroacetamido)benzoyl-L-tyrosine, N-3-(2-chloroacetamido)benzoyl-L-tryptophane, β-N-chloroacetyl-L-diaminopropanoic acid, γ-N-chloroacetyl-L-diaminobutyric acid, σ-N-chloroacetyl-L-ornithine, and ε-N-chloroacetyl-L-lysine, and D-amino acid derivatives corresponding thereto.

Examples of the amino acid (A-2) include cysteine, homocysteine, mercaptonorvaline, mercaptonorleucine, 2-amino-7-mercaptoheptanoic acid, 2-amino-8-mercaptooctanoic acid, amino acids obtained by protecting the SH group of these amino acids and then eliminating the protecting group, and D-amino acid derivatives corresponding thereto.

The cyclization method can be carried out based on the method described in Kawakami, T. et al., Nature Chemical Biology 5, 888-890 (2009); Yamagishi, Y. et al., ChemBioChem 10, 1469-1472 (2009); Sako, Y. et al., Journal of American Chemical Society 130, 7932-7934 (2008); Goto, Y. et al., ACS Chemical Biology 3, 120-129 (2008); and Kawakami T. et al, Chemistry & Biology 15, 32-42 (2008), and WO2008/117833.

Examples of the amino acid (B-1) usable include propargylglycine, homopropargylglycine, 2-amino-6-heptynoic acid, 2-amino-7-octynoic acid, and 2-amino-8-nonynoic acid. Further, 4-pentynoylated or 5-hexynoylated amino acids may be used. Examples of the 4-pentynoylated amino acids include N-(4-pentenoyl)-L-alanine, N-(4-pentenoyl)-L-phenylalanine, N-(4-pentenoyl)-L-tyrosine, N-(4-pentenoyl)-L-tryptophan, N-3-(4-pentynoylamido)benzoyl-L-phenylalanine, N-3-(4-pentynoylamido)benzoyl-L-tyrosine, N-3-(4-pentynoylamido)benzoyl-L-tryptophan, β-N-(4-pentenoyl)-L-diaminopropanoic acid, γ-N-(4-pentenoyl)-L-diaminobutyric acid, σ-N-(4-pentenoyl)-L-ornithine, and ε-N-(4-pentenoyl)-L-lysine, and D-amino acid derivatives corresponding thereto.

Examples of the amino acid (B-2) include azidoalanine, 2-amino-4-azidobutanoic acid, azidoptonorvaline, azidonorleucine, 2-amino-7-azidoheptanoic acid, and 2-amino-8-azidooctanoic acid. Azidoacetylated or 3-azidopentanoylated amino acids may be used. Examples of the azidoacetylated amino acids include N-azidoacetyl-L-alanine, N-azidoacetyl-L-phenylalanine, N-azidoacetyl-L-tyrosine, N-azidoacetyl-L-tryptophan, N-3-(4-pentynoylamido)benzoyl-L-phenylalanine, N-3-(4-pentynoylamido)benzoyl-L-tyrosine, N-3-(4-pentynoylamido)benzoyl-L-tryptophan, β-N-azidoacetyl-L-diaminopropanoic acid, γ-N-azidoacetyl-L-diaminobutyric acid, σ-N-azidoacetyl-L-ornithine, and ε-N-azidoacetyl-L-lysine, and D-amino acid derivatives corresponding thereto.

The cyclization method can be performed based on the method described, for example, in Sako, Y. et al., Journal of American Chemical Society 130, 7932-7934 (2008) or WO2008/117833.

Examples of the amino acid (C-1) include N-(4-aminomethyl-benzoyl)-phenylalanine ($_{AMB}$F) and 4-3-aminomethyl-tyrosine.

Examples of the amino acid (C-2) include 5-hydroxytryptophan ($W_{OH}$).

The cyclization method can be performed based on the method described, for example, in Yamagishi, Y. et al., ChemBioChem 10, 1469-1472 (2009) or WO2008/117833.

Examples of the amino acid (D-1) include 2-amino-6-chloro-hexynoic acid, 2-amino-7-chloro-heptynoic acid, and 2-amino-8-chloro-octynoic acid.

Examples of the amino acid (D-2) include cysteine, homocysteine, mercaptonorvaline, mercaptonorleucine, 2-amino-7-mercaptoheptanoic acid, and 2-amino-8-mercaptooctanoic acid, amino acids obtained by protecting the SH group of these amino acids and then eliminating the protecting group, and D-amino acid derivatives corresponding thereto.

The cyclization method can be performed based on the method described, for example, in WO2012/074129.

Examples of the amino acid (E-1) include N-3-chloromethylbenzoyl-L-phenylalanine, N-3-chloromethylbenzoyl-L-tyrosine, and N-3-chloromethylbenzoyl-L-tryptophane.

Examples of the amino acid (E-2) include cysteine, homocysteine, mercaptonorvaline, mercaptonorleucine, 2-amino-7-mercaptoheptanoic acid, and 2-amino-8-mercaptooctanoic acid, and amino acids obtained by protecting the SH group of these amino acids and then eliminating the protecting group, and D-amino acid derivatives corresponding thereto.

(Azoline Backbone Introducing Enzyme)

To the azoline backbone introducing enzyme to be used in the method of the present invention, a leader sequence of a substrate of the azoline backbone introducing enzyme or a partial sequence thereof has been bound.

The "azoline backbone introducing enzyme" as described herein includes PatD and enzymes having homology therewith. As the enzyme having homology with PatD, for example, those included in the report of Lee, etc. (Lee, S. W. et al., PNAS vol. 105, No. 15, 5879-5884, 2008) may be used, but it is not limited to them. The azoline backbone introducing enzyme may be a mutant insofar as it has azoline backbone introducing activity. The term "heterocyclase" as used herein has the same meaning as the term "azoline backbone introducing enzyme".

The term "leader sequence of a substrate of an azoline backbone introducing enzyme" as used herein means a leader sequence of a natural or non-natural substrate of an azoline backbone introducing enzyme. When the azoline backbone introducing enzyme is PatD, the following is a leader sequence of a natural substrate:

(SEQ ID NO: 1)
MNKKNILPQQGQPVIRLTAGQLSSQLAELSEEALGDA

As shown in Patent Document 1, PatD can introduce an azoline backbone into a substrate peptide even when a sequence different from a leader sequence of PatE which is conventionally known as the leader sequence is used. The "leader sequence of a substrate of an azoline backbone introducing enzyme" of the present invention includes such a sequence. Examples of the leader sequence different from that of PatE includes MKEQNSFNLLQEVTESELDLILGA (SEQ ID NO: 2) derived from another peptide (Lacticin 481 precursor), MILASLSTFQQMWISKQEYDEAGDA (SEQ ID NO: 3) derived from human actin, and MELQLRPSGLEKKQAPISELNIAQTQGGDSQVLALNA (SEQ ID NO: 4) obtained by shuffling the leader sequence of PatE.

As the leader sequence, a sequence having high alpha helicity may be used.

The "partial sequence of the leader sequence of a substrate of an azoline backbone introducing enzyme" as used herein includes a sequence having, in the amino acid sequence represented by SEQ ID NO: 1 to 4, four or more, five or more, or six or more successive amino acids and having activating capacity of the azoline backbone introducing enzyme.

The position of the partial sequence in SEQ ID NO: 1 to 4 is not particularly limited. For example, it may contain four amino acids, five amino acids, or six amino acids at the C terminal of the amino acid sequence of SEQ ID NO: 1 to 4, it may contain four amino acids, five amino acids, or six amino acids at the N terminal, or it may contain four amino acids, five amino acids, or six amino acids neither at the N terminal nor the C terminal insofar as it has activating capacity of the azoline backbone introducing enzyme.

Whether such a partial sequence of the leader sequence has capacity of activating the azoline backbone introducing enzyme or not can be confirmed by a known method, for example, by binding the azoline backbone introducing enzyme to a substrate peptide in the presence of the leader sequence.

The above-mentioned leader sequence or partial sequence thereof may be bound to any position of the azoline backbone introducing enzyme, but it is desirable to bind it to the N terminal of the enzyme. As shown in Examples, the sequence bound to the N terminal constantly activates the azoline backbone introducing enzyme and introduces the azoline backbone into the substrate peptide efficiently. A conceptual diagram of a backbone formation reaction by a leader-sequence-fusion azoline introducing enzyme is shown in FIG. 1C.

The leader sequence or partial sequence thereof may be bound to the azoline backbone introducing enzyme via a spacer. The spacer can be selected as needed by those skilled in the art. It is, for example, a peptide composed of from 1 to 50 amino acids, a peptide composed of from 2 to 40 amino acids, or a peptide composed of from 5 to 35 amino acids.

The spacer peptide may have any amino acid sequence insofar as it does not adversely affect a reaction between the azoline backbone introducing enzyme and the substrate peptide.

The azoline backbone introducing enzyme having a leader sequence bound thereto can be prepared in a known process or a process equivalent thereto. For example, such an enzyme can be obtained by synthesizing a nucleic acid encoding it and expressing the nucleic acid as a fusion peptide in *Escherichia coli* or the like. It can be obtained similarly when the leader sequence and the azoline backbone introducing enzyme have therebetween a spacer peptide.

Specific examples of the azoline backbone introducing enzyme of the present invention are shown in FIGS. 2A to F (SEQ ID NO: 5 to 15). In these lists, a portion surrounded by a frame is a leader sequence; a shaded portion is a spacer peptide, and an underlined portion is the sequence of the azoline backbone introducing enzyme.

Examples of the azoline backbone introducing enzyme of the present invention include those having the amino acid sequence shown in FIGS. 2A to F, those having a sequence identity of 80% or more, 85% or more, 90% or more, 95% or more, or 98% more with any one of the above-mentioned amino acid sequences and having azoline backbone introducing activity, and those obtained by deleting, adding, or substituting one, two, three, four, or from 5 to 10 amino acids of any one of these sequences and having azoline backbone introducing activity.

The reaction between the azoline backbone introducing enzyme and the peptide library can be carried out in a container where the peptide has been expressed, that is, in one pot, without purifying the peptide, by adding the leader-sequence-bound azoline backbone introducing enzyme. The reaction between the azoline backbone introducing enzyme and the peptide library can be carried out, for example, when the azoline backbone introducing enzyme is PatD, under the conditions selected as needed by those skilled in the art from the following ranges: final concentration of from 0.1 µM to 50 µM, a reaction temperature of from 4° C. to 45° C., a reaction time of from 5 minutes to 100 hours, and the like.

Confirmation of the reaction can be carried out by measuring a mass change by using, for example, MALDI-TOF-MS.

The present invention embraces a nucleic acid encoding the azoline backbone introducing enzyme of the present invention.

(Production Method of Heterocycle-Containing Compound [2])

The present invention embraces a method of producing a compound containing a heterocycle introduced by an azole backbone introducing enzyme.

A compound containing a heterocycle introduced by an azoline backbone introducing enzyme and a compound containing a heterocycle introduced by an azole backbone introducing enzyme may be called "heterocycle compound" collectively.

The method for producing a compound containing a heterocycle introduced by an azole backbone introducing enzyme of the present invention includes, after performing introducing a heterocycle in the above-mentioned method for producing a compound containing a heterocycle introduced by an azoline backbone introducing enzyme, reacting the heterocycle-introduced peptide with an azole backbone introducing enzyme to convert the heterocycle introduced into Cys, Ser, Thr, a 2,3-diamino acids, homocysteine, homoserine, or a 2,4-diamino acids, or an analog thereof, by the azoline backbone introducing enzyme, into a heterocycle introduced by the azole backbone introducing enzyme.

The term "compound containing a heterocycle introduced by an azole backbone introducing enzyme" as used herein means that in a heterocycle produced as a result of the dehydration reaction of Cys, Ser, Thr, a 2,3-diamino acids, homocysteine, homoserine, or a 2,4-diamino acids, or an analog thereof of the peptide represented by the formula (I) by the azoline backbone introducing enzyme, an oxidation reaction by the azole backbone introducing enzyme proceeds and a heterocycle such as azole backbone represented by the following formula is introduced:

[Chemical formula 22]

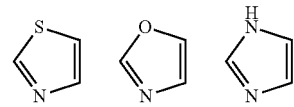

For example, introduction of an azole backbone into Ser, Thr, Cys, or a 2,3-diamino acids produces an oxazole, thiazole, or imidazole backbone as shown below:

Ser:

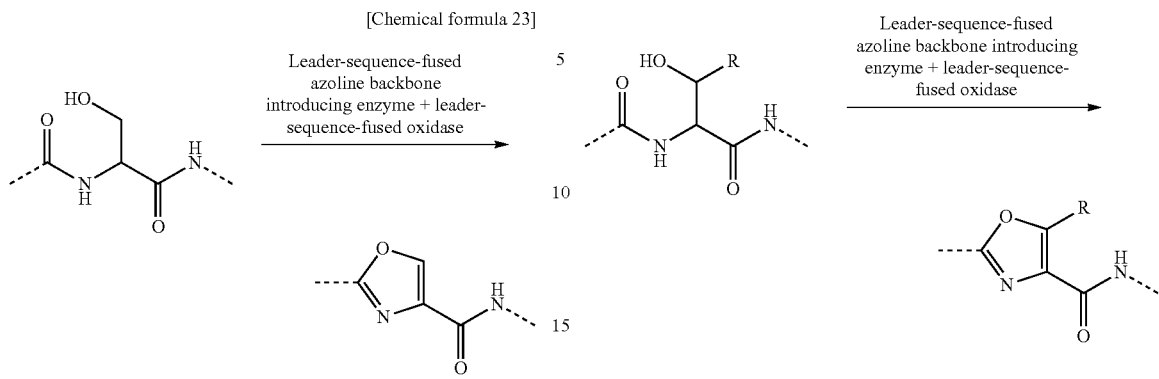

Thr:

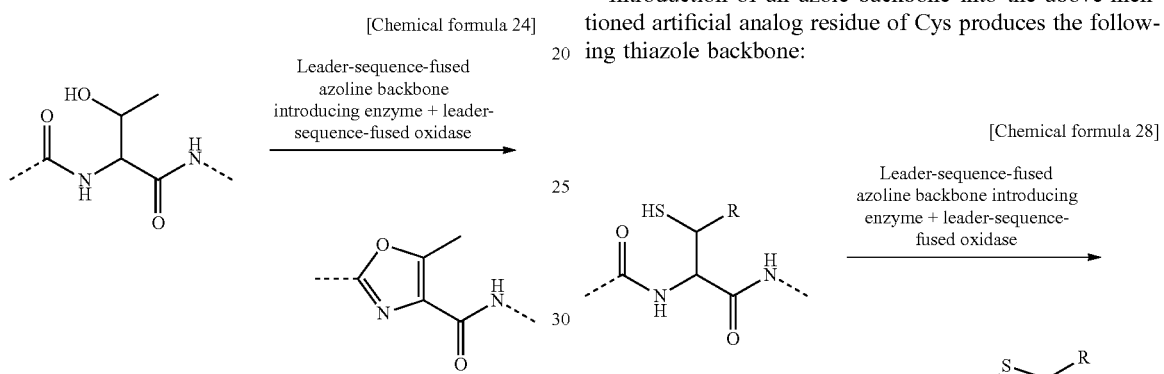

Cys:

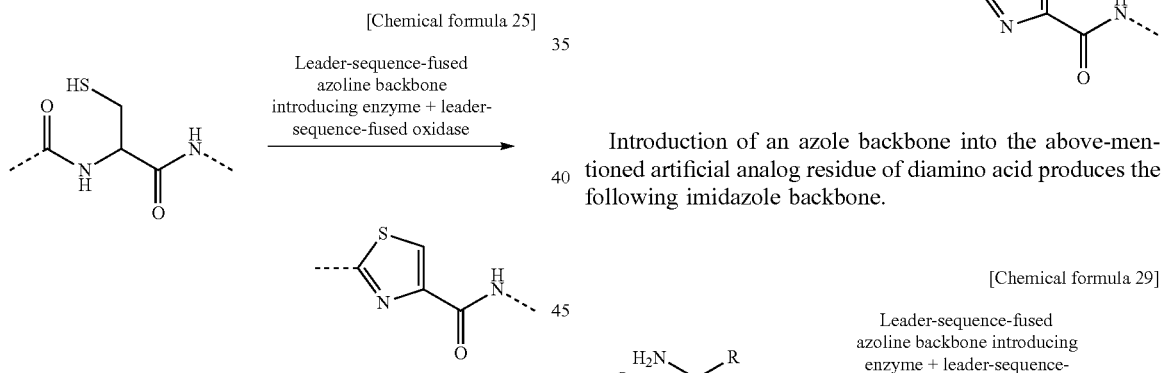

Dap:

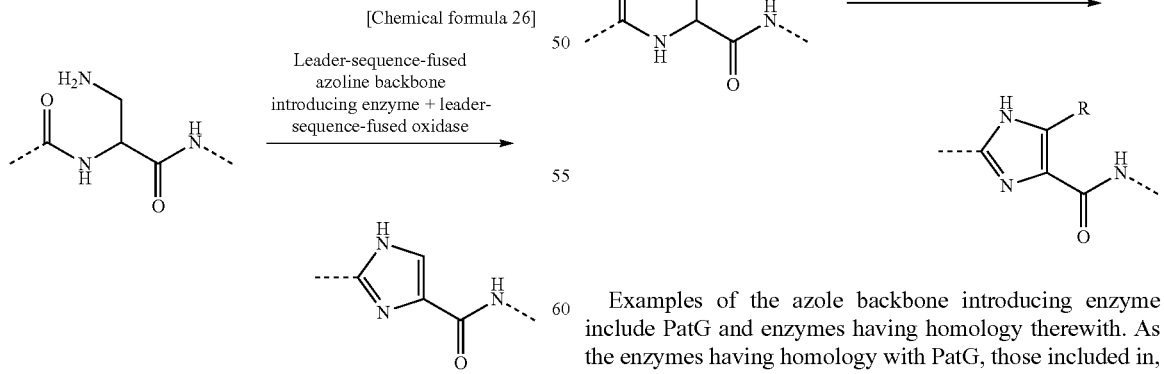

For example, introduction of an azole backbone to the above-mentioned artificial analog residue of Thr produces the following oxazole backbone.

Introduction of an azole backbone into the above-mentioned artificial analog residue of Cys produces the following thiazole backbone:

Introduction of an azole backbone into the above-mentioned artificial analog residue of diamino acid produces the following imidazole backbone.

Examples of the azole backbone introducing enzyme include PatG and enzymes having homology therewith. As the enzymes having homology with PatG, those included in, for example, Lee, et al. (Lee, S. W. et al., PNAS vol. 105, No. 15, 5879-5884, 2008) can be used, but such enzymes are not limited thereto.

As the azole backbone introducing enzyme, that obtained by binding thereto a leader sequence of the substrate thereof or a partial sequence thereof may be used. Alternatively, a reaction may be carried out by adding the leader sequence of the substrate or partial sequence thereof as an independent peptide in a reaction container. The leader sequence of the substrate of the azole backbone introducing enzyme or a partial sequence thereof may be the same as the leader sequence of the substrate of the azoline backbone introducing enzyme or partial sequence thereof.

As the azole backbone introducing enzyme, a mutant obtained by deleting a peptidase domain from PatG or a mutant which has lost its peptidase activity by point mutation may be used. PatG is composed of two domains and in natural one, an N-terminal oxidase domain converts the azoline backbone constructed by PatD into an azole backbone and the C-terminal peptidase domain is involved in cleavage and macrocyclization of the peptide after modification. In the present invention, therefore, a peptidase domain-deficient mutant or a mutant that has lost its peptidase activity as a result of point mutation may be used.

(Construction Method of Heterocycle-Containing Compound Library [1])

The present invention embraces a construction method of a library including two or more compounds containing a heterocycle introduced by an azoline backbone introducing enzyme (which library will hereinafter be called "azoline-based compound library").

The construction method of such a library includes, in the above-mentioned production method of a compound containing a heterocycle introduced by an azoline backbone introducing enzyme, preparing a peptide library including two or more peptides different in $(Xaa_3)n$ and modifying the resulting peptide library with an azoline backbone introducing enzyme.

The step of preparing a peptide library can be achieved by preparing an mRNA library encoding the peptide library and then translating it in a reconstituted translation system.

This mRNA library includes mRNAs encoding a number of peptides different in $(Xaa_3)n$ and can be prepared, for example, by synthesizing a DNA containing a sequence such as (NNN)n, (NNK)n, (NNT)n, or (NNG)n as that encoding $(Xaa_3)n$ and transcribing it. Here, N stands for any one of A, C, G, and T; K stands for any one of G and T; NNN and NNK each encode any one of 20 proteinogenic amino acids; and NNU and NNG encode any one of 15 and 13 proteinogenic amino acids, respectively.

When $(Xaa_3)n$ is $(Xaa_5-Xaa_6)p$, a portion of an mRNA library encoding $(Xaa_5-Xaa_6)p$ can be prepared, for example, by synthesizing a DNA containing a sequence such as (NNK-WST)n or (NNK-TGT)n and transcribing it. Here, N stands for any one of A, C, G, and T; K stands for either one of G and T; W stands for either one of A and T; S stands for either one of C and G; NNN and NNK each encode any one of 20 proteinogenic amino acids; WST encodes any one of Ser, Thr, and Cys; and TGT encodes Cys.

The library having such a constitution has a sufficient size because, for example, supposing that only 20 natural amino acids are used in the case of $(Xaa_3)n$ in which n stands for 10, $20^{10}$ kinds of peptides can be prepared theoretically and in the case where $(Xaa_5-Xaa_6)n$ is (NNK-WSU)n and n stands for 5, $20^5 \times 3^5$ kinds of variants can be prepared.

A nucleic acid library encoding the library of the peptides represented by the formula (I) can be obtained by synthesizing a nucleic acid having, at the 5' end of a nucleic acid encoding $(Xaa_3)m$, a nucleic acid encoding $(Xaa_2)m$ containing a start codon and having at the 3' end, a nucleic acid encoding $(Xaa_4)o$ and then translating the resulting nucleic acid.

The following is one embodiment of the nucleic acid encoding the peptide represented by the formula (I):

ATG-GGN-(NNK)x-NYK-TGC-NYK-(NNK)x-NYK-TGC-NYK-(NNK)x wherein, N represents A, C, G, or T, K represents G or T, Y represents C or T, W represents A or T, and S stands for C or G.

In this nucleic acid, $(Xaa_2)m$ is encoded by ATG-GGN, $(Xaa_3)n$ is encoded by (NNK)x-NYK-TGC-NYK-(NNK)x-NYK-TGC-NYK, and $(Xaa_4)o$ is encoded by (NNK)x.

According to such a constitution, the Cys encoded by TGC has, on both sides thereof, a non-hydrophilic amino acid.

The following is another embodiment of the nucleic acid encoding the peptide represented by the formula (I):

ATG-(NNK)m-[(NYK)-(WST)]n-(NNK)o wherein, N represents A, C, G, or T, K represents G or T, Y represents C or T, W represents A or T, and S represents C or G.

Using such a nucleic acid in which WST represents any of Ser, Thr, and Cys and NYK represents a non-hydrophilic amino acid can provide a peptide likely to be modified by the azoline backbone introducing enzyme, because Ser, Thr, or Cys is placed at an even numbered position in $(Xaa_3)n$ and therefore, a hydrophilic amino acid can be prevented from adjoining to the N-terminal side of Cys.

Using NYK-(NNK)x instead of (NNK)o as a nucleic acid encoding $(Xaa_4)o$, a hydrophilic amino acid can also be prevented from adjoining to the C-terminal side of Cys.

In the above example, a sequence downstream of the cassette can be fixed to Ala-Tyr-Asp by using, as the nucleic acid encoding $(Xaa_4)o$, GCG-TAC-GAT-(NNK)x instead of (NNK)o. As a result, a peptide likely to be modified by the azoline backbone introducing enzyme can be obtained.

In one embodiment of the construction method of an azoline-based compound library according to the present invention, a library that includes two or more complexes between the peptide represented by the formula (I) that has been modified by the azoline backbone introducing enzyme and an mRNA encoding the peptide is constructed. This makes it possible to apply the azoline-based compound library to mRNA display (Nemoto, N. et al., FEBS Lett. 1997, 405-408; Roberts, R. W. and Szostak, J. W. Proc. Natl. Acad. Sci. USA 1997, 94, 12297-12302).

When a peptide that binds to a target substance is screened using such a peptide-mRNA complex library and a reverse transcription reaction of the selected peptide-mRNA complex is performed, a cDNA-containing complex can be obtained so that the base sequence of it can be determined by the conventional method.

The peptide-mRNA complex can be prepared, for example, by binding puromycin to the 3' end of each of mRNAs of the mRNA library in a known manner to prepare a puromycin-bound mRNA library and expressing the resulting puromycin-bound mRNA library in a cell-free translation system.

After preparation of the peptide-mRNA complex library in such a manner, it is reacted with the azoline backbone introducing enzyme to obtain an azoline-based compound library.

(Construction Method of Heterocycle Compound Library [2])

The present invention embraces a method of constructing a library including two or more compounds having a heterocycle introduced by the azole backbone introducing enzyme (which library will hereinafter be called "azole-based compound library". The azoline-based compound library and the azole-based compound library will hereinafter be called "heterocycle compound library", collectively).

The method includes reacting a heterocycle-introduced peptide library, which has been obtained by the method of constructing a compound library containing a heterocycle introduced using an azole backbone introducing enzyme, with the azole backbone introducing enzyme and converting at least one of the heterocycles introduced by the azoline backbone introducing enzyme into a heterocycle introduced by the azole backbone introducing enzyme.

In one embodiment, the method of constructing an azole-based compound library according to the present invention includes, after introduction of an azoline backbone by the above-mentioned method of constructing an azoline-based compound library, reacting the azoline backbone-introduced library with the azole backbone introducing enzyme to convert at least one of the azoline backbones into an azole backbone.

The reaction for introducing the azole backbone can be carried out by adding the azole backbone introducing enzyme to the container in which the reaction by the azoline backbone introducing enzyme has been performed.

(Heterocycle Compound Library [1])

The present invention embraces a novel azoline compound-based library containing two or more peptides into which a heterocycle has been introduced by using the azoline backbone introducing enzyme.

It has been revealed that when the azoline backbone introducing enzyme is activated by binding a leader sequence thereto, recognition sequences sandwiching therebetween $(Xaa_3)r$ corresponding to a library portion (cassette region) may be shorter than has been thought conventionally and a shorter sequence contributes to efficient introduction of an azoline backbone.

The azoline-based compound library according to the present invention, therefore, includes two or more compounds each obtained by introducing, by using an azoline backbone introducing enzyme, a heterocycle into at least one of Cys, Ser, Thr, 2,3-diamino acids, homocysteine, homoserine, and 2,4-diamino acids, and analogs thereof of $(Xaa_3)n$ of a peptide represented by the following formula (II):

$Xaa_1$-$(Xaa_2)q$-$(Xaa_3)r$-$(Xaa_4)s$ (II)

[wherein, $Xaa_1$ represents an arbitrary amino acid encoded by a start codon;

$(Xaa_2)q$ represents q numbers of arbitrary amino acids and q represents an integer selected from 0 to 3;

$(Xaa_3)r$ represents r numbers of arbitrary amino acids and at least one of them is an amino acid selected from the group consisting of Cys, Ser, Thr, 2,3-diamino acids, homocysteine, homoserine, and 2,4-diamino acids, and analogs thereof and r represents an integer selected from 2 to 40; and $(Xaa_4)s$ represents s numbers of arbitrary amino acids and o represents an integer selected from 1 to 3].

$(Xaa_2)q$ is not particularly limited and it may be, for example, composed of a single Gly residue. $(Xaa_4)s$ is not also particularly limited and it may be, for example, Ala-Tyr-Asp.

In the azoline-based compound library, each of the peptides modified with the azoline backbone introducing enzyme preferably forms a complex with an mRNA encoding the peptide portion thereof. The library having such a constitution can be applied to mRNA display.

(Heterocycle Compound Library [2])

The present invention embraces a novel azole compound-based library including two or more peptides in which a heterocycle has been introduced by using the azole backbone introducing enzyme.

The azole-based compound library of the present invention includes two or more compounds obtained by introducing a heterocycle by an azole backbone introducing enzyme into at least one of Cys, Ser, Thr, 2,3-diamino acids, homocysteine, homoserine, and 2,4-diamino acids, and analogs thereof of $(Xaa_3)n$ of a peptide represented by the following formula (II):

$Xaa_1$-$(Xaa_2)q$-$(Xaa_3)r$-$(Xaa_4)s$ (II).

In the azole-based compound library, each of the peptides modified with the azole backbone introducing enzyme preferably forms a complex with an mRNA encoding the peptide portion thereof. The library having such a constitution can be applied to mRNA display.

(Screening Method)

The present invention embraces a screening method for identifying a compound that binds to a target substance.

In one embodiment, the screening method of the present invention includes bringing a heterocycle compound library constructed by the method of the present invention into contact with a target substance and then incubating the resulting compound.

The target substance is not particularly limited herein and may be, for example, a low molecular compound, a high molecular compound, a nucleic acid, a peptide, a protein, sugar, or a lipid. In particular, according to the library of the present invention, the screening method can also be used when a target substance has a protease activity.

The target substance can be brought into contact with the library of the present invention, for example, while immobilizing it onto a solid phase support. The "solid phase support" as used herein is not particularly limited insofar as it is a support onto which a target substance can be immobilized. Examples include microtiter plates, substrates, and beads made of glass, a metal, a resin, or the like, nitrocellulose membranes, nylon membranes, and PVDF membranes. The target substance can be immobilized onto such a solid phase support in a known manner.

The target substance and the library are brought into contact with each other in a buffer selected as needed and they are interacted with while controlling pH, temperature, time, and the like.

In one embodiment, the screening method of the present invention further includes selecting a compound containing a heterocycle that has bound to the target substance. With regard to binding to the target substance, the peptide is labeled in advance by a known method capable of detectably labeling the peptide and after the step of bringing the library into contact with the target substance, washing the surface of the solid phase support with a buffer, and then detecting the compound that has bound to the target substance.

Examples of the detectable label include enzymes such as peroxidase and alkaline phosphatase, radioactive substances such as $^{125}I$, $^{131}I$, $^{35}S$, and $^{3}H$, fluorescent substances such as fluorescein isothiocyanate, rhodamine, dansyl chloride, phycoerythrin, tetramethyl rhodamine isothiocyanate, and near infrared fluorescent materials, light-emitting substances such as luciferase, luciferin, and aequorin, and nanoparticles such as gold colloid and quantum dot. When an enzyme is used as the label, the compound can be detected by adding a substrate of the enzyme to develop a color. The compound can also be detected by binding biotin to the peptide and then binding avidin or streptavidin labeled with an enzyme or the like to the biotin-bound peptide.

The screening method can not only detect or analyze the presence/absence or degree of binding but also analyze the enhanced or inhibited activity of the target substance and thereby identify a heterocycle compound having such enhanced or inhibited activity. Such a method also permits identification of a heterocycle compound having physiological activity and useful as a drug.

When the heterocycle compound library is composed of peptide-mRNA complexes, screening can be carried out using an mRNA display method.

In this case, after reverse transcription reaction of a heterocycle compound—mRNA complex library, the library is brought into contact with a target substance immobilized onto a solid phase support. A complex that binds to the target substance is selected and its DNA is amplified by PCR. By using this DNA, a heterocycle compound-mRNA complex library is constructed again. Similar operations are repeated.

Since a heterocycle compound-mRNA complex having high affinity with the target substance is concentrated, a heterocycle compound that binds to the target substance can be identified efficiently by analyzing the sequence of the mRNA of the concentrated complex.

(Screening Kit)

The present invention provides a kit for screening of a heterocycle compound.

In one embodiment, the screening kit of the present invention includes the heterocycle compound library constructed by the method of the present invention or the heterocycle compound library of the present invention.

The screening kit of the present invention includes, in addition, a reagent and an apparatus necessary for detecting the binding between a target substance and a heterocycle compound. Examples of such a reagent and apparatus include, but not limited to, solid phase supports, buffers, labeling reagents, enzymes, enzyme reaction terminator solutions, and microplate readers.

The disclosure of all the patent documents and non-patent documents cited herein are incorporated herein by reference in its entirety.

EXAMPLES

The present invention will hereinafter be described specifically based on Examples, but the present invention is not limited to or by them. The present invention can be changed into various embodiments by those skilled in the art without departing from the significance of the present invention. Such changes are also embraced in the scope of the present invention.

[1] Expression and Purification of Leader Sequence-Bound PatD (LS-Fusion PatD)

An LS-fusion PatD having a leader sequence bound to the N-terminal side or C-terminal side thereof was expressed and purified.

For expression on the N-terminal side, a PatD gene was introduced into a pET16b plasmid to prepare a construct plasmid having, at the N terminal thereof, a 10×His tag added. The N terminal region of the PatD gene was cleaved using NdeI or NdeI and NheI and a DNA encoding a leader sequence and a GS linker region different in length was introduced to prepare an LS-fusion PatD plasmid in which the leader sequence and GS linker had bound to the N terminal of PatD.

For expression on the C-terminal side, first, a C-terminal stop codon of a PatD gene was eliminated. Then, the gene was cleaved using XhoI and BamHI and a DNA encoding a GS linker region different in length, a leader sequence, and a stop codon was introduced to construct an LS-fusion PatD plasmid having a GS linker and the leader sequence bound to the C terminal of PatD.

Next, these plasmids were transformed into an *Escherichia coli* BL21 (DE3) pLysS strain, followed by culturing at 30° C. When O.D. reached 0.4, 0.1 mM of IPTG was added to induce mass expression, followed by culturing overnight at 15° C. The cells collected were suspended in a lysis buffer (1 M NaCl, 25 mM Imidazole, 50 mM HEPES-Na (pH7.7)) and then lysed ultrasonically. The sample was filtered and purified using a His-Trap HP column. The column was equilibrated in advance with 17 CV of Buffer A (500 mM NaCl, 25 mM imidazole, 50 mM HEPES-Na (pH7.7)) and after injection of the sample therein, the protein in the sample was separated by gradually increasing the concentration of Buffer B (500 mM NaCl, 1 M imidazole, 50 mM HEPES-Na (pH7.7)) to obtain a pure LS-fusion PatD fraction.

The sample thus obtained was concentrated to about 4 times with Amicon Ultra (Millipore) 30 kDa. Then, buffer was exchanged with Store Buffer (200 mM NaCl, 25 mM HEPES (pH7.7), 10% glycerol) by using PD-10 (GE lifescience). After concentration to about 4 times with Amicon Ultra (Millipore) 30 kDa, the resulting sample was stored at −80° C.

[2] Preparation of DNA Encoding a Substrate Peptide

In a manner similar to that employed in Patent Document 1, DNAs encoding substrate peptides having the following amino acid sequences were prepared.

TABLE 3A

| PatE mutants | (Xaa1) | uRS (Xaa2)m | CS (Xaa3)n | dRS (Xaa4)o | SEQ ID NO: |
|---|---|---|---|---|---|
| st34 | M | G | VTACITFC | GGG | 16 |
| st35 | M | G | VCACICFC | GGG | 17 |
| st36 | M | G | VTATITFT | GGG | 18 |
| st37 | M | G | VSASISFS | GGG | 19 |
| st1 | M | GLEAS | VCACICFC | AYDGVEPS | 20 |
| st2 | M | GLEAS | VCACICFC | AYDGV | 21 |
| st3 | M | GLEAS | VCACICFC | AYD | 22 |

TABLE 3A-continued

| PatE mutants | (Xaa1) | uRS (Xaa2)m | CS (Xaa3)n | dRS (Xaa4)o | SEQ ID NO: |
|---|---|---|---|---|---|
| st4 | M | GLEAS | VCACICFC | A | 23 |
| st5 | M | GLEAS | VCACICFC |  | 24 |
| st6 | M | EAS | VCACICFC | AYDGVEPS | 25 |
| st7 | M | S | VCACICFC | AYDGVEPS | 26 |
| st8 | M |  | VCACICFC | AYDGVEPS | 27 |
| st13 | M | GGGGG | VCACICFC | GGGGGGGG | 28 |
| st16 | M | GGGGG | VCACICFC | GGGGG | 29 |
| st17 | M | GGGGG | VCACICFC | GGG | 30 |
| st18 | M | GGGGG | VCACICFC | G | 31 |
| st19 | M | GGGGG | VCACICFC |  | 32 |
| st14 | M | GGG | VCACICFC | GGGGGGGG | 33 |
| st15 | M |  | VCACICFC | GGGGGGGG | 34 |
| st136 | M | G | VCACICFC | A | 35 |
| st58 | M | G | VCACICFC | AYD | 36 |
| st137 | M | G | VCACICFC | AYDGV | 37 |
| st138 | M | G | VCACICFC | AYDGVEPS | 38 |
| st97 | M | G | VCACECFC | AYD | 39 |
| st98 | M | G | VCACECFC | AYDGV | 40 |
| st99 | M | G | VCACECFC | AYDGVEPS | 41 |
| st100 | M | GGG | VCACECFC | AYD | 42 |
| st103 | M | EAA | VCACECFC | AYD | 43 |
| st97 | M | G | VCACECFC | AYD | 44 |
| st98 | M | G | VCACECFC | AYDGV | 45 |
| st99 | M | G | VCACECFC | AYDGVEPS | 46 |
| st100 | M | GGG | VCACECFC | AYD | 47 |
| st101 | M | GGG | VCACECFC | AYDGV | 48 |
| st102 | M | GGG | VCACECFC | AYDGVEPS | 49 |
| st103 | M | EAA | VCACECFC | AYD | 50 |
| st104 | M | EAA | VCACECFC | AYDGV | 51 |
| st105 | M | EAA | VCACECFC | AYDGVEPS | 52 |

TABLE 3B

| PatE mutants |  | uRS | CS | dRS | SEQ ID NO: |
|---|---|---|---|---|---|
| st57 | M | G | VTACITFC | AYD | 53 |
| st34 | M | G | VTACITFC | GGG | 54 |
| st58 | M | G | VCACICFC | AYD | 55 |
| st35 | M | G | VCACICFC | GGG | 56 |
| st59 | M | G | VTATITFT | AYD | 57 |

TABLE 3B-continued

| PatE mutants | uRS | CS | dRS | SEQ ID NO: |
|---|---|---|---|---|
| st36 | M | G | VTATITFT | GGG | 58 |
| st60 | M | G | VTAC | AYD | 59 |
| st38 | M | G | VTAC | GGG | 60 |
| st61 | M | G | VTACRTFC | AYD | 61 |
| st54 | M | G | VTACRTFC | GGG | 62 |
| st42 | M | G | VCAC | GGG | 63 |
| st35 | M | G | VCACICFC | GGG | 64 |
| st43 | M | G | VCACICFCVCAC | GGG | 65 |
| st44 | M | G | VCACICFCVCACVCIC | GGG | 66 |
| st45 | M | G | VCACICFCVCACVCICYCFCIC | GGG | 67 |
| st139 | M | G | VCAC | AYD | 68 |
| st58 | M | G | VCACICFC | AYD | 69 |
| st140 | M | G | VCACICFCVCAC | AYD | 70 |
| st141 | M | G | VCACICFCVCACVCIC | AYD | 71 |
| st142 | M | G | VCACICFCVCACVCICYCFCIC | AYD | 72 |
| st38 | M | G | VTAC | GGG | 73 |
| st34 | M | G | VTACITFC | GGG | 74 |
| st39 | M | G | VTACITFCVTAC | GGG | 75 |
| st40 | M | G | VTACITFCVTACVTIC | GGG | 76 |
| st41 | M | G | VTACITFCVTACVTICYTFCIT | GGG | 77 |
| st158 | M | G | VTACITFCVTACVTIC | AYD | 78 |
| st46 | M | G | VTAT | GGG | 79 |
| st36 | M | G | VTATITFT | GGG | 80 |
| st47 | M | G | VTATITFTVTAT | GGG | 81 |
| st48 | M | G | VTATITFTVTATVTIT | GGG | 82 |
| st49 | M | G | VTATITFTVTATVTITYTFTIT | GGG | 83 |
| st159 | M | G | VTATITFTVTATVTIT | AYD | 84 |
| st106 | M | G | VCACNCFC | AYD | 85 |
| st107 | M | G | VCACQCFC | AYD | 86 |
| st108 | M | G | VCACKCFC | AYD | 87 |
| st110 | M | G | VCACHCFC | AYD | 88 |
| st109 | M | G | VCACRCFC | AYD | 89 |
| st111 | M | G | VCACDCFC | AYD | 90 |
| st97 | M | G | VCACECFC | AYD | 91 |
| st127 | M | G | VCACPCFC | AYD | 92 |

TABLE 3C

| PatE mutants | uRS | CS | dRS | SEQ ID NO: |
|---|---|---|---|---|
| st80 | M G | VCACNCFC | GGGGGGGG | 93 |
| st81 | M G | VCACQCFC | GGGGGGGG | 94 |
| st82 | M G | VCACXCFC | GGGGGGGG | 95 |
| st84 | M G | VCACHCFC | GGGGGGGG | 96 |
| st83 | M G | VCACRCFC | GGGGGGGG | 97 |
| st85 | M G | VCACDCFC | GGGGGGGG | 98 |
| st86 | M G | VCACECFC | GGGGGGGG | 99 |
| st68 | M G | VTACNTFC | GGGGGGGG | 100 |
| st69 | M G | VTACQTFC | GGGGGGGG | 101 |
| st70 | M G | VTACXTFC | GGGGGGGG | 102 |
| st71 | M G | VTACHTFC | GGGGGGGG | 103 |
| st72 | M G | VTACRTFC | GGGGGGGG | 104 |
| st73 | M G | VTACDTFC | GGGGGGGG | 105 |
| st74 | M G | VTACETFC | GGGGGGGG | 106 |
| st50 | M G | VTACNTFC | GGG | 107 |
| st51 | M G | VTACQTFC | GGG | 108 |
| st52 | M G | VTACKTFC | GGG | 109 |
| st53 | M G | VTACHTFC | GGG | 110 |

TABLE 3C-continued

| PatE mutants | uRS | CS | dRS | SEQ ID NO: |
|---|---|---|---|---|
| st54 | M G | VTACRTFC | GGG | 111 |
| st55 | M G | VTACDTFC | GGG | 112 |
| st56 | M G | VTACETFC | GGG | 113 |
| st112 | M G | ALICVALC | AYD | 114 |
| st113 | M G | LIVCAALC | AYD | 115 |
| st114 | M G | ALCVACILC | AYD | 116 |
| st115 | M G | DNHCKRNC | AYD | 117 |
| st116 | M G | ERKCNHEC | AYD | 118 |
| st117 | M G | YFWCFFWC | AYD | 119 |
| st118 | M G | FWWCYFYC | AYD | 120 |
| st119 | M G | ANICKANC | AYD | 121 |
| st122 | M G | ANICAKAC | AYD | 122 |
| st120 | M G | LNVCKANC | AYD | 123 |
| st121 | M G | YRWCNFEC | AYD | 124 |
| st123 | M G | YRWCFNFC | AYD | 125 |
| st124 | M G | AYLCWIFC | AYD | 126 |
| st125 | M G | AYNCIWRC | AYD | 127 |
| st126 | M G | ANYCIRWC | AYD | 128 |

TABLE 3D

| PatE mutants | uRS | CS | dRS | SEQ ID NO: |
|---|---|---|---|---|
| st87 | M G | ALICVALC | GGGGGGGG | 129 |
| st88 | M G | LIVCAALC | GGGGGGGG | 130 |
| st89 | M G | ALCVACILC | GGGGGGGG | 131 |
| st90 | M G | DNHCKRNC | GGGGGGGG | 132 |
| st91 | M G | ERKCNHEC | GGGGGGGG | 133 |
| st92 | M G | YFWCFFWC | GGGGGGGG | 134 |
| st93 | M G | FMTCYFYC | GGGGGGGG | 135 |
| st94 | M G | ANICKANC | GGGGGGGG | 136 |
| st95 | M G | LNVCKANC | GGGGGGGG | 137 |
| st96 | M G | YRWCNFEC | GGGGGGGG | 138 |
| st112 | M G | ALICVALC | AYD | 139 |
| st128 | M G | ALICVALCVLAC | AYD | 140 |
| st130 | M G | ALICVALCVLACIIVC | AYD | 141 |
| st75 | $_{AMB}$F | RVRVCDYDL | $W_{OH}$GG | 142 |
| st76 | $_{AMB}$F | RVRVCAADYDL | $W_{OH}$GG | 143 |
| st77 | $_{AMB}$F | RVRVCACAADYDL | $W_{OH}$GG | 144 |
| st78 | $_{AMB}$F | RVRVCACACAADYDL | $W_{OH}$GG | 145 |

TABLE 3D-continued

| PatE mutants | uRS | CS | dRS | SEQ ID NO: |
|---|---|---|---|---|
| st79 | $_{AMB}$F | RVRVCACACACAADYDL | W$_{OH}$GG | 146 |
| st146 | $_{AMB}$F | RVRVCAADYDL | W$_{OH}$AYD | 147 |
| st147 | $_{AMB}$F | RVRVCACAADYDL | W$_{OH}$AYD | 148 |
| st148 | $_{AMB}$F | RVRVCACACAADYDL | W$_{OH}$AYD | 149 |
| st149 | $_{AMB}$F | RVRVCACACACAADYDL | W$_{OH}$AYD | 150 |

TABLE 3E

| PatE mutants | uRS | CS | dRS | SEQ ID NO: |
|---|---|---|---|---|
| st057 | M | G | VTACITFC | AYD | 151 |
| st236 | M | G | VTACITFC | AYDGSG | 152 |
| st119 | M | G | ANICKANC | AYD | 153 |
| st237 | M | G | ANICKANC | AYDGSG | 154 |
| st122 | M | G | ANICAKAC | AYD | 155 |
| st238 | M | G | ANICAKAC | AYDGSG | 156 |
| st123 | M | G | YRWCFNFC | AYD | 157 |
| st239 | M | G | YRWCFNFC | AYDGSG | 158 |
| st173 | M | G | IAICEII | AYD | 159 |
| st240 | M | G | IAICEII | AYDGSG | 160 |
| st179 | M | G | IIRCIAI | AYD | 161 |
| st241 | M | G | IIRCIAI | AYDGSG | 162 |
| st254 | M | G | ALICVALC | AYD | 163 |
| st255 | M | G | ALICVALCV | AYD | 164 |
| st256 | M | G | ALICVALCVL | AYD | 165 |
| st259 | M | G | ALICVALC | AYDGSG | 166 |
| st260 | M | G | ALICVALCV | AYDGSG | 167 |
| st261 | M | G | ALICVALCVL | AYDGSG | 168 |
| st278 | M | G | ICFW | AYD | 169 |
| st279 | M | G | ITFW | AYD | 170 |
| st280 | M | G | ISFW | AYD | 171 |
| st281 | M | G | VFAWICFW | AYD | 172 |
| st282 | M | G | VFAWITFW | AYD | 173 |
| st283 | M | C | VFAWISFW | AYD | 174 |

TABLE 3F

| PatE mutants | uRS | CS | dRS | SEQ ID NO |
|---|---|---|---|---|
| st264 | M | G | VC | AYD | 175 |
| st150 | M | G | INICINI | AYD | 176 |
| st151 | M | G | IINCINI | AYD | 177 |
| st152 | M | G | INICNII | AYD | 178 |

TABLE 3F-continued

| PatE mutants | uRS | CS | dRS | SEQ ID NO |
|---|---|---|---|---|
| st153 | M | G | IINCNII | AYD | 179 |
| st167 | M | G | IAICNII | AYD | 180 |
| st168 | M | G | IAICRII | AYD | 181 |
| st169 | M | G | IAICKII | AYD | 182 |
| st170 | M | G | IAICRII | AYD | 183 |
| st171 | M | G | IAICHII | AYD | 184 |
| st173 | M | G | IAICEII | AYD | 185 |
| st176 | M | G | IINCIAI | AYD | 186 |
| st177 | M | G | IIQCIAI | AYD | 187 |
| st178 | M | G | IIKCIAI | AYD | 188 |
| st179 | M | G | IIRCIAI | AYD | 189 |
| st180 | M | G | IIFICIAI | AYD | 190 |
| st181 | M | G | IIDCIAI | AYD | 191 |
| st182 | M | G | IIECIAI | AYD | 192 |
| st231 | M | G | IIPCIAI | AYD | 193 |
| st232 | M | G | IITCIAI | AYD | 194 |
| st233 | M | G | IISCIAI | AYD | 195 |
| st234 | M | G | IICCIAI | AYD | 196 |
| st235 | M | G | IIMCIAI | AYD | 197 |
| st117 | M | G | YFWCFFWC | AYD | 198 |
| st129 | M | G | YFWCFFWC | YFYCAYD | 199 |

TABLE 3G

| PatE mutants | uRS | CS | dRS | SEQ ID NO: |
|---|---|---|---|---|
| st197 | $_{AMB}$F | ANICAKAC | W$_{OH}$AYD | 200 |
| st215 | $_{AMB}$F | VTACRTFC | W$_{OH}$AYDYKDDDDK | 201 |
| st217 | $_{AMB}$F | VCACNCFC | W$_{OH}$AYDYKDDDDK | 202 |
| st218 | $_{AMB}$F | VCACQCFC | W$_{OH}$AYDYKDDDDK | 203 |
| st220 | $_{AMB}$F | VCACRCFC | W$_{OH}$AYDYKDDDDK | 204 |
| st221 | $_{AMB}$F | VCACHCFC | W$_{OH}$AYDYKDDDDK | 205 |
| st222 | $_{AMB}$F | VCACDCFC | W$_{OH}$AYDYKDDDDK | 206 |
| st226 | $_{AMB}$F | ANICKANC | W$_{OH}$AYDYKDDDDK | 207 |
| st227 | $_{AMB}$F | ANICAKAC | W$_{OH}$AYDYKDDDDK | 208 |

[3] PatD Enzyme Reaction

After the DNA prepared in [2] was transcribed and translated in a cell-free protein expression system of 5.0 μl scale (37° C., one hour) in accordance with the method of Kawakami, et al. (Kawakami et al., Chemistry & Biology 15, 32-42(2008)) and the solution conditions were adjusted by adding 45 mM HEPES-K (pH 8.4), 7.5 mM DTT, and 0.5 mM ATP (each, final concentration), the LS-fusion PatD prepared in [1] was added.

The final concentration of the LS-fusion PatD was set at 6 μM and the reaction temperature and reaction time were set at 25° C. and 16 hours, respectively.

[4] Mass Measurement Using MALDI-TOF-MS

Desalting of the peptide was performed in Wash Buffer (4% MeCN, 0.5% AcOH, 95.5% H$_2$O) by using a c-18 tip (Thermo Scientific). The desalted peptide was extracted using Elute Buffer (80% MeCN, 0.5% AcOH, 19.5% H$_2$O).

The mass of the peptide thus extracted was measured by MALDI-TOF-MS while using α-cyano-4-hydroxycinnamic acid or sinapinic acid as a matrix and presence or absence of a mass change due to addition of the LS-fusion PatD was confirmed. The number of azoline rings introduced can be found from the mass change.

[5] Investigation of LS-fusion PatD

Various LS-fusion PatDs prepared in [1] were reacted with a substrate peptide M-GLEAS-VTACITFC-AY-DGVEPS having a sequence identical to that of PatE and the number of azoline rings was determined by the method described in [4].

Figure 3A:
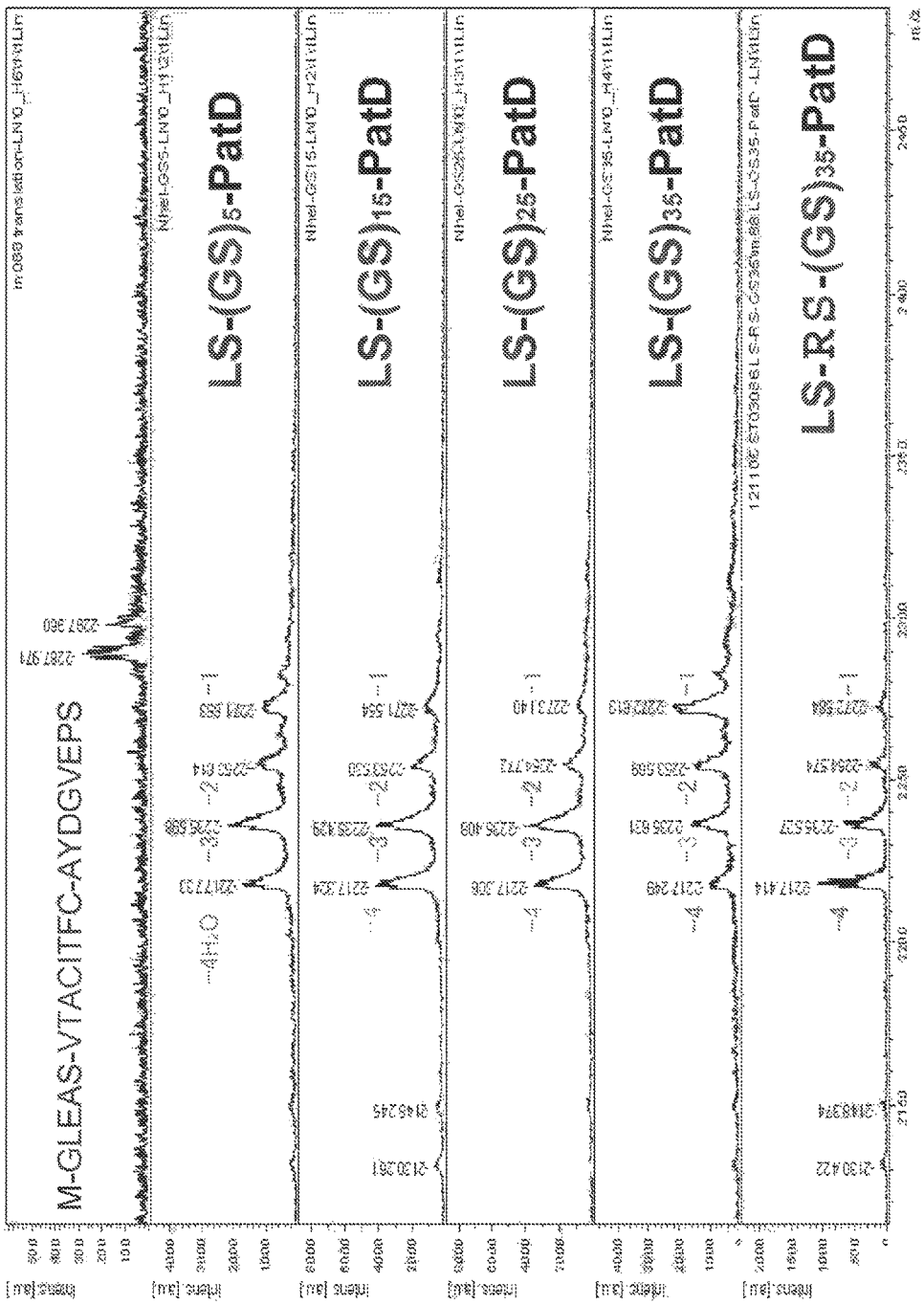
FIG. 3A shows the results of modifying a substrate peptide having a recognition sequence and a cassette sequence identical to those of PatE with the LS-fusion PatDs shown in FIGS. 2A to 2D.
Figure 3B:
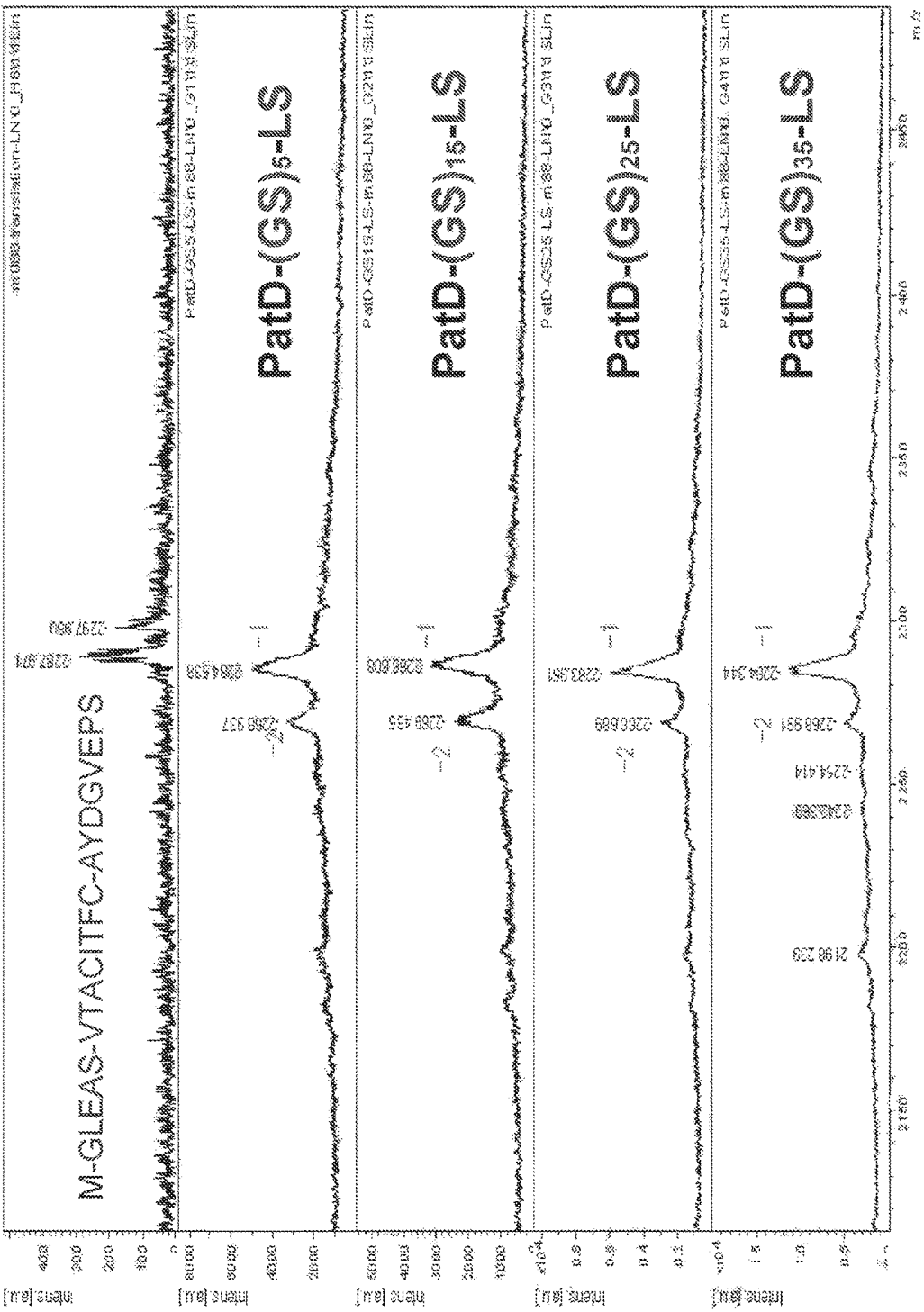
FIG. 3B shows the results of modifying a substrate peptide having a recognition sequence and a cassette sequence identical to those of PatE with the respective LS-fusion PatDs shown in FIGS. 2E and 2F.

The results are shown in FIGS. 3A and 3B. Any of the LS-fusion PatDs introduced an azoline backbone into the substrate peptide. Among them, the enzyme having a leader sequence bound to the N terminal of the PatD showed a higher introduction efficiency. In the tests conducted hereinafter, LS-(GS)$_{15}$-PatD was used.

[6] LS-fusion PatD Enzyme Reaction with Various Substrates

The LS-fusion PatD and each of various substrate peptides were reacted by the method [3] and the number of azoline rings was determined by the method [4].

[6-1] Study of Recognition Sequence (1)

Modification, with the LS-fusion PatD, of substrate peptides different in a recognition sequence (uRS, corresponding to (Xaa$_2$)m of the present invention) on the N-terminal side and a recognition sequence on the C-terminal side (dRS, corresponding to (Xaa$_4$)o of the present invention) of a cassette sequence (CS) was studied.

Figure 4A:
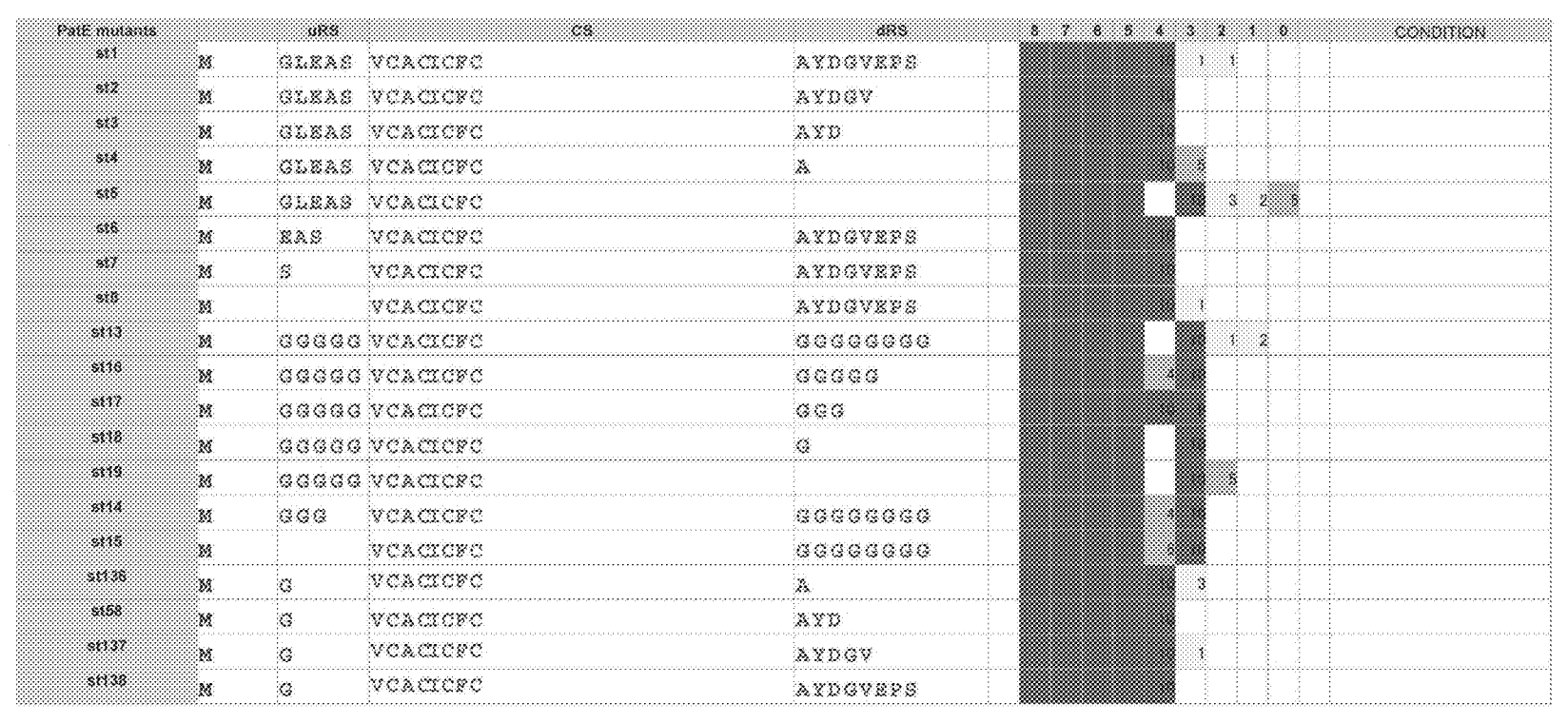

The results are shown in FIG. 4A. Reactivity did not change even when the recognition sequence on the C-terminal side was comprised of about three residues. There was no problem in reactivity even when the peptide had no recognition sequence on the N-terminal side. The reactivity showed a decreasing tendency when the recognition sequence had five or more successive Gly residues.

[6-2] Study on Recognition Sequence (2)

Difference in reactivity caused by a recognition sequence was studied using a cassette sequence whose reactivity decreased due to a hydrophilic amino acid (Glu) adjoining to the N-terminal side of Cys.

Figure 1B:
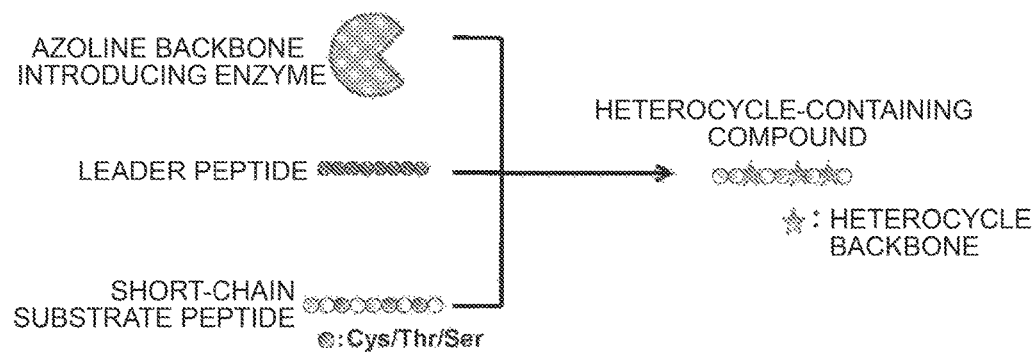
FIG. 1B shows a backbone conversion reaction of a wild type azoline backbone introducing enzyme with a leader sequence-free substrate in the presence of a leader sequence.
Figure 1C:
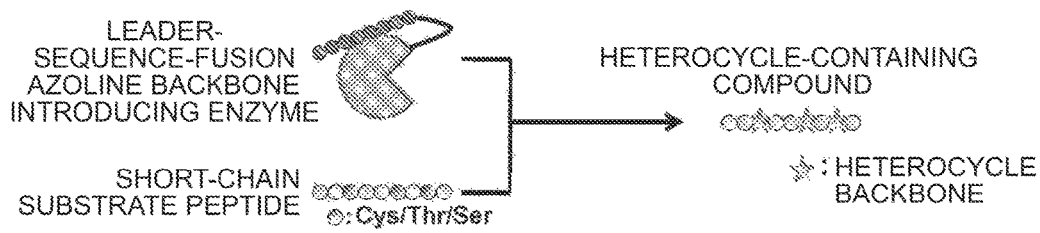
FIG. 1C shows a backbone conversion reaction of a leader-sequence-fusion azoline backbone introducing enzyme obtained by fusing a leader sequence to a wild type azoline backbone introducing enzyme with a leader sequence-free substrate.
Figure 4B-1:
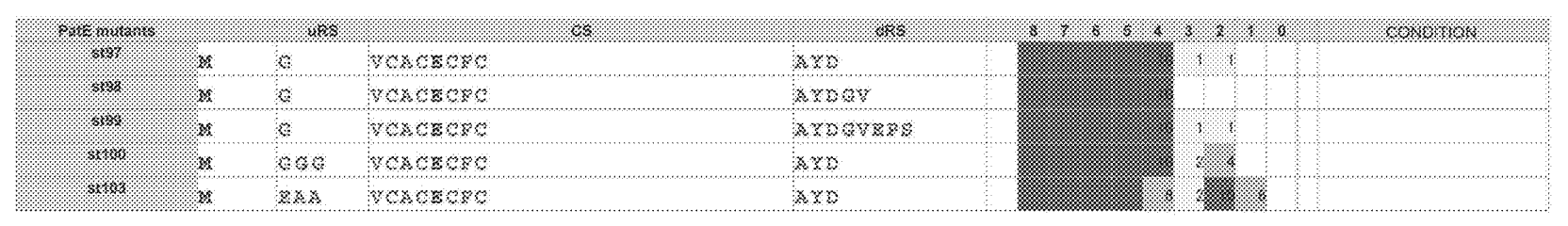
Figure 4B-3:
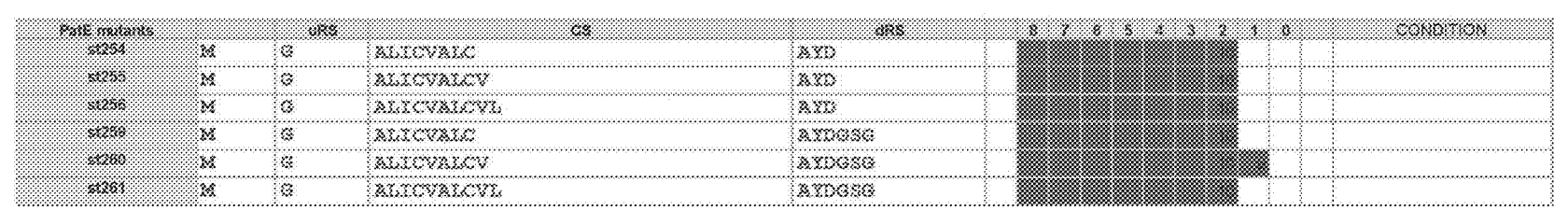

The results are shown in FIG. 4B-1. When Gly or Gly-Gly-Gly was used as uRS and Ala-Tyr-Asp, Ala-Tyr-Asp-Gly-Val, or Ala-Tyr-Asp-Gly-Val-Glu-Pro-Ser was used as dRS, the reactivity tended to be high.

[6-3] Study on Recognition Sequence (3)

Difference in reactivity of the LS-fusion Pat D with six cassette sequences was studied while using Ala-Tyr-Asp or Ala-Tyr-Asp-Gly-Ser-Gly as dRS.

Figure 4C:
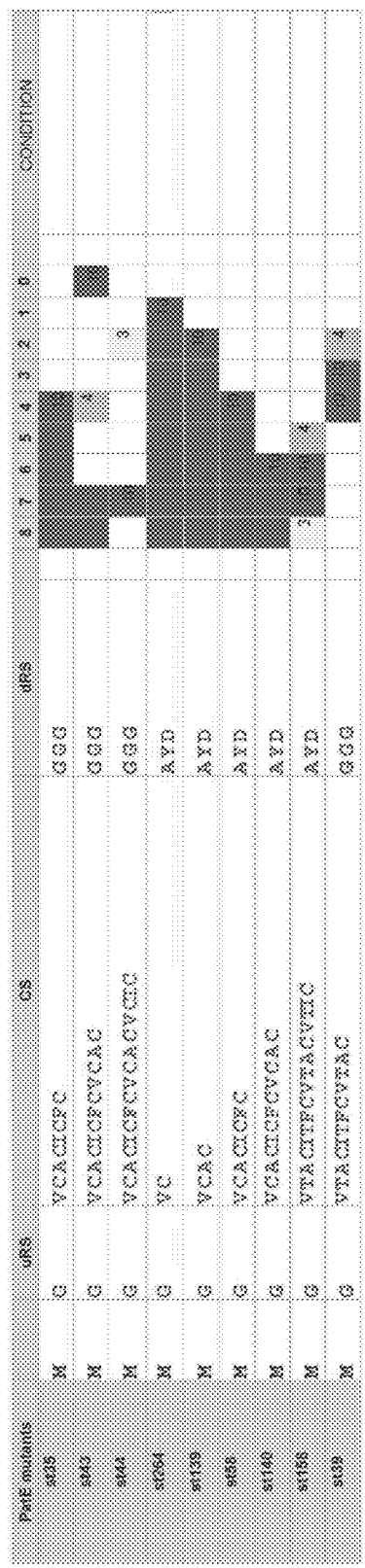
FIG. 4C shows the results of studying the modification of substrate peptides different in cassette sequence length with LS-fusion PatD.
Figures 2, 4D:
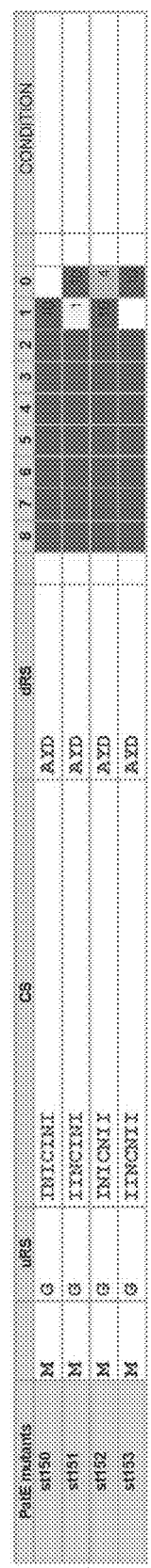

The results are shown in FIG. 4B-2. In any case, modification with the LS-fusion PatD was observed.

[6-4] Study on Recognition Sequence (4)

Difference in reactivity of the LS-fusion PatD with the cassette sequence composed of a hydrophobic amino acid was studied while using Ala-Tyr-Asp or Ala-Tyr-Asp-Gly-Ser-Gly as dRS.

The results are shown in FIG. 4B-3. In any case, modification with the LS-fusion PatD was observed.

Tests thereafter were conducted using Gly as uRS and Ala-Tyr-Asp or Gly-Gly-Gly as dRS.

[6-5] Study on Length of Cassette Sequence (1)

Modification, with the LS-fusion PatD, of substrate peptides different in length of a cassette sequence was studied.

The results are shown in FIG. 4C. It has been confirmed that change in length of a cassette sequence does not have a large influence on the reactivity.

[6-6] Study on Cassette Sequence (1)

The hydrophilic amino acid was adjoined to the N-terminal side of Cys in the cassette sequence and modification with the LS-fusion PatD was studied. It is known that a hydrophilic residue deteriorates the reactivity of wild type PatD.

The results are shown in FIG. 4D-1. It has been confirmed that even when a hydrophilic residue was adjoined, modification of Cys proceeded sufficiently. When Asp was adjacent to Cys, reactivity showed a slight decreasing tendency.

[6-6] Study on Cassette Sequence (2)

By changing the position of two Asns in a cassette sequence comprised of Ile and Asn, an influence of the hydrophilic amino acid in the cassette sequence on modification with the LS-fusion PatD was studied.

The results are shown in FIG. 4D-2. When Asn was adjacent to the N-terminal side of Cys, a modification efficiency decreased, but even when Asn was adjacent to the C-terminal side, modification occurred without a problem.

[6-7] Study on Cassette Sequence (3)

An influence on modification with the LS-fusion PatD was studied by changing an amino acid adjacent to Cys on the C-terminal side in the cassette sequence to various hydrophilic amino acids.

The results are shown in FIG. 4D-3. In any case, modification was performed efficiently.

[6-8] Study on Cassette Sequence (4)

An influence on modification with the LS-fusion PatD was studied by changing an amino acid adjacent to Cys on the N-terminal side in the cassette sequence to various hydrophilic amino acids.

The results are shown in FIG. 4D-4. Modification was performed efficiently when the amino acid was other than Asn, a basic amino acid, or an acidic amino acid.

[6-9] Study on Cassette Sequence (5)

Figure 4E:
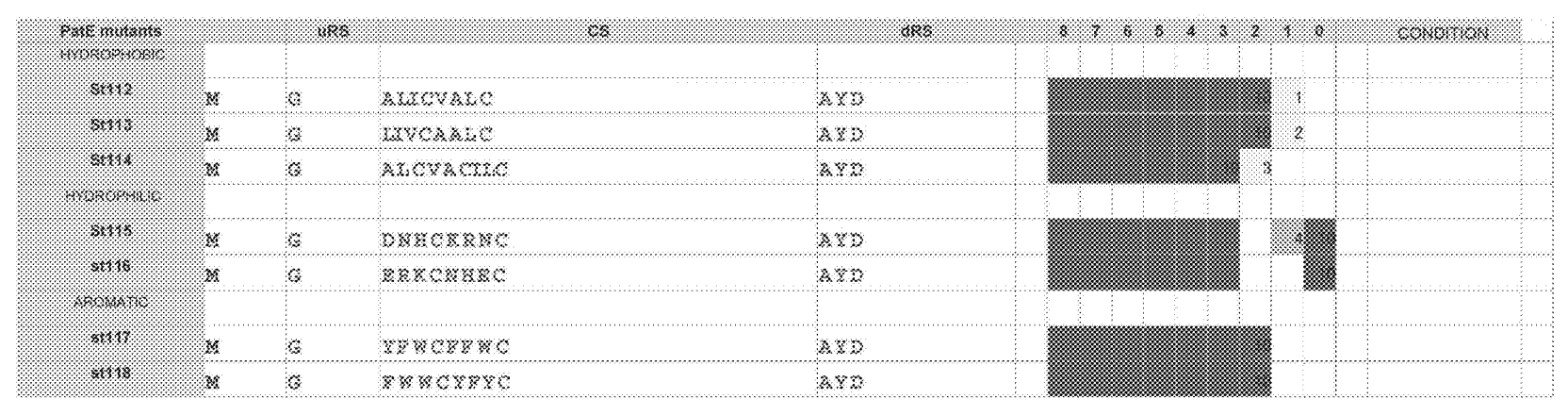

Modification with the LS-fusion PatD was studied by changing the cassette sequence variously to make it greatly different from that of PatE. More specifically, study was made on the case where the amino acids other than Cys were all hydrophobic amino acids, all hydrophilic amino acids, or all aromatic amino acids, or Cys was placed at the odd numbered position. The results are shown in FIG. 4E. When the cassette sequence contained many hydrophobic amino acids or many aromatic amino acids, an azoline ring was introduced into almost every Cys irrespective of the position of Cys. When the cassette sequence contained many hydrophilic amino acids, on the other hand, not many Cys was modified.

Figure 4F:
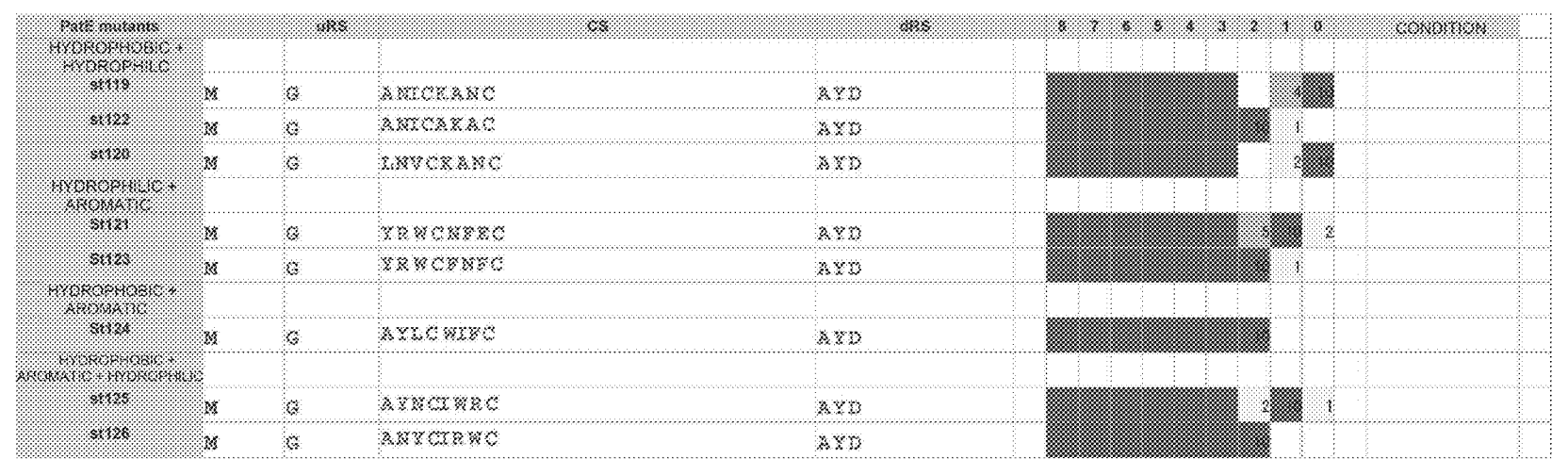

Study was made further on using, as the amino acids other than Cys, hydrophobic amino acid+hydrophilic amino acid, hydrophilic amino acid+aromatic amino acid, hydrophobic amino acid+aromatic amino acid, or hydrophobic amino acid+aromatic amino acid+hydrophilic amino acid. The results are shown in FIG. 4F. The hydrophilic amino acids were likely to deteriorate the reaction. Comparison between st125 and st126, between st119 and st122, or between st121 and st123 has revealed that reaction is not inhibited significantly when the hydrophilic amino acid, if any, is not adjacent to the Cys to be modified.

[6-10] Study on Cassette Sequence (6)

In a manner similar to that used in [6-9], modification with the LS-fusion PatD was studied by using a sequence significantly different from that of PatE and changing the length of the cassette sequence.

Figure 4G-2:
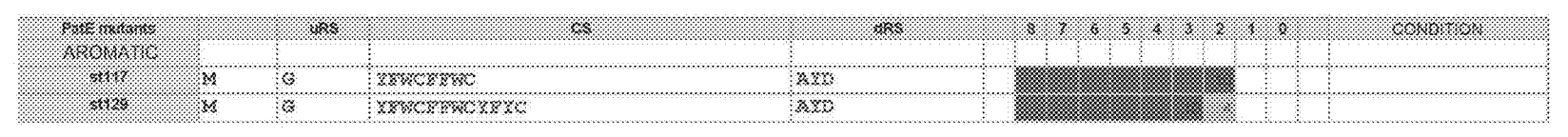

The results are shown in FIG. 4G-1. It has been confirmed that even a change in length of the cassette sequence does not have a large influence on the reactivity.

[6-11] Study on Cassette Sequence (7)

A cassette sequence composed of an aromatic amino acid was used in order to study the modification of more diversified cassette sequences with the LS-fusion PatD.

The results are shown in FIG. 4G-2. Even cassette sequences containing an aromatic amino acid were modified efficiently.

[6-12] Study on Cassette Sequence (8)

Study was made on modification, with the LS-fusion PatD, of a cassette sequence prepared in accordance with the following rule: based on the wild type cassette sequence, that is, Val-Thr-Ala-Cys-Ile-Thr-Phe-Cys or a latter half of it, that is, Ile-Thr-Phe-Cys, (i) only one residue of Cys, Thr, and Ser is modified and (ii) for substitution of Cys, Thr, or Ser by another amino acid, an aromatic amino acid (Phe or Trp) is used.

Figure 4H:
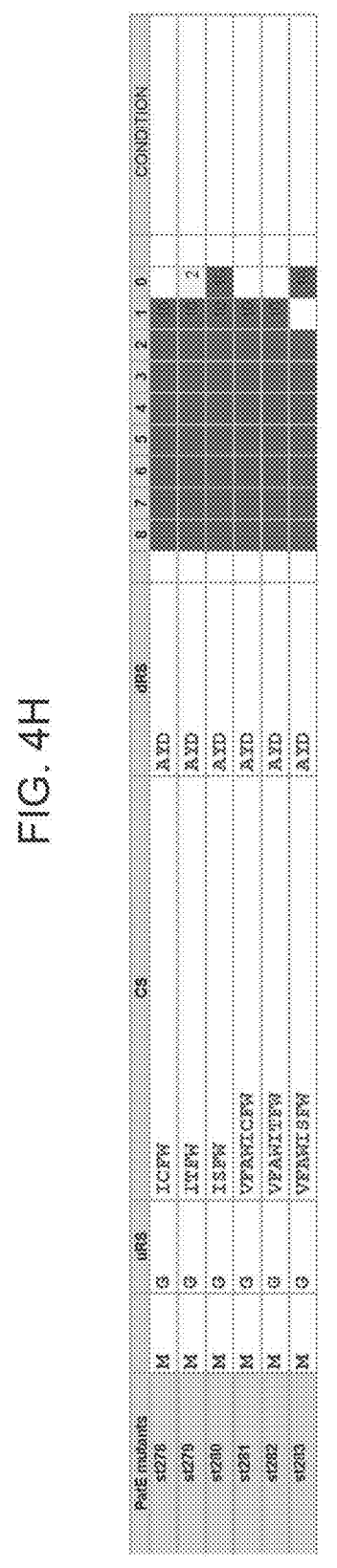

The results are shown in FIG. 4H. Any cassette sequence was modified efficiently.

[6-13] Study on Cassette Sequence (9)

Study was made on modification, with the LS-fusion PatD, of a substrate peptide having, in the cassette sequence thereof, a 2,3-diamino acid (Dap), a non-proteinogenic amino acid. The sequence of the substrate peptide was fMGI-Dap-FWAYD.

Figure 4I:
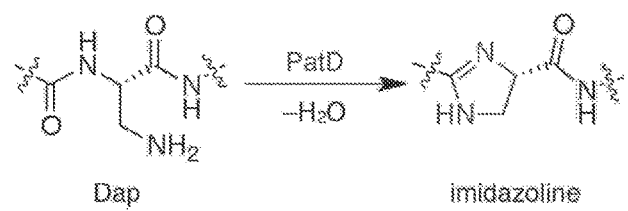
FIG. 4I shows the results of studying the modification, with LS-fusion PatD, of substrate peptides containing a non-protein amino acid in the cassette sequence thereof.
Figure 4I:
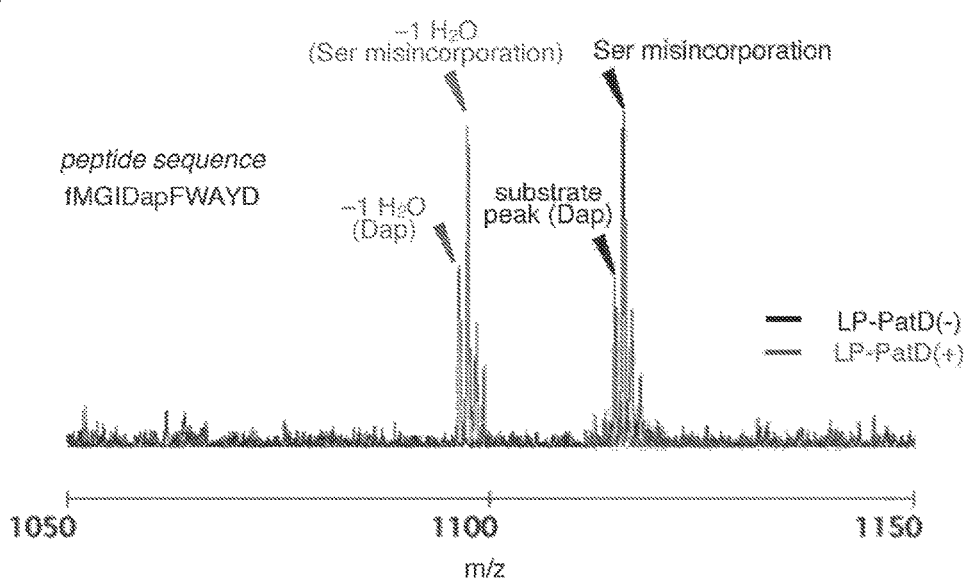

The results are shown in FIG. 4I. It has been confirmed that Dap was modified with an imidazoline ring.

[7-1] Macrocyclization of Peptide Having Azoline Backbone (1)

Figure 5A:
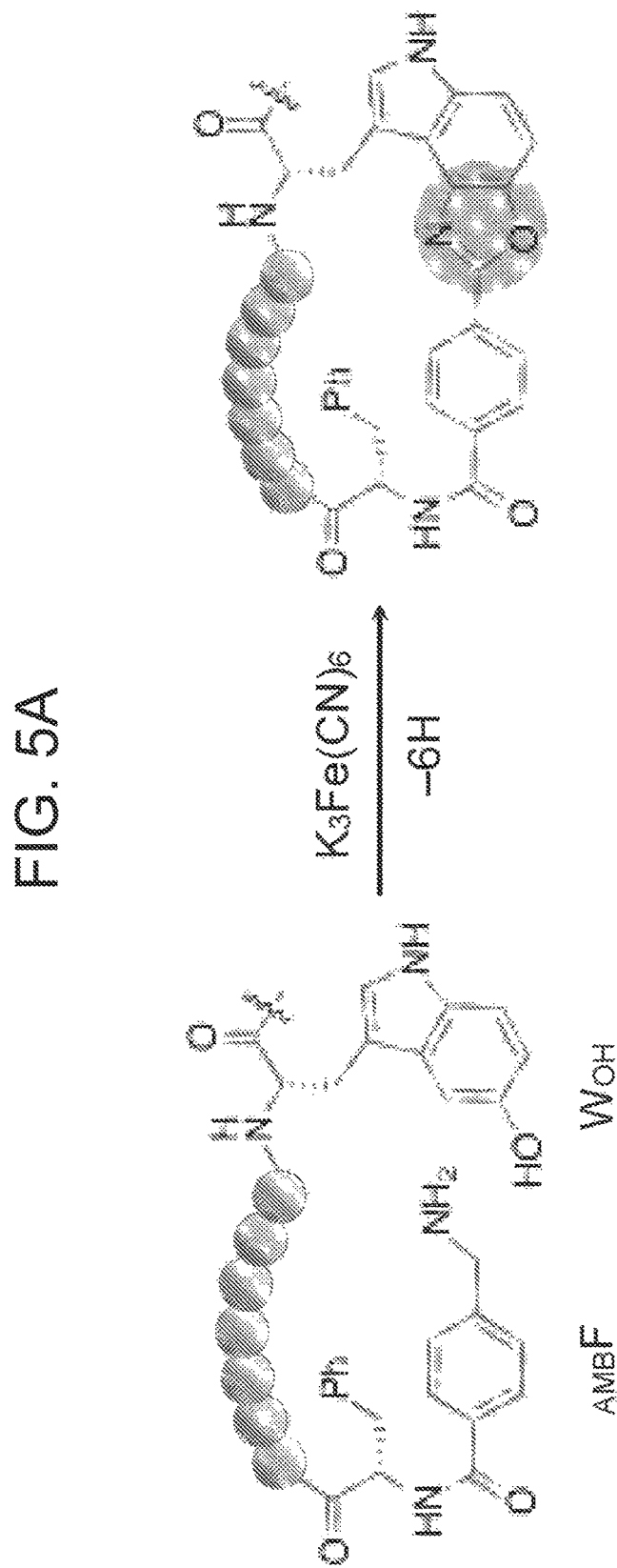
FIG. 5A shows a cyclizing reaction between $_{AMB}F$ and $W_{OH}$. 

A peptide modified with the LS-fusion PatD was macrocyclized. The peptide to be macrocyclized had $_{AMB}F$ at the N terminal thereof and had $W_{OH}$ as dRS. Macrocyclization reaction by $_{AMB}F$ and $W_{OH}$ is shown in FIG. 5A.

Also in macrocyclization, first, a DNA encoding a peptide was prepared. After transcription and translation by the method [3], it was reacted with the LS-fusion PatD. The final concentration, reaction temperature, and reaction time of the LS-fusion PatD were set at 6 μM, 25° C., and 16 hours, respectively. By a desalting column using Sephadex G-10, the solution condition was changed to 167 mM boric acid-K (pH 9.0) and 100 mM NaCl. Then, $K_3Fe(CN)_6$ was added and a reaction was performed for 30 minutes under the following conditions: 125 mM boric acid-K (pH 9.0), 75 mM NaCl, 1 mM $K_3Fe(CN)_6$ (each final concentration), and reaction temperature of 37° C. to achieve macrocyclization.

Figure 5B-2:
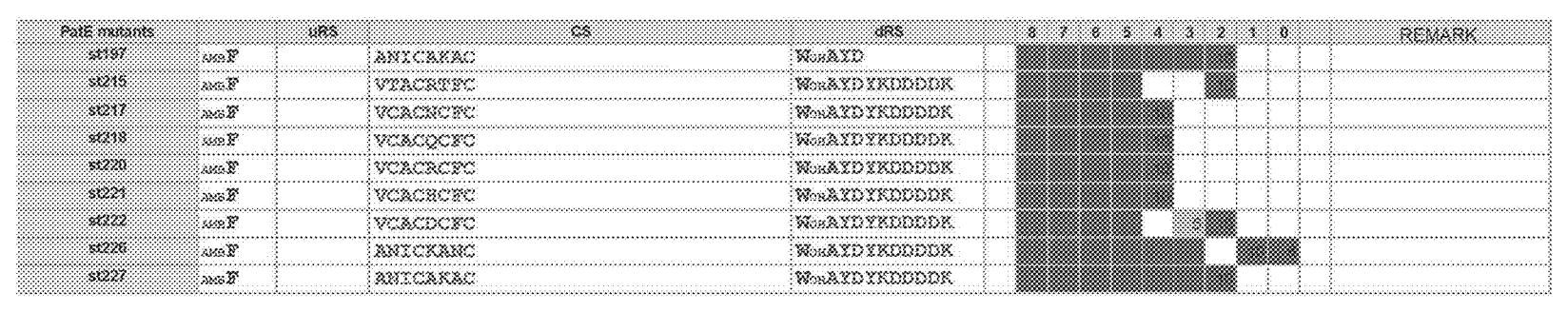
Figure 5C:
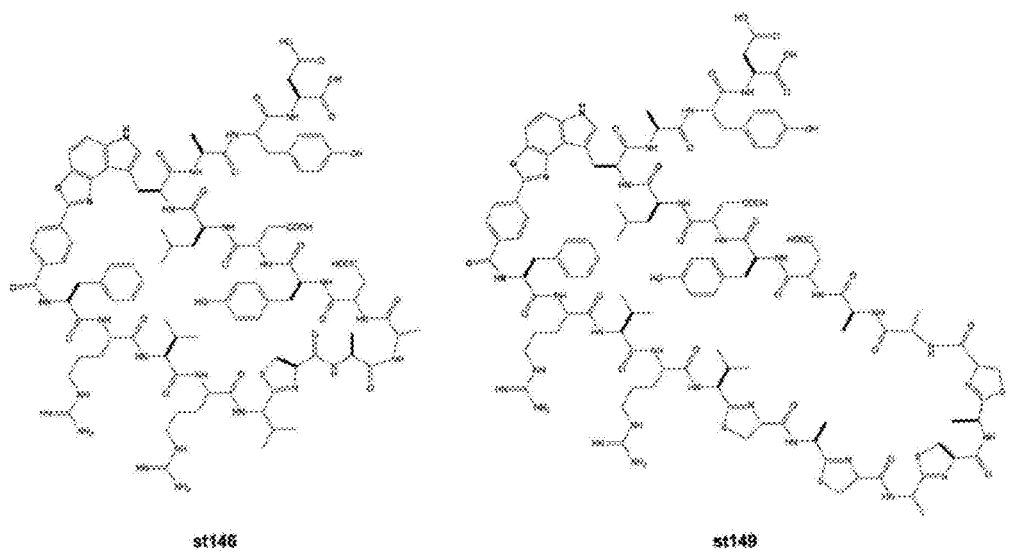
FIG. 5C shows the structure of a cyclized azoline compound.
Figure 6:
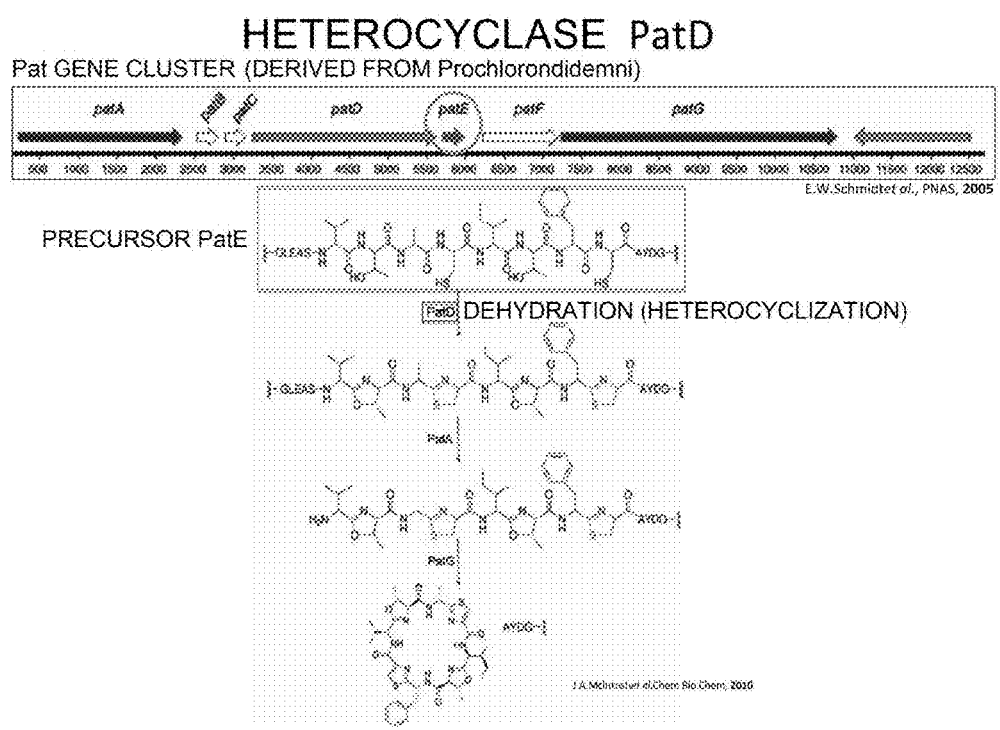
FIG. 6 schematically shows a pat gene cluster and a biosynthesis pathway thereof.

The peptide thus obtained was analyzed by the method [4]. The results are shown in FIGS. 5B-1 and 5B-2. It has been confirmed that an azoline backbone was introduced into Cys of each substrate and cyclization of the peptide was achieved. The structures of st146 and st149 are shown in FIG. 5C.

According to the method of the present invention, incorporation of a leader sequence in a substrate peptide is not required and therefore, an amino acid necessary for cyclization can be placed at the N terminal. This makes it possible to cyclize a peptide having an azoline backbone introduced therein as is.

The invention claimed is:

1. A method for producing a compound having a heterocycle introduced by an azoline backbone introducing enzyme comprising:
preparing a peptide represented by the following formula (I):

$$(Xaa_2)m\text{-}(Xaa_3)n\text{-}(Xaa_4)o \qquad (I)$$

wherein,
$(Xaa_2)m$ represents m numbers of arbitrary amino acids and m represents an integer selected from 0 to 10;
$(Xaa_3)n$ represents n numbers of arbitrary amino acids, at least one of which is an amino acid selected from the group consisting of Cys, Ser, Thr, 2,3-diamino acids, homocysteine, homoserine, and 2,4-diamino acids, and analogs thereof, and n represents an integer selected from 2 to 40; and
$(Xaa_4)o$ represents o numbers of arbitrary amino acids and o represents an integer selected from 0 to 10, and
reacting the peptide with an azoline backbone introducing enzyme to which a leader sequence of a substrate or a partial sequence thereof has been bound to introduce a heterocycle into at least one of Cys, Ser, Thr, 2,3-diamino acids, homocysteine, homoserine, and 2,4-diamino acids, and analogs thereof of $(Xaa_3)n$,
wherein the leader sequence of a substrate or the partial sequence thereof has been bound to the N terminal of the azoline backbone introducing enzyme.

2. The method according to claim 1, wherein the leader sequence or the partial sequence thereof has the following sequence:
MNKKNILPQQGQPVIRLTAGQLSSQLAELSEEAL-GDA (SEQ ID NO: 1)
MKEQNSFNLLQEVTESELDLILGA(SEQ ID NO: 2)
MILASLSTFQQMWISKQEYDEAGDA(SEQ ID NO: 3)
MELQLRPSGLEKKQAPISELNIAQTQGGDSQVLA-LNA (SEQ ID NO: 4); or a partial sequence thereof.

3. The method according to claim 1, wherein the leader sequence has been bound to the azoline backbone introducing enzyme via a spacer.

4. The method according to claim 1, wherein the $(Xaa_3)n$ is $(Xaa_5Xaa6)p$
wherein, p numbers of $Xaa_5$ each independently represent an arbitrary amino acid, p numbers of $Xaa_6$ each independently represent an amino acid selected from the group consisting of Cys, Ser, Thr, 2,3-diamino acids, homocysteine, homoserine, and 2,4-diamino acids, and analogs thereof, and p is selected from 1 to 20.

5. The method according to claim 4, wherein the $Xaa_6$ is Cys.

6. The method according to claim 1, wherein the $(Xaa_4)o$ contains, at the N terminal thereof, Ala-Tyr-Asp.

7. The method according to claim 1, wherein the step of preparing a peptide represented by the formula (I) comprises:
preparing a nucleic acid encoding the peptide represented by the formula (I), and
translating the nucleic acid in a cell-free translation system.

8. The method according to claim 1, wherein the peptide represented by the formula (I) contains an amino acid used for cyclization.

9. A method for producing a compound having a heterocycle introduced by an azoline backbone introducing enzyme comprising:
preparing a peptide represented by the following formula (I):

$$(Xaa_2)m\text{-}(Xaa_3)n\text{-}(Xaa_4)o \qquad (I)$$

wherein
$(Xaa_2)m$ represents m numbers of arbitrary amino acids and m represents an integer selected from 0 to 10;
$(Xaa_3)n$ represents n numbers of arbitrary amino acids, at least one of which is an amino acid selected from the group consisting of Cys, Ser, Thr, 2,3-diamino acids, homocysteine, homoserine, and 2,4-diamino acids, and analogs thereof, and n represents an integer selected from 2 to 40; and
$(Xaa_4)o$ represents o numbers of arbitrary amino acids and o represents an integer selected from 0 to 10, and
reacting the peptide with an azoline backbone introducing enzyme to which a leader sequence of a substrate or a partial sequence thereof has been bound to introduce a heterocycle into at least one of Cys, Ser, Thr, 2,3-diamino acids, homocysteine, homoserine, and 2,4-diamino acids, and analogs thereof of $(Xaa_3)n$,
wherein the peptide represented by the formula (I) contains an amino acid used for cyclization,
wherein the peptide represented by the formula (I) contains an amino acid having any of functional groups belonging to the following Functional group 1 and an amino acid having a functional group corresponding thereto in the following Functional group 2:

TABLE 1

| | Functional group 1 | Functional group 2 |
|---|---|---|
| (A) | 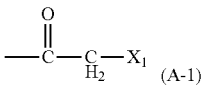 —C(=O)—CH₂—X₁ (A-1) | HS— (A-2) |
| (B) | —C≡C—H (B-1) | N₃— (B-2) |
| (C) | —Ar—CH₂NH₂ (C-1) | 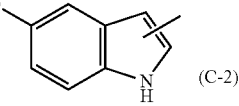 (C-2) |
| (D) | —C≡C—CH₂—X₁ (D-1) | HS— (D-2) |
| (E) | —Ar—CH₂—X₁ (E-1) | HS— (E-2) | wherein, $X_1$ represents Cl, Br, or I and Ar represents a substituted or unsubstituted aromatic ring.

10. The method according to claim 1, further comprising, after the step of introducing a heterocycle, cyclizing the heterocycle-containing compound.

11. A method for producing a compound containing a heterocycle introduced by an azole backbone introducing enzyme, comprising after the step of introducing a heterocycle in the method as claimed in claim 1
reacting the peptide having a heterocycle introduced therein with the azole backbone introducing enzyme and thereby converting at least one of the heterocycles introduced by the azoline backbone introducing enzyme into a heterocycle introduced by the azole backbone introducing enzyme.

12. A method of constructing a library including two or more compounds containing a heterocycle introduced by an azoline backbone introducing enzyme, comprising:
in step of preparing a peptide in the method as claimed in claim 1, preparing a peptide library including two or more peptides represented by the formula (I) but different in (Xaa₃)n and, in the step of introducing a heterocycle by an azoline backbone introducing enzyme in the above-described method, introducing the heterocycle in the peptide library, wherein the step of preparing a peptide library comprises constructing a nucleic acid library encoding the peptide library and translating the nucleic acid library in a cell-free translation system to construct the peptide library.

13. A method of constructing a library including two or more compounds containing a heterocycle introduced by an azoline backbone introducing enzyme, comprising:

in step of preparing a peptide in the method as claimed in claim 1, preparing a peptide library including a complex of two or more peptides represented by the formula (I) but different in (Xaa₃)n and mRNAs encoding the peptides, and in the step of introducing a heterocycle by an azoline backbone introducing enzyme in the above-described method, introducing the heterocycle in the peptide library, wherein the step of preparing a peptide library comprises constructing an mRNA library encoding the peptide library, binding puromycin to the 3' end of each of the mRNAs to construct a puromycin-bound mRNA library, and translating the puromycin-bound mRNA library in a cell-free translation system to construct a peptide-mRNA complex library.

14. A method of constructing a library including two or more compounds containing a heterocycle introduced by an azole backbone introducing enzyme, comprising:

constructing a library including two or more compounds containing a heterocycle introduced by an azoline backbone introducing enzyme by the method as claimed in claim 12, and reacting the library with the azole backbone introducing enzyme to convert at least one of the heterocycles introduced by the azoline backbone introducing enzyme into a heterocycle introduced by the azole backbone introducing enzyme.

15. A screening method for identifying a compound containing a heterocycle that binds to a target substance, comprising:

bringing a compound library constructed by the method as claimed claim 12 into contact with the target substance, and then incubating, and selecting the compound that has bound to the target substance.

16. A method of constructing a library including two or more compounds containing a heterocycle introduced by an azole backbone introducing enzyme, comprising:

constructing a library including two or more compounds containing a heterocycle introduced by an azoline backbone introducing enzyme by the method as claimed in claim 13, and reacting the library with the azole backbone introducing enzyme to convert at least one of the heterocycles introduced by the azoline backbone introducing enzyme into a heterocycle introduced by the azole backbone introducing enzyme.

17. A screening method for identifying a compound containing a heterocycle that binds to a target substance, comprising:

bringing a compound library constructed by the method as claimed in claim 13 into contact with the target substance, and then incubating, and selecting the compound that has bound to the target substance.

18. A screening method for identifying a compound containing a heterocycle that binds to a target substance, comprising:

bringing a compound library constructed by the method as claimed in claim 14 into contact with the target substance, and then incubating, and selecting the compound that has bound to the target substance.

19. The method according to claim 9, wherein the leader sequence of a substrate or the partial sequence thereof has been bound to the N terminal of the azoline backbone introducing enzyme.

20. The method according to claim 9, wherein the leader sequence or the partial sequence thereof has the following sequence:

MNKKNILPQQGQPVIRLTAGQLSSQLAELSEEALGDA (SEQ ID NO: 1)
MKEQNSFNLLQEVTESELDLILGA(SEQ ID NO: 2)
MILASLSTFQQMWISKQEYDEAGDA(SEQ ID NO: 3)
MELQLRPSGLEKKQAPISELNIAQTQGGDSQVLALNA (SEQ ID NO: 4); or a partial sequence thereof.

21. The method according to claim 9, wherein the leader sequence has been bound to the azoline backbone introducing enzyme via a spacer.

22. The method according to claim 9, wherein the (Xaa₃)n is (Xaa₅Xaa₆)p wherein, p numbers of Xaa₅ each independently represent an arbitrary amino acid, p numbers of Xaa₆ each independently represent an amino acid selected from the group consisting of Cys, Ser, Thr, 2,3-diamino acids, homocysteine, homoserine, and 2,4-diamino acids, and analogs thereof, and p is selected from 1 to 20.

23. The method according to claim 22, wherein the Xaa₆ is Cys.

24. The method according to claim 9, wherein the (Xaa₄)o contains, at the N terminal thereof, Ala-Tyr-Asp.

25. The method according to claim 9, wherein the step of preparing a peptide represented by the formula (I) comprises:

preparing a nucleic acid encoding the peptide represented by the formula (I), and translating the nucleic acid in a cell-free translation system.

* * * * *